(12) United States Patent
Strupp

(10) Patent No.: US 11,400,067 B2
(45) Date of Patent: *Aug. 2, 2022

(54) PHARMACEUTICAL COMPOSITIONS AND USES DIRECTED TO LYSOSOMAL STORAGE DISORDERS

(71) Applicant: INTRABIO LIMITED, Oxfordshire (GB)

(72) Inventor: Michael Strupp, Munich (DE)

(73) Assignee: INTRABIO LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/324,301

(22) PCT Filed: Aug. 11, 2017

(86) PCT No.: PCT/IB2017/054928
§ 371 (c)(1),
(2) Date: Feb. 8, 2019

(87) PCT Pub. No.: WO2018/029657
PCT Pub. Date: Feb. 15, 2018

(65) Prior Publication Data
US 2019/0201359 A1    Jul. 4, 2019

(30) Foreign Application Priority Data

Aug. 11, 2016 (GB) .................... 1613828
Feb. 16, 2017 (GB) .................... 1702552
Apr. 10, 2017 (GB) .................... 1705762
Apr. 28, 2017 (GB) .................... 1706854

(51) Int. Cl.
*A61K 31/198* (2006.01)
*A61P 25/00* (2006.01)
*A61K 31/13* (2006.01)

(52) U.S. Cl.
CPC ............ *A61K 31/198* (2013.01); *A61K 31/13* (2013.01); *A61P 25/00* (2018.01)

(58) Field of Classification Search
CPC .................................................. A61K 31/198
See application file for complete search history.

(56) References Cited

U.S. PATENT DOCUMENTS

2002/0095135 A1    7/2002    Meeker et al.

FOREIGN PATENT DOCUMENTS

| CN | 103814046 A | 5/2014 | |
|---|---|---|---|
| FR | 2 905 600 A1 | 3/2008 | |
| RU | 2012151575 A | 7/2014 | |
| WO | WO 2006/097527 A1 | 9/2006 | |
| WO | WO 2011/151685 A1 | 12/2011 | |
| WO | WO-2013182652 A1 * | 12/2013 | ........... A61K 31/405 |

OTHER PUBLICATIONS

Bremova et al (Niemann-Pick type C disease:effects of a therapy with acetyl DL-leucine and vestibular function, Graduate School Thesis: published Apr. 22, 2016) (Year: 2016).*
Reagan-Shaw et al (FASEBJ vol. 22 pp. 659-661 published 2007) (Year: 2007).*
Niemann-Pick Type C: Effects of a therapy with acetyl-DL-leucine and vestibular function: Dissertation for Graduate School Systemic Neurosciences der Ludwig-Maximilians-Universitat Munchen. Presented Orally to the public on Sep. 19, 2016 (Year: 2016).*
Bremova (Neurology vol. 85 pp. 1368-1375. Published Oct. 2015). (Year: 2015).*
International Search Report dated Nov. 6, 2017, PCT/IB2017/054928.
Lukas et al., "Enzyme Enhancers for the Treatment of Fabry and Pompe Disease," Molecular Therapy, vol. 23, No. 3, pp. 456-464, Mar. 1, 2015.
Japanese Office Action in Counterpart App. No. 2019-507811 dated May 7, 2021. 5 pages.
Schniepp et al., "Acetyl-DL-leucine improves gait variability in patients with cerebellar ataxia—a case series," Cerebellum & Ataxias (2016) (4 pages).
Search Report in Chinese Application No. 201780062740X, dated Aug. 14, 2021 (2 pages).
Search Report in Russian Application No. 2019106493, dated Oct. 26, 2020.

* cited by examiner

*Primary Examiner* — Theodore R. Howell
*Assistant Examiner* — George W Kosturko
(74) *Attorney, Agent, or Firm* — Finnegan, Henderson, Farabow, Garrett & Dunner, LLP

(57) ABSTRACT

The present disclosure provides for treating lysosomal storage disorders (LSDs) comprising administering acetyl-leucine or a pharmaceutically acceptable salt thereof.

34 Claims, 25 Drawing Sheets

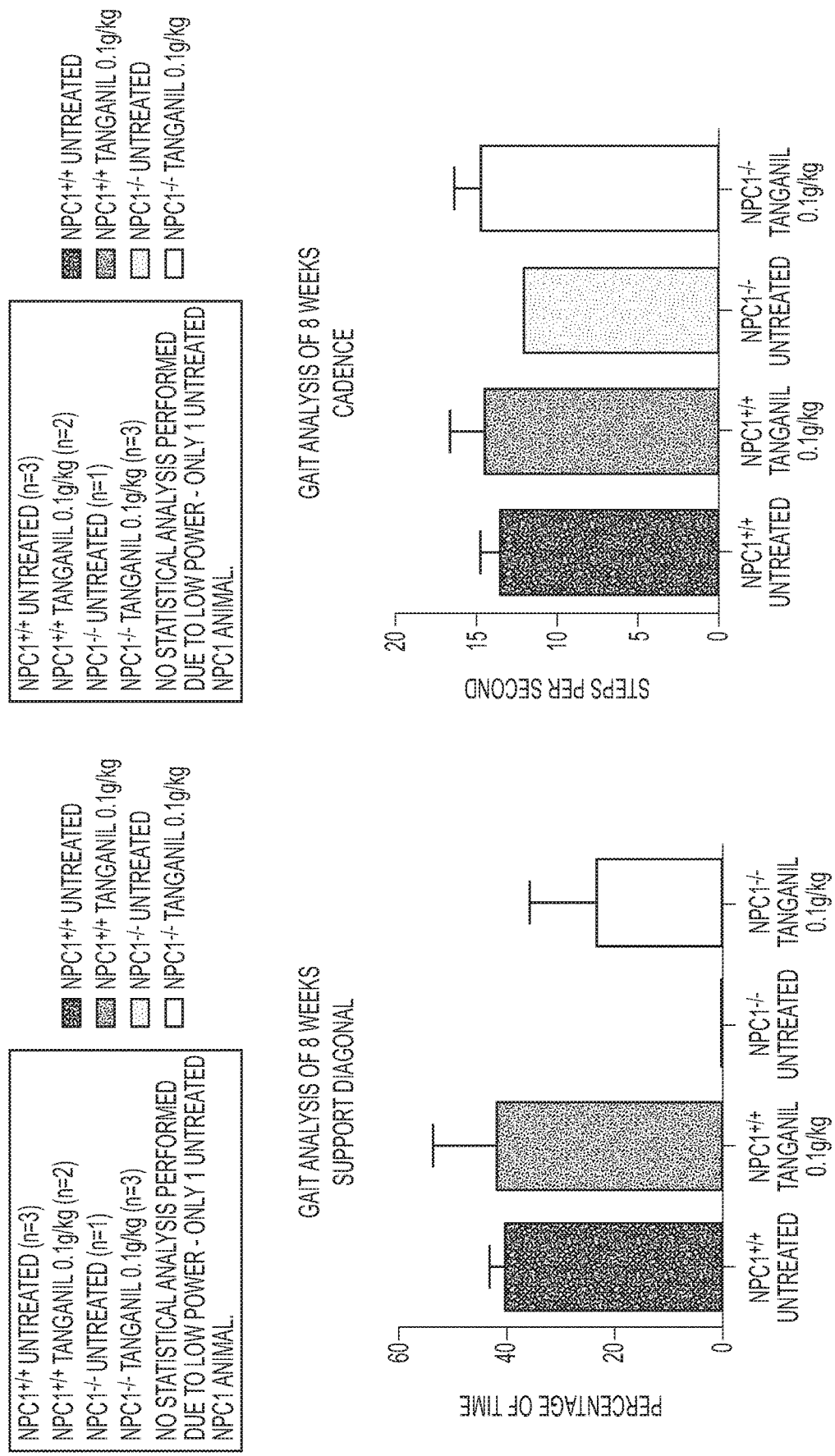

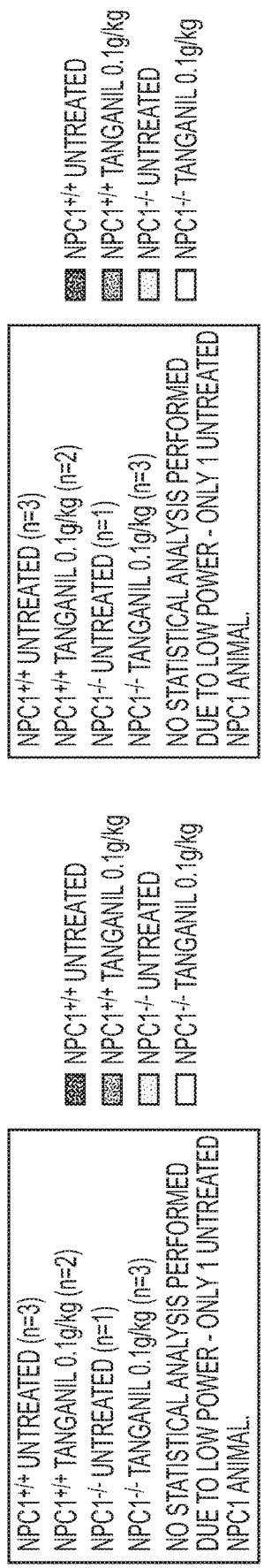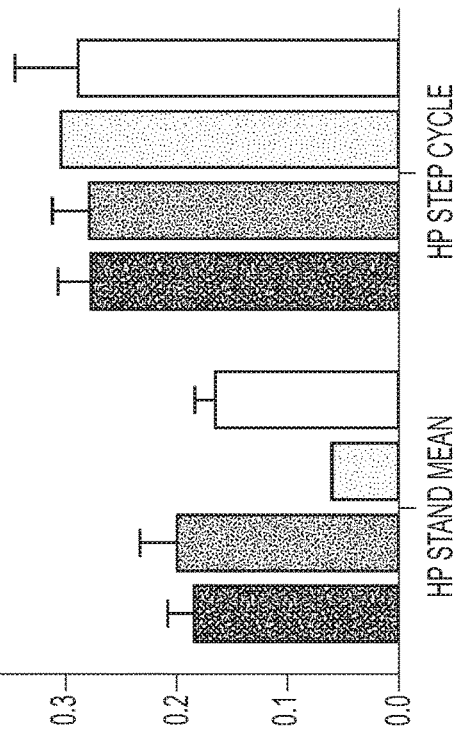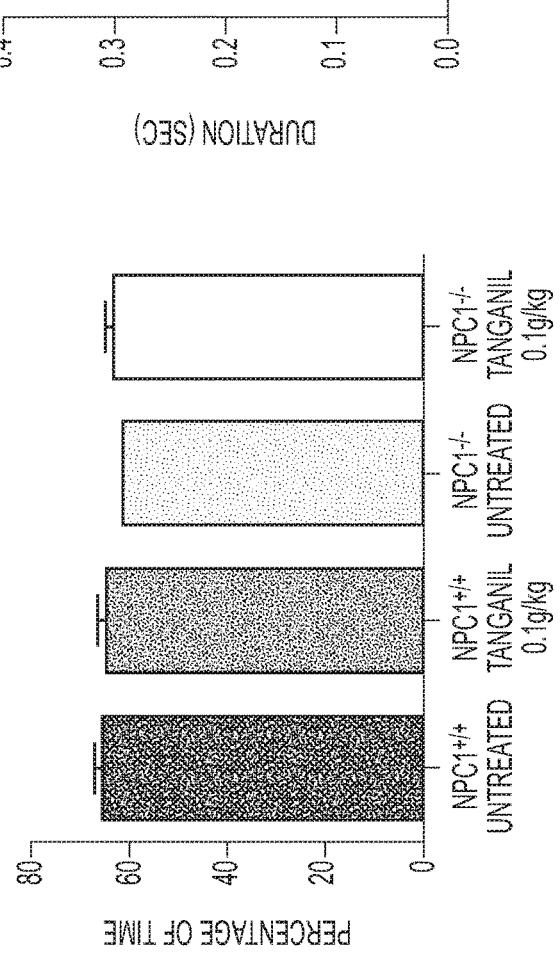
FIG. 3E
FIG. 3F

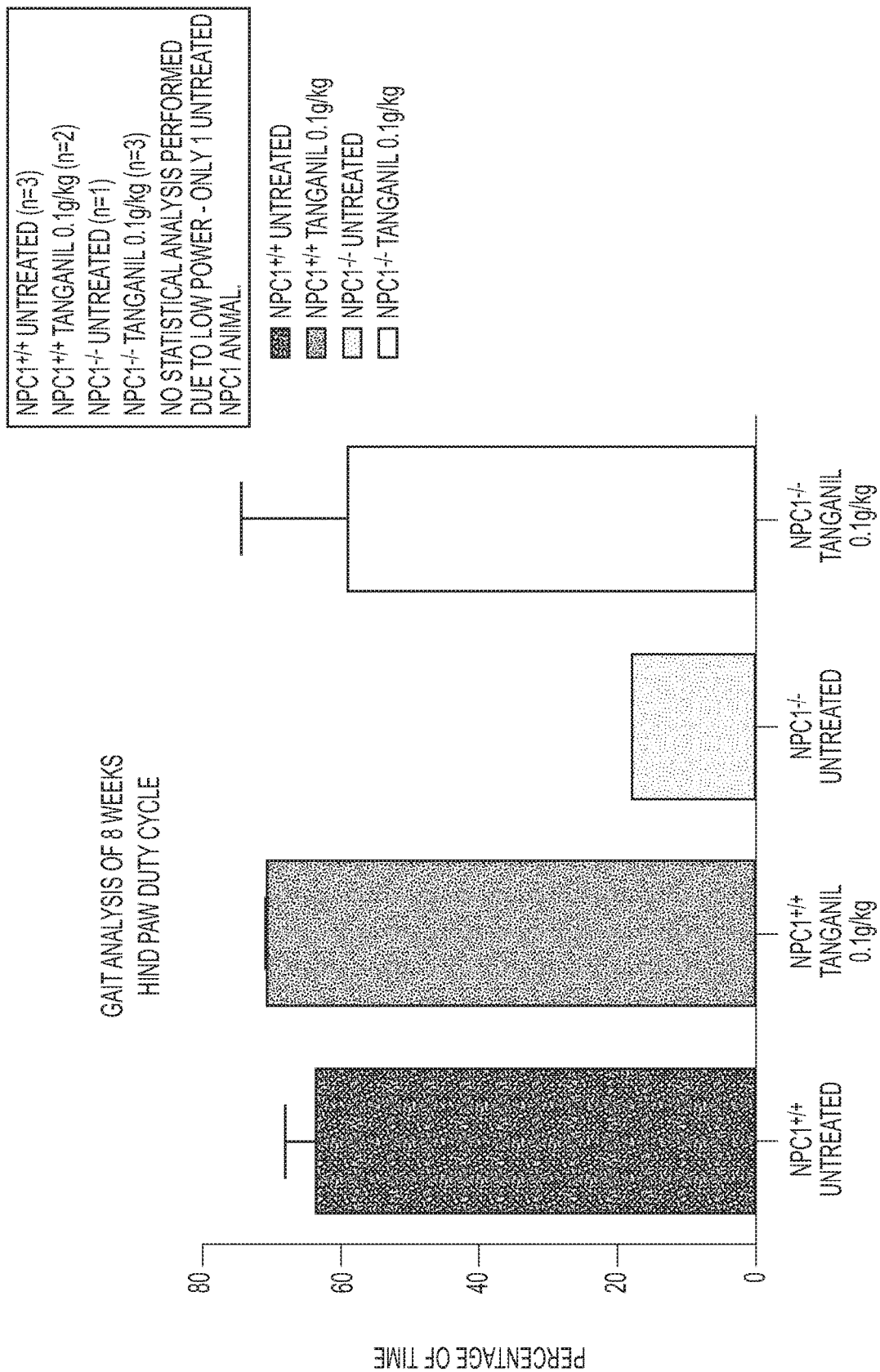

PHARMACEUTICAL COMPOSITIONS AND USES DIRECTED TO LYSOSOMAL STORAGE DISORDERS

This application is the United States national stage entry under 35 U.S.C. § 371 of International Application No. PCT/IB2017/054928, filed on Aug. 11, 2017, and published as WO 2018/029657, which claims priority to UK Patent Application No. 1613828.1, filed on Aug. 11, 2016, UK Patent Application No. 1702552.9, filed Feb. 16, 2017, UK Patent Application No. 1705762.1, filed Apr. 10, 2017, and UK Patent Application No. 1706854.5, filed Apr. 28, 2017; all of which are incorporated herein by reference in their entirety.

This application claims priority benefit to UK 1613828.1, filed Aug. 11, 2016, UK 1702552.9, filed Feb. 16, 2017, UK 1705762.1, filed Apr. 10, 2017, and UK 1706854.5, filed Apr. 28, 2017; all of which are incorporated herein by reference in their entirety.

Lysosomal storage disorders (LSDs) are a group of inherited metabolic diseases caused by defects in lysosomal homeostasis. To date, LSDs encompass over 70 diseases, with a collective clinical frequency of 1:5000 live births. These diseases can be classified into two main groups: primary storage disorders resulting from a direct deficiency in degradation pathways (typically lysosomal enzyme deficiency disorders), and secondary storage disorders which are caused by malfunctioning downstream lysosomal proteins or processes that impact the lysosome (e.g., defects in trafficking pathways).

The pathology of LSDs affects many of the body's systems, but most commonly the nervous system. Progressive neurodegeneration resulting in physical disability and mental deterioration are common symptoms. Such disorders are generally severely progressive and unremitting. They tend to present in the first few years of life and the severe progression results in frequent hospitalization. If left untreated, patients often die in their mid-teens. Adult-onset patients have also been described.

Current therapeutic approaches for LSDs are limited. There are few, if any, curative treatments and many of the therapeutic options merely improve quality of life. For example, some LSDs have been responsive to bone marrow transplantation or enzyme replacement therapy. Additionally, some benefit has been reported in a clinical trial of substrate reduction therapy (SRT) using an inhibitor of glycosphingolipid (GSL) biosynthesis: the imino sugar drug, miglustat (Patterson, 2006). However, there are currently no general non-specific treatments that benefit all LSDs. There is therefore a need to develop improved treatments of LSDs.

The present disclosure addresses this need and describes acetyl-leucine for treating a LSD or one or more symptoms of a LSD in a subject in need thereof.

In one embodiment, there is disclosed acetyl-leucine, or a pharmaceutically acceptable salt thereof, for use in a method of treating a LSD or one or more symptoms associated with a LSD in a subject in need thereof, wherein the LSD is not Niemann-Pick Type C.

In one embodiment of the present disclosure, acetyl-leucine, or a pharmaceutically acceptable salt thereof, is disclosed for use in a method of treating a LSD in a subject in need thereof, wherein the subject is asymptomatic.

In another embodiment, there is disclosed acetyl-leucine, or a pharmaceutically acceptable salt thereof, for use in a method of delaying onset of a LSD or one or more symptoms of a LSD that would otherwise be expected to manifest according to typical disease progression.

In a further embodiment, the present disclosure includes acetyl-leucine, or a pharmaceutically acceptable salt thereof, for use in a method of treating a LSD or one or more symptoms associated with a LSD in a subject in need thereof, wherein the method comprises administering a therapeutically effective amount of the acetyl-leucine to the subject in need thereof for a duration chosen from at least about 3 months, at least about 6 months, at least about 1 year, at least about 2 years, and at least about 5 years.

In one embodiment, the present disclosure describes acetyl-leucine, or a pharmaceutically acceptable salt thereof, for use in a method of delaying progression of a LSD or one or more symptoms associated with a LSD over time as compared to typical disease progression, wherein the method comprises administering a therapeutically effective amount of the acetyl-leucine to the subject in need thereof for a duration chosen from at least about 3 months, at least about 6 months, at least about 1 year, at least about 2 years, and at least about 5 years.

In a further embodiment, acetyl-leucine, or a pharmaceutically acceptable salt thereof, is disclosed for use in a method of reversing progression of a LSD or one or more symptoms associated with a LSD over time, wherein the method comprises administering a therapeutically effective amount of the acetyl-leucine to the subject in need thereof for a duration chosen from at least about 3 months, at least about 6 months, at least about 1 year, at least about 2 years, and at least about 5 years.

In another embodiment, acetyl-leucine, or a pharmaceutically acceptable salt thereof, is disclosed for use in a method of improving in a subject in need thereof a biochemical marker of a LSD over time, wherein the method comprises administering a therapeutically effective amount of the acetyl-leucine to the subject in need thereof for a duration chosen from at least about 3 months, at least about 6 months, at least about 1 year, at least about 2 years, and at least about 5 years.

In another embodiment, the present disclosure includes acetyl-leucine, or a pharmaceutically acceptable salt thereof, for use in a method of reducing the severity of a LSD or reducing the severity of or eliminating one or more existing symptoms associated with a LSD in a subject in need thereof, wherein the LSD is not Niemann-Pick Type C.

In a further embodiment, the present disclosure includes acetyl-leucine, or a pharmaceutically acceptable salt thereof, for use in a method of providing neuroprotection in a subject having, suspected of having, or at risk of having a LSD, wherein the method comprises administering a therapeutically effective amount of the acetyl-leucine to the subject for a duration chosen from at least about 3 months, at least about 6 months, at least about 1 year, at least about 2 years, and at least about 5 years.

Additional embodiments of the present disclosure include, acetyl-leucine, or a pharmaceutically acceptable salt thereof, for use in a method of delaying progression of a lysosomal storage disorder (LSD) in a subject. Acetyl-leucine, or a pharmaceutically acceptable salt thereof, for use in a method of providing neuroprotection in a subject having a LSD. The acetyl-leucine is in racemate form, in an enantiomeric excess of the L-enantiomer or in an enantiomeric excess of the D-enantiomer. The methods further comprise administering the acetyl-leucine in a dose of between 1.5 g and 10 g per day. Further, the methods comprise administering the acetyl-leucine for a treatment duration of two weeks or more. The methods may also comprise administering the acetyl-leucine, or a pharmaceutically acceptable salt thereof, before the onset of a symptom of a LSD. The methods may further comprise administering another therapy or agent intended to prevent or treat the LSD. A further embodiment of the present disclosure is a kit for delaying progression of a LSD in a subject, the kit comprising a means for diagnosing or prognosing a LSD, and acetyl-leucine or a pharmaceutically acceptable salt thereof. The kit comprises a means for diagnosing or prognosing a LSD, and acetyl-leucine or a pharmaceutically acceptable salt thereof. Still yet another embodiment of the present disclosure is use of acetyl-leucine, or a pharmaceutically acceptable salt thereof, as a neuroprotective agent in a subject having a LSD. In a further embodiment of the method, the kit, or the use, the LSD is Niemann-Pick Type C (NPC1 and/or NPC2 defect), Smith-Lemli-Opitz Syndrome (SLOS), an inborn error of cholesterol synthesis, Tangier disease, Pelizaeus-Merzbacher disease, a neuronal ceroid lipofuscinosis, a primary glycosphingolipidosis, Farber disease or multiple sulphatase deficiency. Additionally, in another embodiment of the method, the kit, or the use, the primary glycosphingolipidosis is Gaucher disease, Fabry disease, GM1 gangliosidosis, GM2 gangliosidosis, Krabbe disease or metachromatic leukodystrophy (MLD). A further embodiment of the method, the kit, or the use, the LSD is NPC, Tay-Sachs disease, Sandhoff disease, GM1 gangliosidosis, Fabry disease, a neurodegenerative mucopolysaccharidosis, MPS I, MPS IH, MPS IS, MPS II, MPS III, MPS IIIA, MPS IIIB, MPS IIIC, MPS HID, MPS, IV, MPS IV A, MPS IV B, MPS VI, MPS VII, MPS IX, a disease with secondary lysosomal involvement, SLOS, or Tangier disease. Another embodiment of the method, the kit, or the use, the LSD is Niemann Pick disease, Niemann Pick type C, Niemann Pick type A, Sandhoffs disease, Tay-Sachs disease or mucolipidosis type II.

These and other embodiments and features of the present disclosure will be apparent from the following description and the claims.

BRIEF DESCRIPTION OF THE FIGURES

FIGS. 3A-3G show gait analysis data for Npc1$^{-/-}$ mice compared to wild-type (Npc1$^{+/+}$) mice, with and without acetyl-DL-leucine treatment from weaning. For example, diagonal support, cadence and step sequence data are shown in FIGS. 3A-3C, respectively. FIGS. 3D and 3E show front paw (FP) data (stand mean and step cycle in panel D; duty cycle in panel E). FIGS. 3F and 3G show hind paw (HP) data (stand mean and step cycle in panel F; duty cycle in panel G).

DESCRIPTION

Figure 1A:
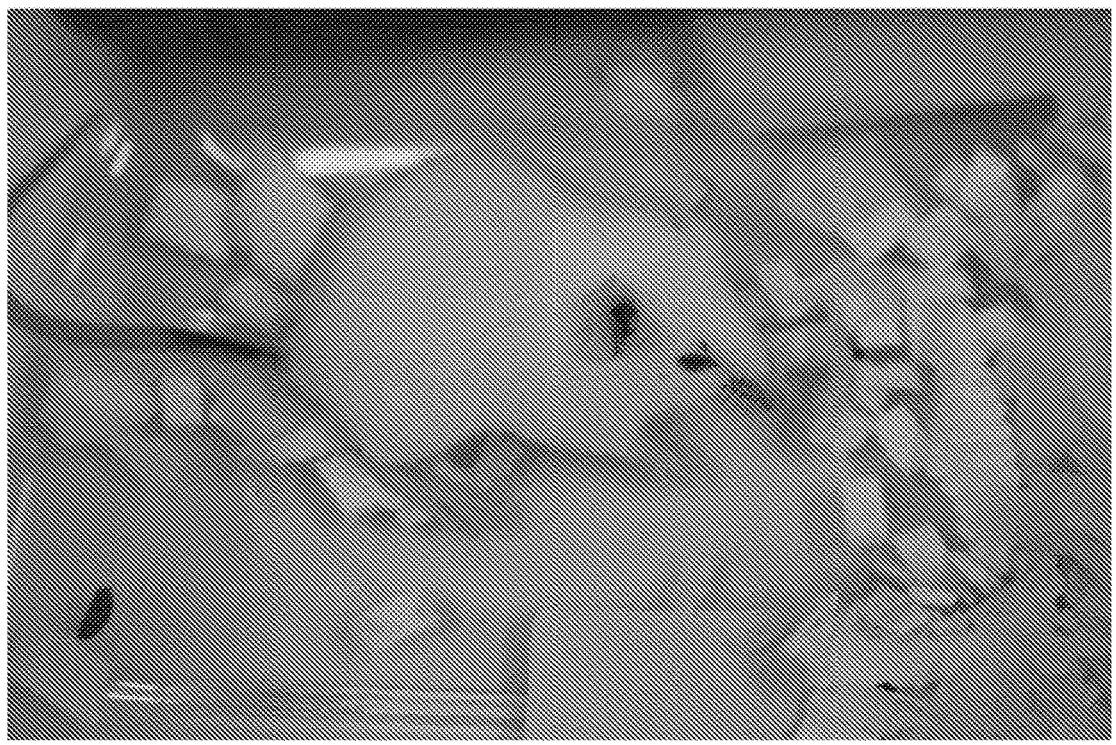
FIG. 1 shows photographs of treated (FIG. 1A) and untreated (FIG. 1B) Npc1$^{-/-}$ mice at nine weeks of age.

Acetyl-leucine in racemate form (acetyl-DL-leucine) and salts of the same are effective in the treatment of vertigo of various origins, notably Meniere's vertigo and vertigo of inflammatory (vestibular neuritis) or toxic origin. For example, acetyl-leucine is marketed by Pierre Fabre Medicament in racemate form as an anti-vertigo medicament under the tradename Tanganil®. Clinical results of Tanganil® reported by various authors demonstrate an improvement in vertigo symptomology in more than 95% of cases, including the disappearance of vertigo attacks.

Acetyl-DL-leucine has been used in France to treat acute vertigo since 1957 and has an excellent safety profile, but its long-term safety in chronic use has not been determined. Despite numerous hypotheses, including stabilisation of membrane potential, its pharmacological and electrophysiological modes of action remain unclear. (Vibert et al. (2001) Eur J Neurosci; 13(4): 735-48; Ferber-Viart et al. (2009) Audiol Neurootol; 14(1): 17-25). A FDG-µPET study in a rat model of an acute unilateral labyrinthectomy (Zwergal et al. (2016) Brain Struct Funct; 221(1): 159-70) showed a significant effect of an L-enantiomer, N-acetyl-L-leucine, on postural compensation by activation of the vestibulocerebellum and a deactivation of the posterolateral thalamus (Gunther et al. (2015) PLoS One; 10(3): e0120891). The symptomatic improvement of cerebellar ataxia using acetyl-DL-leucine was shown in a case series with cerebellar patients (Strupp et al. (2013) J Neurol; 260(10): 2556-61). Another case series did not find benefit (Pelz et al. (2015) J Neurol; 262(5): 1373-5). Quantitative gait analysis showed that acetyl-DL-leucine improved temporal gait variability in patients with cerebellar ataxia (Schniepp et al. (2015) Cerebellum; 3:8). In a one-month study involving 12 patients with Niemann-Pick Type C (NPC), symptomatic improvement of ataxia was shown (Bremova et al. (2015) Neurology; 85(16): 1368-75). Further, a PET study in patients with ataxia given acetyl-DL-leucine demonstrated an increased metabolism in the midbrain and lower brainstem in responders (Becker-Bense et al. (2015) Abstract EAN).

Acetyl-leucine, however, is not known to treat LSDs, which generally progress over the course of years to decades. The present disclosure surprisingly shows that acetyl-leucine, or a pharmaceutically acceptable salt of the same, can be used in a method of treating a LSD in a subject in need thereof, for example, by delaying onset of a LSD or one or more symptoms of a LSD that would otherwise be expected to manifest according to typical disease progression, and/or by delaying or reversing progression of a LSD or one or more symptoms of a LSD, such as over long durations, as compared to typical disease progression. These exemplary uses according to the present disclosure, as well as others described herein, were entirely unexpected, as such benefits had not been observed, and could not have been deduced, from the prior art teaching. LSDs are one of a heterogeneous group of inherited disorders often characterized by the accumulation of undigested or partially digested macromolecules resulting in cellular dysfunction (e.g., increased lysosomal volume compared to healthy subjects) and clinical abnormalities. As evidenced by the Examples, but without wishing to be bound by any specific theory, the present inventors discovered, inter alia, that, in subjects afflicted with a LSD, acetyl-leucine can improve cellular dysfunction (e.g., by reducing lysosomal volumes towards control values) and clinical abnormalities.

Consequently, the present disclosure provides acetyl-leucine, or a pharmaceutically acceptable salt of the same, for use in a method of treating a LSD or one or more symptoms of a LSD in a subject in need thereof.

"LSD", as used herein, refers to any disorder that involves dysfunction or disruption in the late endosomal/lysosomal system and the accumulation of undigested or partially digested macromolecules. The LSD may involve increased storage of lipids or non-lipids.

A "subject", as used herein, may be a vertebrate, mammal or domestic animal. Hence, compositions according to the disclosure may be used to treat any mammal, for example livestock (e.g., a horse, cow, sheep or pig), pets (e.g., a cat, dog, rabbit or guinea pig), a laboratory animal (e.g., a mouse or rat), or may be used in other veterinary applications. For example, the subject is a human being.

As used herein, the singular forms "a," "an," and "the" include plural reference.

The terms "approximately" and "about" mean to be nearly the same as a referenced number or value including an acceptable degree of error for the quantity measured given the nature or precision of the measurements. As used herein, the terms "approximately" and "about" should be generally understood to encompass ±20% of a specified amount, frequency or value. Numerical quantities given herein are approximate unless stated otherwise, meaning that term "about" or "approximately" can be inferred when not expressly stated.

The terms "administer," "administration," or "administering" as used herein refer to (1) providing, giving, dosing and/or prescribing by either a health practitioner or his authorized agent or under his direction a composition according to the disclosure, and (2) putting into, taking or consuming by the patient or person himself or herself, a composition according to the disclosure.

References to "acetyl-leucine" throughout include pharmaceutically acceptable salts of the same, even if not expressly stated.

The acetyl-leucine may be in racemic form, which means that the compound comprises about equal amounts of enantiomers. Alternatively it may be present in an enantiomeric excess of either the L-enantiomer or the D-enantiomer. The acetyl-leucine may be in a single enantiomeric form of either the L-enantiomer or the D-enantiomer. In one embodiment, the single enantiomeric form is the L-enantiomer. The racemic and enantiomeric forms may be obtained in accordance with known procedures in the art.

A "pharmaceutically acceptable salt" as referred to herein, is any salt preparation that is appropriate for use in a pharmaceutical application. Pharmaceutically acceptable salts include, but are not limited to, amine salts, such as N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine, tris(hydroxymethyl)aminomethane and the like; alkali metal salts, such as lithium, potassium, sodium and the like; alkali earth metal salts, such as barium, calcium, magnesium and the like; transition metal salts, such as zinc, aluminum and the like; other metal salts, such as sodium hydrogen phosphate, disodium phosphate and the like; mineral acids, such as hydrochlorides, sulfates and the like; and salts of organic acids, such as acetates, lactates, malates, tartrates, citrates, ascorbates, succinates, butyrates, valerates, fumarates and the like.

The acetyl-leucine, or a pharmaceutically acceptable salt of the same, may be formulated and administered to a subject in accordance with known teachings in the art. For example, the acetyl-leucine, or a pharmaceutically acceptable salt of the same, may be formulated as a pharmaceutical composition. The pharmaceutical composition may comprise acetyl-leucine or a pharmaceutically acceptable salt of the same and a pharmaceutically acceptable carrier. Reference to the pharmaceutical composition encompasses the active agent alone or in the form of a pharmaceutical composition.

The pharmaceutical composition may take any of a number of different forms depending, in particular, on the manner in which it is to be used. Thus, for example, it may be in the form of a powder, tablet, capsule, liquid, ointment, cream, gel, hydrogel, aerosol, spray, micellar solution, transdermal patch, liposome suspension or any other suitable form that may be administered to a person or animal in need of treatment.

A "pharmaceutically acceptable carrier" as referred to herein, is any known compound or combination of known compounds that are known to those skilled in the art to be useful in formulating pharmaceutical compositions. It will be appreciated that the carrier of the pharmaceutical composition should be one which is tolerated by the subject to whom it is given.

In one embodiment, the pharmaceutically acceptable carrier may be a solid, and the composition may be in the form of a powder or tablet. A solid pharmaceutically acceptable carrier may include, but is not limited to, one or more substances which may also act as flavouring agents, buffers, lubricants, stabilisers, solubilisers, suspending agents, wetting agents, emulsifiers, dyes, fillers, glidants, compression aids, inert binders, sweeteners, preservatives, dyes, coatings, or tablet-disintegrating agents. The carrier may also be an encapsulating material. In powders, the carrier may be a finely divided solid that is in admixture with the finely divided active agents according to the invention. In tablets, the active agent may be mixed with a carrier having the necessary compression properties in suitable proportions and compacted in the shape and size desired. The powders and tablets may, for example, contain up to 99% of the active agents. Suitable solid carriers include, for example, calcium phosphate, magnesium stearate, talc, sugars, lactose, dextrin, starch, gelatin, cellulose, polyvinylpyrrolidine, low melting waxes and ion exchange resins. In another embodiment, the pharmaceutically acceptable carrier may be a gel and the composition may be in the form of a cream or the like.

The carrier may include, but is not limited to, one or more excipients or diluents. Examples of such excipients are gelatin, gum arabicum, lactose, microcrystalline cellulose, starch, sodium starch glycolate, calcium hydrogen phosphate, magnesium stearate, talcum, colloidal silicon dioxide and the like.

In another embodiment, the pharmaceutically acceptable carrier may be a liquid. In one embodiment, the pharmaceutical composition is in the form of a solution. Liquid carriers are used in preparing solutions, suspensions, emulsions, syrups, elixirs and pressurized compositions. The acetyl-leucine may be dissolved or suspended in a pharmaceutically acceptable liquid carrier such as water, an organic solvent, a mixture of both or pharmaceutically acceptable oils or fats. The liquid carrier may contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid carriers for oral and parenteral administration include water (partially containing additives as above, e.g. cellulose derivatives, such as sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier may also be an oily ester such as ethyl oleate and isopropyl myristate. Sterile liquid carriers are useful in sterile liquid form compositions for parenteral administration. The liquid carrier for pressurised compositions may be a halogenated hydrocarbon or other pharmaceutically acceptable propellant.

Liquid pharmaceutical compositions, which are sterile solutions or suspensions, may be utilised by, for example, intramuscular, intrathecal, epidural, intraperitoneal, intravenous and particularly subcutaneous injection. The active agent may be prepared as a sterile solid composition that may be dissolved or suspended at the time of administration using sterile water, saline, or other appropriate sterile injectable medium.

The compositions may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The compositions may also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Acetyl-leucine and compositions comprising the same may alternatively be administered by inhalation (e.g. intranasally). Compositions may also be formulated for topical use. For instance, creams or ointments may be applied to the skin.

Acetyl-leucine may be incorporated within a slow- or delayed-release device. Such devices may, for example, be inserted on or under the skin, and the medicament may be released over weeks or even months. Such devices may be advantageous when long-term treatment with acetyl-leucine used according to the present disclosure is required and which would normally require frequent administration (e.g. at least daily administration).

In one embodiment, the pharmaceutical composition is in the form of a tablet. In tablets, the active agent may be mixed with a vehicle, such as a pharmaceutically acceptable carrier, having the necessary compression properties in suitable proportions and compacted in the shape and size desired. The tablets may contain up to 99% by weight of the active agents.

For example, the acetyl-leucine, or a pharmaceutically acceptable salt of the same, may be provided in a solid dosage form suitable for oral administration, notably in the form of a tablet.

Pharmaceutical compositions in solid oral dosage form, such as tablets, may be prepared by any method known in the art of pharmacy. Pharmaceutical compositions are usually prepared by mixing the acetyl-leucine, or a pharmaceutically acceptable salt thereof, with conventional pharmaceutically acceptable carriers.

A tablet may be formulated as is known in the art. Tanganil®, for example, includes wheat starch, pregelatinised maize (corn) starch, calcium carbonate and magnesium stearate as excipients. The same, or similar, excipients, for example, may be employed with the present disclosure.

The composition of each 700 mg Tanganil® tablet is as follows: 500 mg acetyl-DL-leucine, 88 mg wheat starch, 88 mg pregelatinised maize (corn) starch, 13 mg calcium carbonate and 11 mg magnesium stearate. The same tablets, for example, may be employed with the present disclosure.

The present disclosure describes acetyl-leucine, including compositions and methods thereof, for treating a LSD or one or more symptoms of a LSD in a subject in need thereof. The subject in need thereof may have a genetic, biochemical, or other similar identifiable marker of a LSD. For example, the marker of a LSD may be a cellular marker. The subject in need thereof may have been diagnosed as having a LSD. For example, the subject may have been diagnosed with a LSD according to a genetic, biochemical, or other similar identifiable marker. The subject in need thereof may be suspected of having or at risk of having a LSD. For example, the subject may have a genetic predisposition to a LSD (e.g., the subject may have one or more family members with a LSD). The subject in need thereof may be symptomatic (i.e., have one or more symptoms associated with a LSD). The subject in need thereof may be asymptomatic. It should be understood that the terms "symptomatic" and "asymptomatic" are used with reference to symptoms of a LSD. Subjects who have a genetic, biochemical, or other similar identifiable marker of a LSD, such as subjects who have been diagnosed with a LSD based on a genetic, biochemical, or other similar identifiable marker, but who have no further symptoms of the disease are included within the scope of "asymptomatic" for purposes of the present disclosure.

As used herein, "treating a LSD or one or more symptoms of a LSD" and the like refer to delaying onset of a LSD or one or more symptoms of a LSD that would otherwise be expected to manifest according to typical disease progression, reducing the severity of a LSD or reducing the severity of or eliminating one or more existing symptoms associated with a LSD, delaying progression of a LSD or one or more symptoms of a LSD over time as compared to typical disease progression, and/or reversing progression of a LSD or one or more symptoms of a LSD over time. "Treating a LSD or one or more symptoms of a LSD" may also refer to improving a biochemical marker of a LSD.

As used herein, "typical disease progression," "disease progression that would typically be expected" and the like refer to the typical or expected progression of a LSD, one or more symptoms associated with a LSD, or a biochemical marker of a LSD if the subject were untreated. Typical or expected disease progression may be based, for example, on a known scale, index, rating, or score, or other suitable test, for assessing the progression of a LSD, one or more symptoms associated with a LSD, or a biochemical marker of a LSD, such as those described herein. The scale, index, rating, score, or other suitable test may correspond to the progression of the LSD overall or to the progression of one or more symptoms associated with the LSD. For instance, typical or expected disease progression may be based on the typical or expected onset or severity of the LSD or a symptom or collection of symptoms associated with the LSD. The typical or expected disease progression may be determined on a subject-by-subject basis or may be based on what is typically observed for or experienced by a collection of subjects afflicted with the LSD, such as a population or subpopulation of subjects. Subpopulations may include, for example, subpopulations of the same gender, of the same or similar age, of the same or similar timing for the onset of one or more symptoms, etc.

In one embodiment, "treating a LSD or one or more symptoms of a LSD" refers to delaying onset of a LSD or one or more symptoms of a LSD that would otherwise be expected to manifest according to typical disease progression. As used herein, "delaying onset of a LSD or one or more symptoms of a LSD" and the like refer to increasing the time to, or preventing, onset of the LSD or one or more symptoms of the LSD. For example, onset can be said to be delayed when the time to manifestation of a LSD or one or more symptoms of a LSD takes at least 5% longer than that observed according to typical disease progression. Further for example, an increase in time of at least 10%, at least 15%, at least 20%, at least 25%, at least 30%, at least 40%, at least 50%, at least 60%, at least 70%, at least 80%, at least 90% or at least 100% is observed. In one embodiment, the subject is asymptomatic. The administration of acetyl-leucine may be initiated at the time the subject is asymptomatic to delay onset of a LSD or one or more symptoms of a LSD that would otherwise be expected to manifest according to typical disease progression. In another embodiment, the subject is symptomatic. The administration of acetyl-leucine may be initiated at the time the subject has some symptoms in order to delay onset of one or more additional symptoms of a LSD that would otherwise be expected to manifest according to typical disease progression. The subject in need thereof may continue to receive treatment with acetyl-leucine in accordance with the durations described herein. In one embodiment, the treatment prevents onset of one or more symptoms of the LSD that would otherwise be expected to manifest according to typical disease progression.

In one embodiment, "treating a LSD or one or more symptoms of a LSD" refers to reducing the severity of a LSD or reducing the severity of or eliminating one or more existing symptoms associated with a LSD. The severity of a LSD or of the existing symptom(s) may be assessed using a known scale, index, rating, or score, such as those described as examples herein, or another suitable test for assessing severity. For example, the scale, index, rating, score, or other suitable test may correspond to the severity of the LSD overall or to the severity of one or more symptoms associated with the LSD. In one embodiment, the treatment improves such an assessment from a value or degree characteristic of a symptomatic patient to a value or degree characteristic of a non-symptomatic patient.

In one embodiment, "treating a LSD or one or more symptoms of a LSD" refers to delaying progression of a LSD or one or more symptoms associated with a LSD over time as compared to typical disease progression, or reversing progression of a LSD or one or more symptoms associated with a LSD over time. The time over which the treatment delays or reverses progression may coincide with the duration of treatment as described herein. The treatment may delay or reverse progression over a duration of, for example, about seven days or more, about two weeks or more, about three weeks or more, about one month or more, about six weeks or more, about seven weeks or more or about two months or more. For example, the treatment delays or reverses progression over a duration of about three months or more, about four months or more, about five months or more or about six months or more. Further for example, it delays or reverses progression over a duration of about 1 year or more, about 2 years or more, about 3 years or more, about 4 years or more, about 5 years or more, or about 10 years or more. The treatment may delay or reverse progression of the LSD or one or more symptoms associated with the LSD over the lifetime of the patient.

In one embodiment, "treating a LSD or one or more symptoms of a LSD" refers to delaying progression of a LSD or one or more symptoms of a LSD over time as compared to typical disease progression. As used herein, "delaying progression of a LSD or one or more symptoms associated with a LSD over time" and the like refer to slowing and/or stopping progression of the LSD or one or more symptoms of the LSD (e.g., slowing and/or stopping the worsening or increasing severity of the LSD or one or more symptoms of the LSD) over time. Disease progression may be determined, for example, using a known scale, index, rating, or score, such as those described as examples herein, or other suitable tests for assessing progression. For example, the scale, index, rating, score, or other suitable test may correspond to the progression of the LSD overall or to the progression of one or more symptoms associated with the LSD. In one embodiment, "delaying progression of a LSD or one or more symptoms associated with a LSD" means that a subject's disease severity value (e.g., overall severity or severity of one or more symptoms) determined by a known scale, index, rating, score, etc., or another suitable test for evaluating severity, does not meaningfully increase (e.g., at least remains substantially constant). In one embodiment, "delaying progression of a LSD or one or more symptoms of a LSD" means preventing the subject from reaching, or increasing the time taken for a subject to reach (e.g., decreasing the rate of change of increasing severity), a severity value according to a known scale, index, rating, score, etc., or other suitable test, for assessing progression compared to a value corresponding to typical disease progression. For example, progression can be said to be delayed when the time to reach a severity value takes at least 5% longer than that observed according to typical disease progression. Further for example, an increase in time of at least 10%, at least 15%, at least 20%, at least 25%, at least 30%, at least 40%, at least 50%, at least 60%, at least 70%, at least 80%, at least 90% or at least 100% is observed. The time over which the treatment delays progression of a LSD or one or more symptoms of a LSD may coincide with the duration of treatment as described herein. In one embodiment, the treatment delays progression for at least about three months, at least about four months, at least about five months, or at least about six months. In another embodiment, the treatment delays progression for at least about 1 year, at least about 2 years, at least about 3 years, at least about 4 years, at least about 5 years, or at least about 10 years. The treatment may delay progression over the lifetime of the patient.

In one embodiment, "treating a LSD or one or more symptoms of a LSD" refers to reversing progression of a LSD or one or more symptoms of a LSD over time. As used herein, "reversing progression of a LSD or one or more symptoms of a LSD over time" and the like refer to stopping progression and reducing the severity of the LSD or one or more symptoms of the LSD over time. Disease progression and severity may be determined, for example, using a known scale, index, rating, or score, such as those described as examples herein, or another suitable test for assessing progression and severity. For example, the scale, index, rating, score, or other suitable test may correspond to the progression and severity of the LSD overall or to the progression and severity of one or more symptoms associated with the LSD. In one embodiment, "reversing progression of a LSD or one or more symptoms of a LSD over time" means that a subject's disease severity value (e.g., overall severity or severity of one or more symptoms) determined by a known scale, index, rating, score, etc., or another suitable test, for evaluating severity, improves over time (i.e., shows a reduction in severity over time). The time over which the treatment reverses progression of a LSD or one or more symptoms of a LSD may coincide with the duration of treatment as described herein. In one embodiment, the treatment reverses progression for at least about three months, at least about four months, at least about five months, or at least about six months. In another embodiment, the treatment reverses progression for at least about 1 year, at least about 2 years, at least about 3 years, at least about 4 years, at least about 5 years, or at least about m years. The treatment may reverse progression over the lifetime of the patient.

In one embodiment, "treating a LSD or one or more symptoms of a LSD" refers to improving in the subject a biochemical marker of a LSD (e.g., increased levels of the storage metabolite(s) or secondary biochemical changes resulting from the primary storage). A biochemical marker is a signal of disease activity and may provide ongoing indications of disease severity and progression over time. In one embodiment, the biochemical marker is improved in view of a control value. In one embodiment, the biochemical marker is chosen from increased lysosomal volume and increased glycosphingolipid (GSL) levels. In one embodiment, the biochemical marker is increased lysosomal volume and the treatment reduces lysosomal volume in the subject. In one embodiment, the biochemical marker is increased glycosphingolipid (GSL) levels and the treatment reduces GSL levels in the subject. In one embodiment, the treatment improves a biochemical marker over time. For example, in one embodiment, improving a biochemical marker over time means that the treatment improves a biochemical marker over time toward a control value, prevents the progression of a biochemical marker over time, and/or delays the progression of the biochemical marker over time as compared to typical disease progression. The time over which the treatment improves a biochemical marker may coincide with the duration of treatment as described herein. In one embodiment, the treatment improves a biochemical marker for at least about three months, at least about four months, at least about five months, or at least about six months. In a further embodiment, the treatment improves a biochemical marker for at least about 1 year, at least about 2 years, at least about 3 years, at least about 4 years, at least about 5 years, or at least about 10 years. The treatment may improve the biochemical marker over the lifetime of the patient.

A "symptom" of a LSD includes any clinical or laboratory manifestation associated with a LSD and is not limited to what the subject can feel or observe. Symptoms as described herein include, but are not limited to, neurological symptoms and psychiatric symptoms. Examples of neurological symptoms include ataxia, other movement disorders such as hypokinesia, rigor, tremor or dystonia, central ocular motor disorders such as vertical and horizontal supranuclear saccade/gaze palsy and neuropsychological deficits such as dementia. Examples of psychiatric symptoms include depression, behavioural disorders or psychosis. Onset of symptoms may range from birth to adulthood.

Progression of a LSD or one or more symptoms of a LSD over time or through treatment can be monitored, for example, using one or more known tests at two or more time points and comparing the results. Disease progression and/or severity can be assessed, for example, using the Scale for the Assessment and Rating of Ataxia (SARA), Spinocerebellar Ataxia Functional Index (SCAFI), the International Cooperative Ataxia Rating Scale (ICARS), the brief ataxia rating scale (BARS), the modified Disability Rating Scale (mDRS), EuroQol 5Q-5D-5L (EQ-5D-5L), the visual analogue scale (VAS), Wechsler Adult Intelligence Scale-Revised (WAIS-R), Wechsler Intelligence Scale for Children-IV (WISC-IV), Montreal Cognitive Assessment (MoCA) or other suitable tests. For certain LSDs, such as NPC, particular scores have been developed and validated over the last decades, for instance the clinical severity score (CSS) and annual severity increment score (ASIS) (see Yanjanin et al., "Linear Clinical Progression, Independent of Age of Onset, in Niemann-Pick Disease, Type C," *Am J Med Genet Part B* 153B:132-140) and the modified 6-Domain NP-C disability Scale (mDRS score). For example, an NPC patient's severity can be quantified by assigning a CSS, which assesses various parameters of the disease (ambulation, seizures, eye movement, etc.) and gives each parameter a score out of 5. A higher score equals a greater severity. The ASIS quantifies the annual rate of change in the CSS, calculated by dividing the CSS by the patient's age. In this regard, certain scores in these tests are characteristic of symptomatic LSD patients and evidence disease progression and/or severity.

Thus, "treating a LSD or one or more symptoms of a LSD," for example, may be equated to achieving an improved assessment, such as those described herein, of a SARA, SCAFI, ICARS, BARS, mDRS, EQ-5D-5L, VAS, WAIS-R, WISC-IV, CSS and/or MoCA score, or result of another test suitable for characterising a LSD subject. For example, in one embodiment, "reducing the severity of a LSD or reducing the severity of or eliminating one or more existing symptoms of a LSD" means improving a SARA, SCAFI, ICARS, BARS, mDRS, EQ-5D-5L, VAS, WAIS-R, WISC-W, CSS and/or MoCA score, or a result of another suitable test for evaluating severity, such as improving the score or result from a severity value characteristic of a symptomatic subject to a value characteristic of a non-symptomatic subject. In another embodiment, "delaying progression of a LSD or one or more symptoms of a LSD" means that a subject's SARA, SCAFI, ICARS, BARS, mDRS, EQ-5D-5L, VAS, WAIS-R, WISC-W, CSS and/or MoCA score, or a result of another suitable test for evaluating progression, does not meaningfully increase (e.g., at least remains substantially constant). In a further embodiment, "delaying progression of a LSD or one or more symptoms of a LSD" means preventing a subject's SARA, SCAFI, ICARS, BARS, mDRS, EQ-5D-5L, VAS, WAIS-R, WISC-IV, CSS and/or MoCA score, or a result of another suitable test for evaluating progression, from reaching, or increasing the time taken to reach, a value compared to that of typical disease progression. In another embodiment, "reversing progression of a LSD or one or more symptoms of a LSD over time" means that a subject's SARA, SCAFI, ICARS, BARS, mDRS, EQ-5D-5L, VAS, WAIS-R, WISC-IV, CSS and/or MoCA score, or result of another suitable test for evaluating progression, improves over time (i.e., shows a reduction in severity over time).

For example, to evaluate overall neurological status, mDRS, a four-domain scale (ambulation, manipulation, language and swallowing), may be applied. Cerebellar function may be evaluated using SARA, an eight-item clinical rating scale (gait, stance, sitting, speech, fine motor function and taxis; range 0-40, where 0 is the best neurological status and 40 the worst), and SCAFI, comprising the 8-m-Walking-Time (8MW; performed by having patients walking twice as quickly as possible from one line to another excluding turning), 9-Hole-Peg-Test (9HPT) and the number of "PATA" repetitions over 10 s. Subjective impairment and quality of life may be evaluated using the EQ-5D-5L questionnaire and VAS. To assess ocular motor function, 3-dimensional videooculography (EyeSeeCam) may be used to measure the peak velocity of saccades, gain of smooth pursuit, peak slow phase velocity of gaze-evoked nystagmus (gaze-holding function), peak slow phase velocity of optokinetic nystagmus, and gain of horizontal vestibulo-ocular reflex. To evaluate the cognitive state, WAIS-R or WISC-IV, and MoCA, assessing different cognitive domains, including attention and concentration, executive functions, memory, language, visuoconstructional skills, conceptual thinking, calculations, and orientation with a maximum of 30 points and a cut-off score of 26, may be used. The skilled person will know how to perform these and other such tests.

The acetyl-leucine, or a pharmaceutically acceptable salt of the same, may be administered, for example, at a dose ranging from about 500 mg to about 15 g per day or ranging from about 500 mg to about 10 g per day, such as ranging from about 1.5 g to about 10 g per day, optionally by solid oral or liquid oral route. The acetyl-leucine, or a pharmaceutically acceptable salt of the same, may be administered, for example, in a dose according to that of Tanganil®, which is prescribed to adults in a dose of 1.5 g to 2 g per day, 3-4 tablets in two doses, morning and evening.

If one enantiomer is administered, the doses may be reduced accordingly. For instance if only acetyl-L-leucine or if only acetyl-D-leucine is administered, the dose may range from about 250 mg to about 15 g per day, range from about 250 mg to about 10 g per day, or range from about 250 mg to about 5 g per day, such as from about 0.75 g to about 5 g per day.

In one embodiment, the administered dose ranges from about 1 g to about 15 g per day, from about 1 g to about 10 g per day, or from about 1.5 g to about 7 g per day. It may be from about 2, 3, 4, 5, 6, 7, 8, 9, 10, 11, 12, 13, or 14 g to about 15 g per day. It may be from about 2, 3, 4, 5, 6, 7, 8 or 9 g to about 10 g per day. It may be more than about 1.5 g per day, but less than about 15, 14, 13, 12, 11, 10, 9, 8, 7, 6 or 5 g per day. In one embodiment, the dose ranges from about 4 g to about 6 g per day. In another embodiment, the dose ranges from about 4 g to about 5 g per day. In one embodiment, the dose is about 4.5 g per day. In one embodiment, the dose is about 5 g per day. In one embodiment, these doses are administered in a solid oral dosage form, notably tablets. In another embodiment, these doses are for acetyl-leucine when in its racemic form. Doses for acetyl-leucine when an enantiomeric excess is present may be lower than those recited here, for example, around 50% lower. The above recited dose-ranges when halved are thus also explicitly encompassed by the present disclosure.

The total daily dose may be spread across multiple administrations, i.e. administration may occur two or more times a day to achieve the total daily dose. As an example, the required number of tablets to provide the total daily dose of acetyl-leucine may be split across two administrations (for example, in the morning and evening) or three administrations (for example, in the morning, noon and evening). Each dose may be suitably administered with or without food. For example, acetyl-leucine may be dosed by about 1 or about 2 hours before meals, such as at least about 20 minutes, at least about 30 minutes, at least about 40 minutes, or at least about 1 hour before meals, or may be dosed by about 1, about 2, or about 3 hours after meals, such as waiting at least about 20 minutes, at least about 30 minutes, at least about 1 hour, at least about 1.5 hours, at least about 2 hours, or at least about 2.5 hours after meals. For example, a total daily dose of 4.5 g acetyl-DL-leucine may be administered as three Tanganil® (or equivalent) tablets before, with, or after breakfast, three further tablets before, with, or after lunch, and three further tablets before, with, or after dinner.

Administration of acetyl-leucine in accordance with the present disclosure may be initiated before or after a subject is found to have a genetic, biochemical, or other similar identifiable marker of a LSD, such as, in the case of the former, when the subject is suspected of having or is at risk of having a LSD. Administration may be initiated at or around the time a subject is found to have a genetic, biochemical, or other similar identifiable marker of a LSD. Similarly, administration may be initiated before, at or around the time, or after a subject is diagnosed with a LSD, such as before, at or around the time, or after a subject is found to have a genetic, biochemical, or other similar identifiable marker of a LSD. Administration of acetyl-leucine may be initiated when the subject is symptomatic or asymptomatic. In particular, one of the advantages of treatment with acetyl-leucine, according to the present disclosure, is that the administration of acetyl-leucine may be initiated as early as the time after a subject is found to have a genetic and/or biochemical marker of a LSD but before the subject shows symptoms of the LSD (other than the genetic and/or biochemical marker, i.e., the subject is asymptomatic) or before the subject shows one or more symptoms considered hallmarks of the disease. The treatment may delay onset of the LSD or one or more symptoms associated with the LSD, as described herein. The treatment may also be continued for a duration as described herein.

As discussed herein, an advantage of treatment with acetyl-leucine, according to the present disclosure, is that acetyl-leucine may be administered over a long duration of time to, for example, delay or even reverse progression of a LSD or one or more symptoms of a LSD in a subject as compared to typical disease progression. Treatment duration may be, for example, about seven days or more, about two weeks or more, about three weeks or more, about one month or more, about six weeks or more, about seven weeks or more, or about two months or more. In one embodiment, it is about three months or more, about four months or more, about five months or more or about six months or more. The treatment duration may be about 1 year or more, about 2 years or more, about 4 years or more, about 5 years or more, or about 10 years or more. The treatment duration may be the life-time of the patient.

Any and all combinations of dosage form, dose amount, dosing schedule and treatment duration are envisaged and encompassed by the invention. In one embodiment, the dose is from about 4 g to about 10 g per day, taken across one, two, or three administrations per day, for a treatment duration of about two months or more. In another embodiment, the dose is more than 4 g but no more than 5 g per day, taken across one, two, or three administrations per day, for a treatment duration of about six months or more. The dosage form may be a solid oral dosage form, notably tablets.

The pharmaceutical composition may be used as a monotherapy (e.g., use of the active agent alone) for treating a LSD in a subject. Alternatively, the pharmaceutical composition may be used as an adjunct to, or in combination with, other known therapies, e.g., for treating a LSD in a subject.

All LSDs, which may be classified in various ways, are within the scope of the present disclosure. In one embodiment, the LSD is chosen from any of glycogen storage disease, mucopolysaccaridoses, mucolipidoses, oligosaccharidoses, lipidoses, sphingolipidoses, and lysosomal transport diseases.

The sphingolipidoses may be chosen from any of Niemann-Pick disease type A/B, Gaucher disease types I, II, and III, Krabbe disease, Fabry disease, Schindler Disease, GM1 gangliosidosis, Morquio B disease, GM2 gangliosidoses, metachromatic leukodystrophy, Farber disease, multiple sulfatase deficiency, lysosomal acid lipase deficiency and galactosialidosis. In one embodiment, the sphingolipidoses are chosen from Niemann-Pick disease type A, GM1 gangliosidosis, Tay-Sachs disease, the AB variant of Tay-Sachs disease, and Sandhoff disease.

The mucolipidoses may be chosen from any of mucolipidosis I, mucolipidosis II, mucolipidosis III, and mucolipidosis IV. In one embodiment the mucolipidosis is mucolipidosis II or mucolipidosis III.

The mucopolysaccharidoses may be chosen from any of MPS IH, MPS I H-S, MPS IS, MPS IIA, MPS IIB, MPS IIIA-D, MPS IVA, MPS VI, MPS VII and MPS IX. In one embodiment, the mucopolysaccharidosis is MPS III or MPS VII. In one embodiment, the mucopolysaccharidosis is MPS IIIB.

The oligosaccharidoses may be chosen from any of beta-mannosidosis, alpha-fucosidosis, and aspartylglucosaminuria. In one embodiment, the oligosaccharidosis is aspartylglucosaminuria.

The lipidoses may be chosen from any of Niemann-Pick disease type C, Niemann-Pick disease type D, neuronal ceroid lipofuscinoses (Type I to X inclusive), and Wolman disease. In one embodiment, the lipidosis is Niemann-Pick disease type C.

The glycogen storage disease may be chosen from Infantile-onset Pompe disease, Late-onset Pompe disease and Danon disease.

The lysosomal transport diseases may be chosen from cystinosis, pycnodysostosis, sialic acid storage disease and infantile free sialic acid storage disease.

The LSD may be a primary lysosomal hydrolase defect, a post-translational processing defect of lysosomal enzymes, a trafficking defect for lysosomal enzymes, a defect in lysosomal enzyme protection, a defect in soluble non-enzymatic lysosomal proteins, a transmembrane (non-enzyme) protein defect or an unclassified defect.

In one embodiment, the LSD is chosen from a primary lysosomal hydrolase defect. Primary lysosomal hydrolase defects include, but are not limited to, Tay-Sachs disease (β-hexosaminidase A defect), Sandhoff disease (β-hexosaminidase A+B defect), Fabry disease (α-galactosidase A defect), Krabbe disease (β-galactosyl ceramidase defect), Niemann-Pick Type A and B (sphingomyelinase defect), metachromatic leukodystrophy (arylsulphatase A defect), MPS IH (Hurler syndrome; α-iduronidase defect), MPS IS (Scheie syndrome; α-iduronidase defect), MPS IH-S(Hurler-Scheie syndrome; α-iduronidase defect), MPS II (Hunter syndrome; iduronate sulphatase defect), MPS IIIA (Sanfilippo A syndrome; heparan sulphamidase defect), MPS IIIB (Sanfilippo B syndrome; acetyl α-glucosaminidase defect), MPS IIIC (Sanfilippo C syndrome; acetyl CoA: α-glucosaminide N-acetyltransferase defect), MPS IIID (Sanfilippo D syndrome; N-acetyl glucosamine-6-sulphatase defect), MPS IV A (Morquio A disease; acetyl galactosamine-6-sulphatase defect), MPS IVB (Morquio B disease; β-galactosidase defect), MPS V (redesignated MPS IS), MPS VI (Maroteaux Lamy Syndrome; acetyl galactosamine-4-sulphatase (arylsulphatase B) defect), MPS VII (Sly Syndrome; β-glucuronidase defect), MPS IX (hyaluronidase defect), Wolman/cholesteryl ester storage disease (WD; acid lipase defect), Pompe disease (Type II; α 1,4-glucosidase defect), aspartylglucosaminuria (glycosylasparaginase defect), fucosidosis (α-fucosidase defect), α-mannosidosis (α-mannosidase defect), β-mannosidosis (β-mannosidase defect), Schindler disease (N-acetylgalactosaminidase defect), sialidosis/ML I (α-neuraminidase defect), infantile neuronal ceroid lipofuscinosis (CLN1; palmitoyl protein thioesterase defect), late infantile neuronal ceroid lipofuscinosis (CLN2; carboxypeptidase defect), early infantile GM1 gangliosidosis, late infantile GM1 gangliosidosis, adult infantile GM1 gangliosidosis, Gaucher Disease Type 1 (Non-Neuronopathic), Gaucher Disease Type 2/3 (Neuronopathic), Neuronal Ceroid Lipofuscinosis Type 4 (CLN4; Kufs disease; Adult NCL; palmotoyl-protein thioesterase-1 deficiency (Type A); Cathepsin F deficiency (Type B)), Neuronal Ceroid Lipofuscinosis Type 4 (CLN10; Congenital Cathepsin D Deficiency), Pycnodysostosis (Cathepsin K defect), Infantile-Onset Pompe Disease, Late-Onset Pompe Disease, Farber Disease (Farber's lipogranulomatosis; ceramidase deficiency; Fibrocytic dysmucopolysaccharidosis; Lipogranulomatosis) and Galactosialidosis (protective protein cathepsin A defect, PPCA defect). In one embodiment, the primary lysosomal hydrolase defect is chosen from Tay-Sachs disease, Sandhoff disease, Niemann-Pick Type A, Niemann-Pick Type B, neuronal ceroid lipofuscinoses, Gaucher disease, Fabry disease, Krabbe disease, GM1 gangliosidosis, GM2 gangliosidosis, metachromatic leukodystrophy, and Farber disease. In one embodiment, the primary lysosomal hydrolase defect is chosen from Tay-Sachs disease, Sandhoff disease, Niemann-Pick Type A, Niemann-Pick Type B, and GM1 gangliosidosis.

In one embodiment, the LSD is chosen from a post-translational processing defect of lysosomal enzymes. Post-translational processing defects of lysosomal enzymes include, but are not limited to, mucosulphatidosis (MSD; multiple sulphatase defect), MLII (I-cell disease; N-acetyl glucosamine phosphoryl transferase defect) and MLIII (pseudo-Hurler polydystrophy; N-acetyl glucosamine phosphoryl transferase defect).

In one embodiment, the LSD is chosen from a trafficking defect for lysosomal enzymes. Trafficking defects for lysosomal enzymes include, but are not limited to, mucolipidosis type II (I-cell disease; N-acetyl glucosamine phosphoryl transferase defect), mucolipidosis type IDA (pseudo-Hurler polydystrophy; N-acetyl glucosamine phosphoryl transferase defect) and mucolipidosis type IIIC.

In one embodiment, the LSD is a defect in lysosomal enzyme protection. Defects in lysosomal enzyme protection include, but are not limited to, galactosialidosis (protective protein cathepsin A (PPCA) defect).

In one embodiment, the LSD is a defect in soluble non-enzymatic lysosomal proteins. Defects in soluble non-enzymatic lysosomal proteins include, but are not limited to, GM2 activator protein deficiency (variant AB), Niemann-Pick Disease Type C2 (NPC2), sphingolipid activator protein (SAP) deficiency.

In one embodiment, the LSD is a transmembrane (non-enzyme) protein defect. Transmembrane (non-enzyme) protein defects include, but are not limited to, Danon disease (lysosome-associated membrane protein 2 (LAMP2) defect), NPC (NPC1 defect), cystinosis (cystinosin defect), infantile free sialic acid storage disease (ISSD; sialin defect), Salla disease (free sialic acid storage; sialin defect), juvenile neuronal ceroid lipofuscinosis (CLN3, Batten disease), adult neuronal ceroid lipofuscinosis (Kufs disease; Adult NCL; palmotoyl-protein thioesterase-1 deficiency (Type A); Cathepsin F deficiency (Type B)), neuronal ceroid lipofuscinoses (NCL) (CLN6, CLN7, and CLN8) and mucolipidosis type IV (mucolipin defect). In one embodiment, the LSD is Niemann-Pick Type C1 or Niemann-Pick Type C2.

In one embodiment, the LSD is an unclassified defect. Unclassified defects include, but are not limited to, neuronal ceroid lipofuscinoses (NCL) (CLN5 and CLN9).

The LSD to be treated by the compositions and methods of the invention may be any of the neuronal ceroid lipofuscinoses, primary glycosphingolipidoses (i.e. Gaucher, Fabry, GM1, GM2 gangliosidoses, Krabbe and metachromatic leukodystrophy (MLD)), Farber disease and multiple sulphatase deficiency. In one embodiment, the LSD has a significant central nervous system (CNS) involvement. For example, the LSD may be chosen from NPC, Tay-Sachs disease, Sandhoff disease, GM1 gangliosidosis or Fabry disease.

In one embodiment, the LSD is Niemann-Pick disease type A. In another embodiment, the LSD is Niemann-Pick disease type B. In another embodiment, the LSD is Niemann-Pick type C (C1 or C2) disease. Niemann-Pick diseases are a heterogeneous group of autosomal recessive LSDs. Common cellular features include abnormal sphingomyelin (SM) storage in mononuclear phagocytic cells and parenchymal tissues, as well as (hepato)splenomegaly. Among the three main subgroups (A-C), NPC (previously classified as NPC and NPD and now appreciated to be a single disease) is classified as a fatal neurovisceral LSD caused by abnormal intracellular cholesterol transport-induced accumulation of unesterified cholesterol in late endosome/lysosomal compartments. Outside the CNS, the cellular characteristics of NPC include abnormal accumulation of unesterified cholesterol and other lipids (e.g. GSLs) within late endosome/lysosomal compartments. Conversely, there is no net elevation in cholesterol in the CNS (although it does have an altered distribution) but there are highly elevated levels of GSLs. Progressive neurodegeneration is particularly characterised by sequential degeneration of GABAergic Purkinje neurons in the cerebellum, which parallels the onset and progression of cerebellar ataxia and other aspects of neurological dysfunctions seen during the course of NPC. Genetic studies have shown that NPC disease is caused by mutations in either the Npc1 or Npc2 genes. The precise mechanistic link between these two genes remains unknown and the functional roles of these proteins remains enigmatic. NPC1 encodes a multimembrane spanning protein of the limiting membrane of the late endosome/lysosome, whereas NPC2 is a soluble cholesterol binding protein of the lysosome. When NPC1 is inactivated, sphingosine is the first lipid to be stored, suggesting that NPC1 plays a role in the transport of sphingosine from the lysosome, where it is normally generated as part of sphingolipid catabolism. Elevated sphingosine in turn causes a defect in calcium entry into acidic stores resulting in greatly reduced calcium release from this compartment. This then prevents late endosome-lysosome fusion, which is a calcium dependent process, and causes the secondary accumulation of lipids (cholesterol, sphingomyelin and glycosphingolipids) that are cargos in transit through the late endocytic pathway. Other secondary consequences of inhibiting NPC1 function include defective endocytosis and failure to clear autophagic vacuoles. It has been shown that the NPC1/NPC2 cellular pathway is targeted by pathogenic mycobacteria to promote their survival in late endosomes.

Tay-Sachs disease is a fatal hereditary disorder of lipid metabolism characterised especially in CNS tissue due to deficiency of the A isozyme of β-hexosaminidase. Mutations in the HEXA gene, which encodes the a subunit of β-hexosaminidase, cause the A isozyme deficiency. Tay-Sachs is a prototype of a group of disorders, the GM2 gangliosidoses, characterized by defective GM2 ganglioside degradation. The GM2 ganglioside (monosialylated ganglioside 2) accumulates in the neurons beginning already in fetal life.

Sandhoff disease results from a deficiency of both the A and B (basic) isozymes of β-hexosaminidase. Mutations in the HEXB gene, which encodes the β subunit of β-hexosaminidase, cause the B isozyme deficiency.

GM1 gangliosidosis is caused by a deficiency of β-galactosidase, which results in lysosomal storage of GM1 ganglioside (monosialylated ganglioside 1).

Fabry disease is caused by a deficiency of α-galactosidase, which results in lysosomal storage of a ceramide trihexoside.

In one embodiment, the LSD is chosen from Tay-Sachs disease, the AB variant of Tay-Sachs disease, Sandhoff disease, Niemann Pick type A disease, mucolipidosis II, mucolipidosis III, MPS III, MPS VII, GM1 gangliosidosis, and aspartylglucosaminuria. In one embodiment, the LSD is Sandhoff disease. In one embodiment, the LSD is Tay-Sachs disease. In one embodiment, the LSD is the AB variant of Tay-Sachs disease. In one embodiment, the LSD is mucolipidosis type II. In one embodiment, the LSD is mucolipidosis type III. In one embodiment, the LSD is GM1 gangliosidosis. In one embodiment, the LSD is MPS III. In one embodiment, the LSD is MPS VII. In one embodiment the LSD is Niemann Pick type A disease. In one embodiment, the LSD is aspartylglucosaminuria.

In one embodiment, the LSD is not Niemann-Pick disease. In one embodiment, the LSD is not Niemann-Pick type C disease.

In one embodiment, the acetyl-leucine, or a pharmaceutically acceptable salt thereof, treats weight loss, gait deterioration, and/or motor function deterioration associated with Niemann-Pick disease (e.g., Niemann-Pick type C or A) or mucolipidosis type II. For example, the acetyl-leucine, or a pharmaceutically acceptable salt thereof, may delay onset of, reduce the severity of or eliminate, or delay or reverse the progression of weight loss, gait deterioration, and/or motor function deterioration associated with Niemann-Pick disease (e.g. Niemann-Pick type C or A) or mucolipidosis type II. In one embodiment, the weight loss, gait deterioration, and/or motor function deterioration is associated with Niemann-Pick type A or mucolipidosis type II.

In one embodiment, the acetyl-leucine, or a pharmaceutically acceptable salt thereof, treats gait deterioration, motor function deterioration, and/or reduced mobility associated with Sandhoff's disease. For example, the acetyl-leucine, or a pharmaceutically acceptable salt thereof, may delay onset of, reduce the severity of or eliminate, or delay or reverse the progression of gait deterioration, motor function deterioration, and/or reduced mobility associated with Sandhoff's disease.

In one embodiment, the acetyl-leucine, or a pharmaceutically acceptable salt thereof treats reduced co-ordination, tremors, reduced mobility, cognitive impairment, and/or gait deterioration associated with Tay-Sachs disease. For example, the acetyl-leucine, or a pharmaceutically acceptable salt thereof, may delay onset of, reduce the severity of or eliminate, or delay or reverse the progression of reduced co-ordination, tremors, reduced mobility, cognitive impairment, and/or gait deterioration associated with Tay-Sachs disease.

There is also provided a method of treating a LSD or one or more symptoms of a LSD in a subject in need thereof, the method comprising administering a therapeutically effective amount of acetyl-leucine, or a pharmaceutically acceptable salt thereof, to the subject.

A "therapeutically effective amount" of an agent is any amount which, when administered to a subject, is the amount of agent that is needed to produce the desired effect, which, for present disclosure, can be therapeutic and/or prophylactic. The dose may be determined according to various parameters, such as the specific form of acetyl-leucine used; the age, weight and condition of the patient to be treated; the type of the disease; the route of administration; and the required regimen. A physician will be able to determine the required route of administration and dosage for any particular patient. For example, a daily dose may be from about 10 to about 225 mg per kg, from about 10 to about 150 mg per kg, or from about 10 to about 100 mg per kg of body weight.

Also disclosed is a kit for treating a LSD in a subject in need thereof (e.g., a subject having, suspected of having, or at risk of having a LSD), comprising a means for diagnosing or prognosing a LSD, and acetyl-leucine or a pharmaceutically acceptable salt thereof.

The means for diagnosing or prognosing a LSD may include a specific binding agent, probe, primer, pair or combination of primers, an enzyme or antibody, including an antibody fragment, which is capable of detecting or aiding in the detection of a LSD, as defined herein. The kit may comprise LysoTracker®, which is a fluorescent marker and is commercially-available from both Invitrogen and also Lonza. The LysoTracker® may be blue, blue-white, yellow, green or red.

The kit also comprises acetyl-leucine or a pharmaceutically acceptable salt thereof, as defined herein. The kit may further comprise buffers or aqueous solutions. The kit may further comprise instructions for using the acetyl-leucine or a pharmaceutically acceptable salt thereof in a method of the invention.

In a further embodiment, there is disclosed acetyl-leucine, or a pharmaceutically acceptable salt thereof, for use in a method of providing neuroprotection in a subject having, suspected of having, or at risk of having a LSD.

"Neuroprotection" and its cognates, as used herein, refer to prevention, a slowing in, and/or a reversed progression of neurodegeneration, including, but not limited to, progressive loss of neuronal structure, progressive loss of neuronal function, and/or progressive neuronal death. Providing neuroprotection may result in delaying onset of a LSD or one or more symptoms of a LSD that would otherwise be expected to manifest according to typical disease progression, reducing the severity of a LSD or reducing the severity of or eliminating one or more existing symptoms associated with a LSD, delaying progression of a LSD or one or more symptoms of a LSD over time as compared to typical disease progression, and/or reversing progression of a LSD or one or more symptoms of a LSD over time. The time over which neuroprotection is provided may coincide with the duration of treatment as described herein. The treatment may provide neuroprotection over a duration of, for example, about seven days or more, about two weeks or more, about three weeks or more, about one month or more, about six weeks or more, about seven weeks or more or about two months or more. Further for example, the treatment provides neuroprotection over a duration of about three months or more, about four months or more, about five months or more or about six months or more. In another embodiment, it provides neuroprotection over a duration of about 1 year or more, about 2 years or more, about 3 years or more, about 4 years or more, about 5 years or more, or about 10 years or more. The treatment may provide neuroprotection over the lifetime of the patient.

As evidenced by the Examples, the inventors believe that acetyl-leucine is acting as a neuroprotective agent and so inhibiting the neurodegeneration that would otherwise be expected to manifest.

In one embodiment, there is a method of providing neuroprotection in a subject having, suspected of having, or at risk of having a LSD, the method comprising administering a therapeutically effective amount of acetyl-leucine, or a pharmaceutically acceptable salt thereof, to the subject.

Also disclosed is a kit for providing neuroprotection in a subject having, suspected of having, or at risk of having a LSD, the kit comprising a means for diagnosing or prognosing a LSD, and acetyl-leucine or a pharmaceutically acceptable salt thereof.

The present disclosure further includes the use of acetyl-leucine, or a pharmaceutically acceptable salt thereof, as a neuroprotective agent in a subject having, suspected of having, or at risk of having a LSD.

All of the features described herein (including any accompanying claims, abstract and drawings), and/or all of the steps of any method so disclosed, may be combined with any of the above aspects in any combination, except combinations where at least some of such features and/or steps are mutually exclusive.

EXAMPLES

The invention will now be explained in further detail in the following Examples, which demonstrate the utility of acetyl-leucine in treating a LSD in a subject and providing neuroprotection in said subject.

Example 1

In Vivo Mouse Study—Methods
Mouse Model

This study made use of an authentic mouse model of NPC, the Npc1$^{-/-}$ (BALB/cNctr-Npc1$^{m1N}$/J) mouse, which is null for the NPC1 protein and displays all the hallmarks of the clinical disease (Loftus, 1997).

This mutant strain arose spontaneously and has a lifespan in the range of 10-14 weeks and therefore has a course of disease more acute that the vast majority of patients. The mutant mouse has been exploited successfully, not only for determining the ontogeny of disease and underlying pathogenic mechanisms, but also for the evaluation of experimental therapies. Analyses using these mice have been undertaken at the whole animal, cellular, and molecular levels (Baudry, 2003; Smith, 2009; Cologna, 2014; Cologna, 2012). It is the most intensively studied animal model of NPC.

Prior to about 4-5 weeks of age $Npc1^{-/-}$ mice have no discernible behavioural indication of disease that distinguishes them from wild-type littermates. First indications of behavioural deficits, such as tremor and ataxic gait, appear by weeks 5-6; by weeks 7-8 defects in motor coordination become more apparent, and by 9-10 weeks ataxia is advanced and accompanied by increased loss in weight and poor coat condition as feeding and drinking becomes difficult (humane end point applied) (Smith, 2009).

Wild-type ($Npc1^{+/+}$) littermates were used as a control.

Treatment Protocol

A group of $Npc1^{-/-}$ mice and a group of $Npc1^{+/+}$ mice were treated with 0.1 g/kg acetyl-DL-leucine, provided mixed in the mouse chow, from weaning (three weeks of age). Separate groups of $Npc1^{-/-}$ and $Npc1^{+/+}$ mice were left untreated, as controls.

Coat Condition

The coat condition of $Npc1^{-/-}$ mice, with and without acetyl-DL-leucine treatment, was compared by simple observation of the mice at nine weeks of age.

Weight Data

Animals were weighed twice a week. Weights were averaged (mean) across all mice in each group and compared.

Gait Analysis

Gait analysis was performed on mice at eight weeks of age using a CatWalk® 15.0 system according to manufacturer's instructions (Noldus, Nottingham, UK). Five runs were recorded per animal.

CatWalk® parameters measured were:
1. Stand Mean: average duration (s) of paws in contact with glass plate;
2. Step Cycle: duration (s) between two consecutive contacts of the same paw;
3. Duty Cycle: percentage of time paws in contact with plate compared with time to complete a step cycle;
4. Step Sequence (AB): percentage of time spent walking in LF-RH-RF-LH alternating pattern (LF: left front; RH: right hind; RF: right front; LH left hind);
5. Cadence: step per seconds in a trial;
6. Diagonal Support: percentage of time with simultaneous contact of diagonal paws with the glass plate (RF&LH or RH&LF).

Motor Function Analysis

Motor function analysis was performed on mice at eight and nine weeks of age using an Open Field Activity Monitor according to manufacturer's instructions (Linton Instruments, Amlogger Software). Each mouse was placed in a plastic cage with bedding and analysed for five minutes. Rears were counted manually.

Motor function parameters measured were:
1. Centre Rearing: mice rearing on hind legs unsupported;
2. Rearing: mice rearing on hind legs with and without the support of cage walls;
3. Activity: regular movement of the animal including walks;
4. Front to Back (FR) count: movement of the animal from front to back of the cage;
5. Active Time: duration (s/min) of activeness regardless of movement;
6. Mobile Time: duration (s/min) of mobility;
7. Rearing Time: duration of any rearing.

Results

Coat Condition

Figure 1B:

FIG. 1 B shows an untreated $Npc1^{-/-}$ age matched littermate. $Npc1^{-/-}$ mice were observed as having poor coat condition at nine weeks of age, as feeding and drinking had become difficult (see FIG. 1B).

In distinct contrast, FIG. 1A shows an $Npc1^{-/-}$ mouse treated with acetyl-DL-leucine from weaning. $Npc1^{-/-}$ mice treated with acetyl-DL-leucine had a smooth and glossy coat, reminiscent of wild-type ($Npc1^{+/+}$) littermates (see FIG. 1A).

Weight Data

Figure 2A:
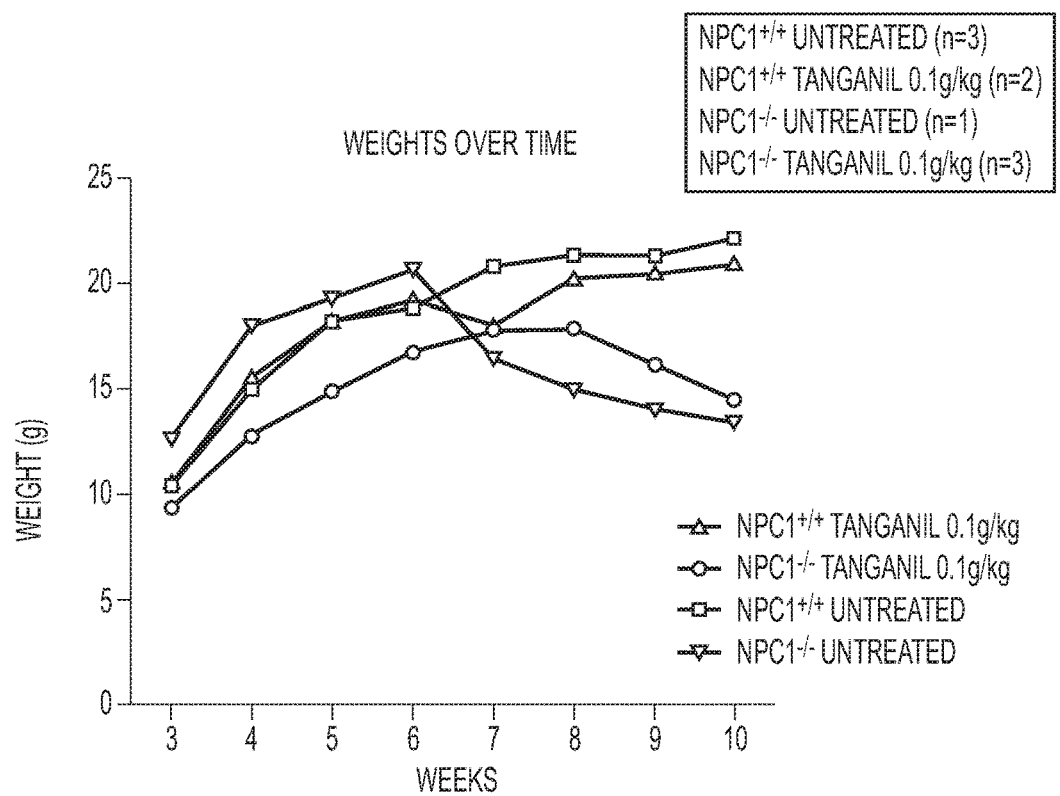
FIGS. 2A and 2B show weight data for Npc1$^{-/-}$ mice compared to wild-type (Npc1$^{+/+}$) mice, with and without acetyl-DL-leucine treatment from weaning.

As can be seen in FIG. 2A, wild-type ($Npc1^{+/+}$) mice progressively put on weight for the duration of the study, i.e. from three weeks to 10 weeks of age. Further, FIG. 2A shows the mean weight per group of mice at each point in time ($Npc1^{-/-}$ untreated, n=1; $Npc1^{-/-}$ acetyl-DL-leucine 0.1 g/kg, n=3; $Npc1^{+/+}$ untreated, n=3; $Npc1^{+/+}$ acetyl-DL-leucine 0.1 g/kg, n=2).

Treatment with acetyl-DL-leucine had no significant effect on this weight gain.

$Npc1^{-/-}$ mice initially put on weight, largely in the same manner as $Npc1^{+/+}$ controls. However, the $Npc1^{-/-}$ mice then began to lose weight from six weeks of age. At the end of the study (10 weeks of age), the mice weighed nearly as little as at just four weeks of age.

Treatment with acetyl-DL-leucine delayed these weight loss symptoms by two weeks compared to the untreated group.

Figure 2B:
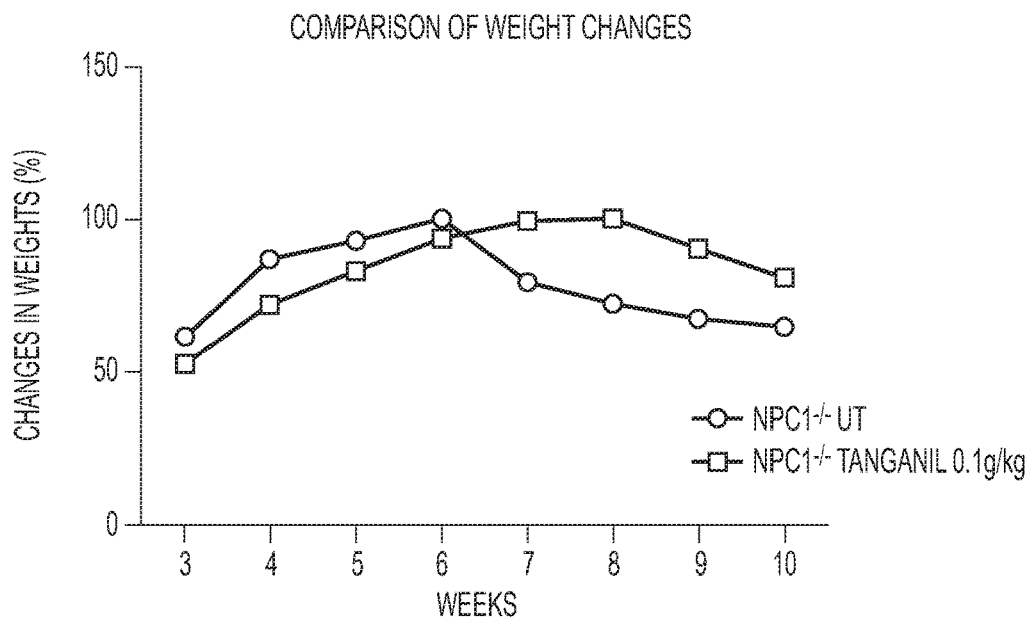

A comparison of the weight changes in $Npc1^{-/-}$ mice, with and without acetyl-DL-leucine treatment, is shown in FIG. 2B. In particular, FIG. 2 B shows the change in weight (%) per group of mice at each point in time, for the $Npc1^{-/-}$ mice only. The beneficial effect of acetyl-DL-leucine treatment in delaying weight loss is clearly evident from this Figure.

Gait Analysis

Figures 3C, 3D:
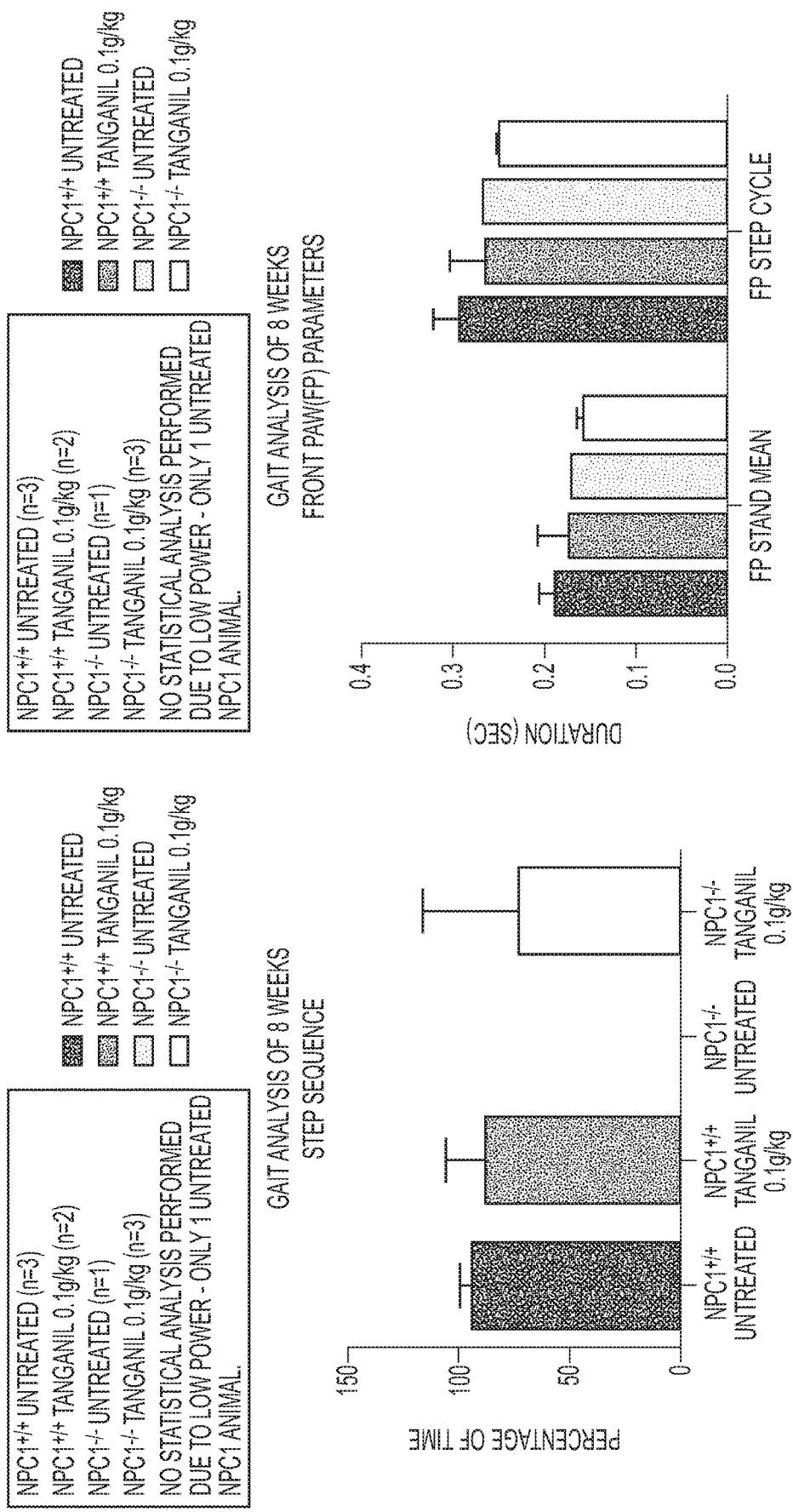
Figure 4A:
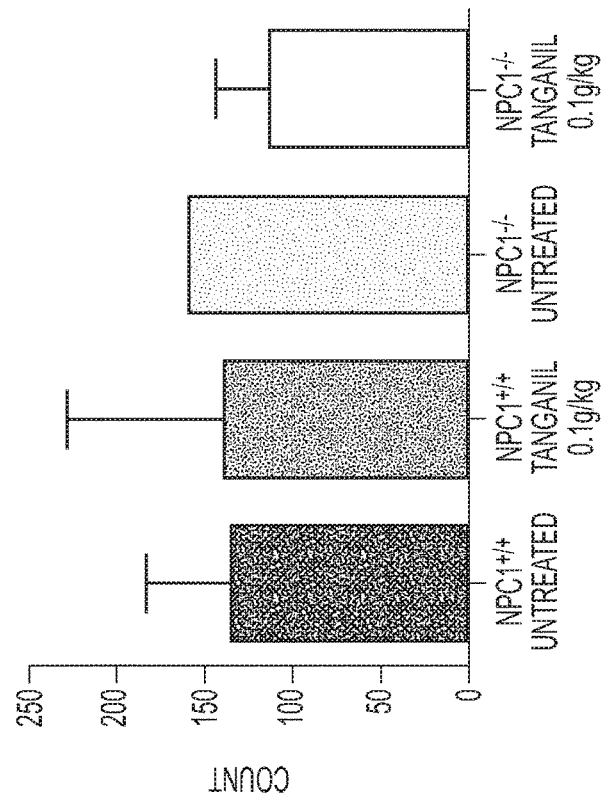
FIGS. 4A-4H show motor function analysis data for Npc1$^{-/-}$ mice compared to wild-type (Npc1$^{+/+}$) mice, with and without acetyl-DL-leucine treatment from weaning. Centre rearing, activity, rearing and front to back (FR) count are shown in FIGS. 4A-4D, respectively. Active time, mobile time, rearing time and total manual rearing count are shown in FIGS. 4E-4H, respectively.
Figure 4B:
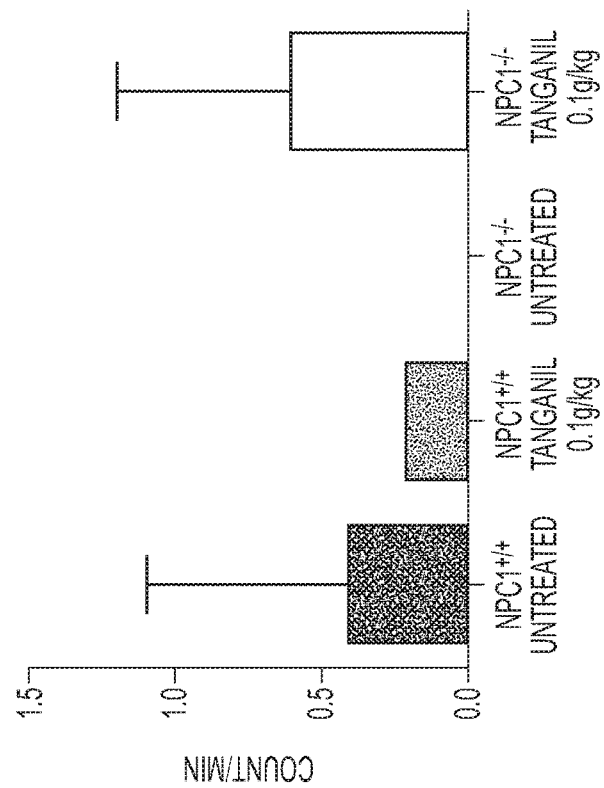
Figure 4C:
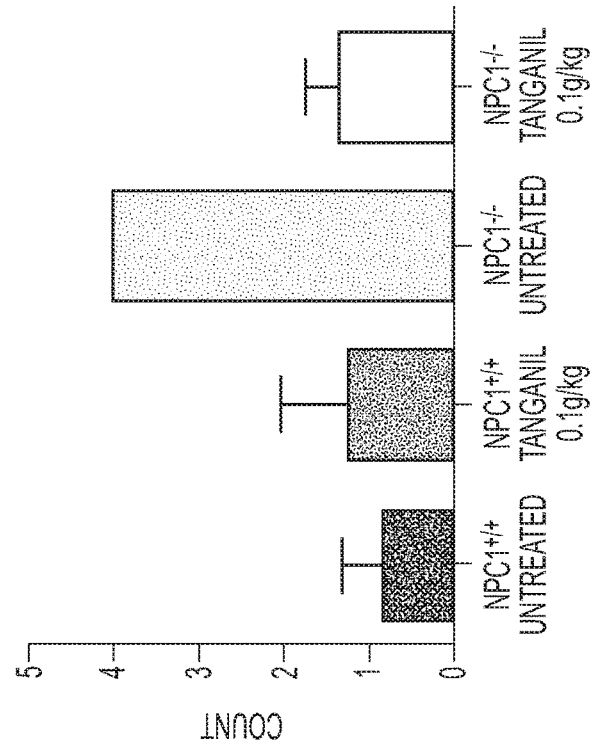
Figure 4D:
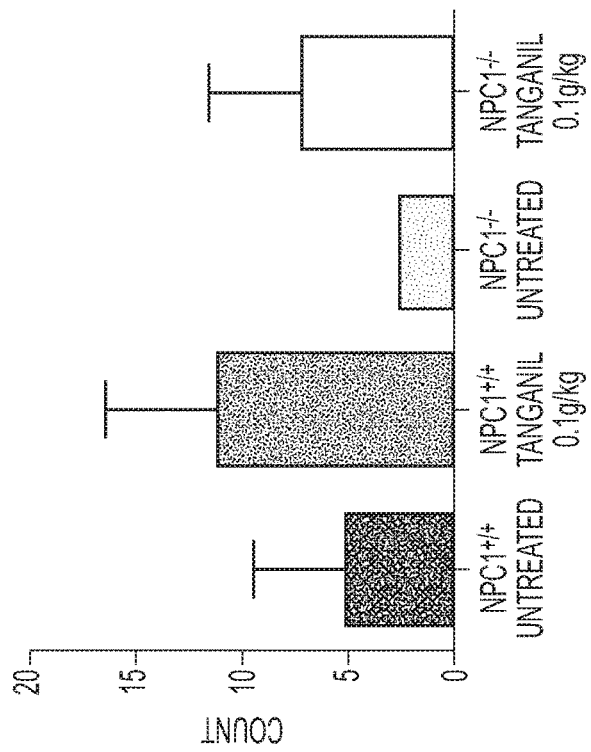
Figure 4F:
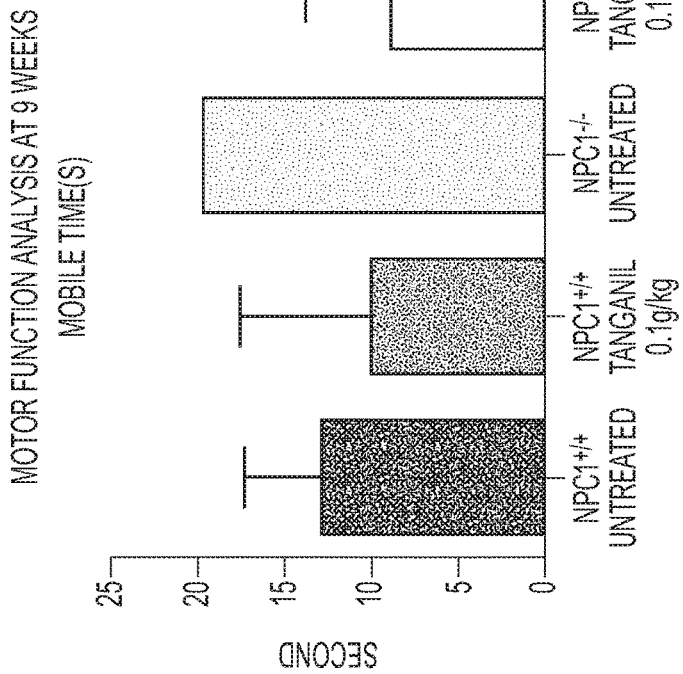
Figure 4E:
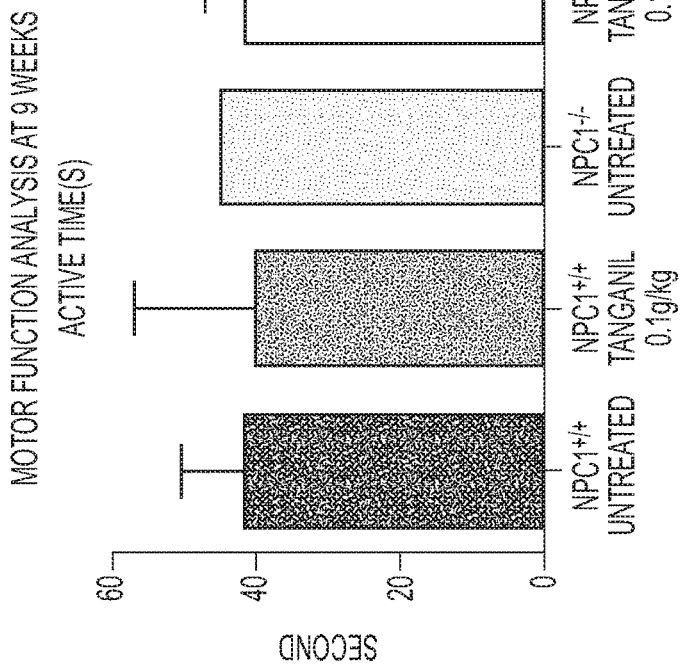
Figure 4G:
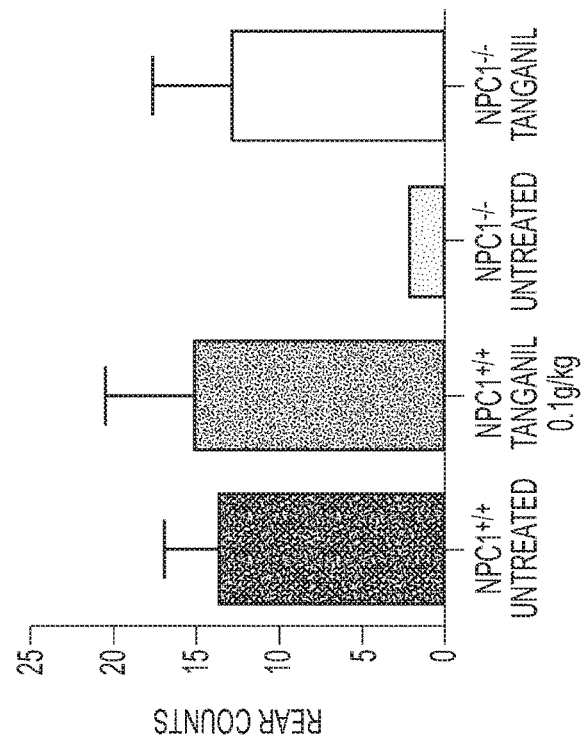
Figure 4H:
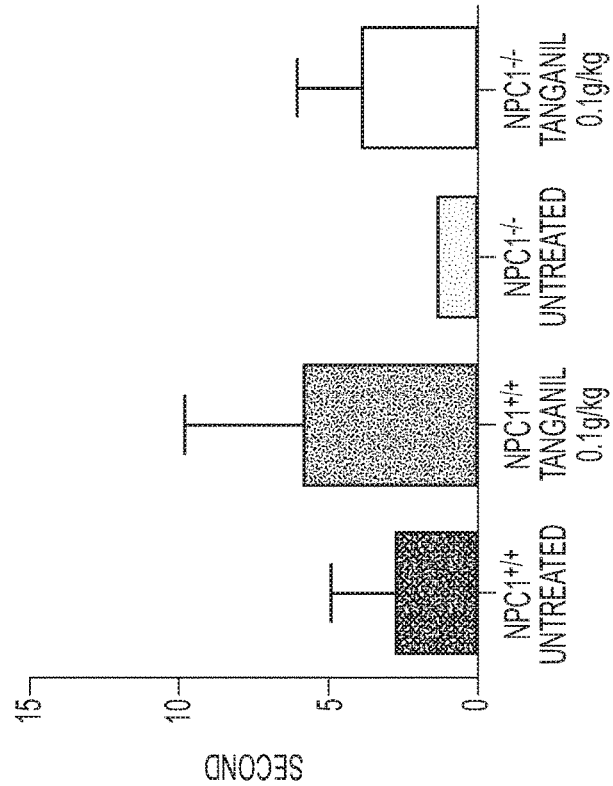

The results of the gait analysis are shown in FIG. 3. Diagonal support, cadence and step sequence data are shown in FIGS. 3A-3C, respectively. FIGS. 3D and 3E show front paw (FP) data (stand mean and step cycle in FIG. 3D; duty cycle in FIG. 3E). FIGS. 3F and 3G show hind paw (HP) data (stand mean and step cycle in FIG. 3F; duty cycle in FIG. 3G). Data are presented as mean±SEM. n=3 for $Npc1^{+/+}$ untreated, n=2 for $Npc1^{+/+}$ treated, n=1 for $Npc1^{-/-}$ untreated (hence no statistical analysis performed), n=3 for $Npc1^{-/-}$ treated.

The first bar in each graph shows the gait properties of wild-type ($Npc1^{+/+}$) mice.

The second bar in each graph shows the gait properties of wild-type ($Npc1^{+/+}$) mice treated with acetyl-DL-leucine. There was no significant difference in gait properties between these mice and their untreated littermates.

The third bar in each graph shows the gait properties of an $Npc1^{-/-}$ mouse. On the whole, this mouse showed poor gait compared to $Npc1^{+/+}$ mice. The mouse spent extremely little time, if any, in diagonal support (FIG. 3A) or step sequence (FIG. 3C), and its hind paw function in stand mean (FIG. 3F) and duty cycle (FIG. 3G) were also drastically hindered.

The fourth bar in each graph shows the gait properties of $Npc1^{-/-}$ mice treated with acetyl-DL-leucine. These mice demonstrated significantly improved gait compared to their untreated littermates. In fact, they showed similar gait properties to Npc1$^{+/+}$ mice.

Motor Function Analysis

Analysis at eight weeks of age revealed no difference in motor function properties between Npc1$^{-/-}$ and wild-type (Npc1$^{+/+}$) mice (data not shown).

By nine weeks of age, however, defects in motor coordination had become apparent.

The results of the motor function analysis at nine weeks are shown in FIG. 4. Centre rearing, activity, rearing and front to back (FR) count are shown in FIGS. 4A-4D, respectively. Active time, mobile time, rearing time and total manual rearing count are shown in FIGS. 4E-4H, respectively. Data are presented as mean±SEM. n=3 for Npc1$^{+/+}$ untreated, n=2 for Npc1$^{+/+}$ treated, n=1 for Npc1$^{-/-}$ untreated (hence no statistical analysis performed), n=3 for Npc1$^{-/-}$ treated.

The first bar in each graph shows the motor function properties of wild-type (Npc1$^{+/+}$) mice.

The second bar in each graph shows the motor function properties of wild-type (Npc1$^{+/+}$) mice treated with acetyl-DL-leucine. There was no significant difference in motor function properties between these mice and their untreated littermates.

The third bar in each graph shows the motor function properties of an Npc1$^{-/-}$ mouse. On the whole, this mouse showed poor motor function compared to Npc1$^{+/+}$ mice. The mouse spent extremely little time, if any, rearing (panel H), particularly on its hind legs unsupported (panel A).

The fourth bar in each graph shows the motor function properties of Npc1$^{-/-}$ mice treated with acetyl-DL-leucine. These mice demonstrated significantly improved motor function compared to their untreated littermates. In fact, they showed similar motor function properties to Npc1$^{+/+}$ mice.

Lifespan

Figure 5:
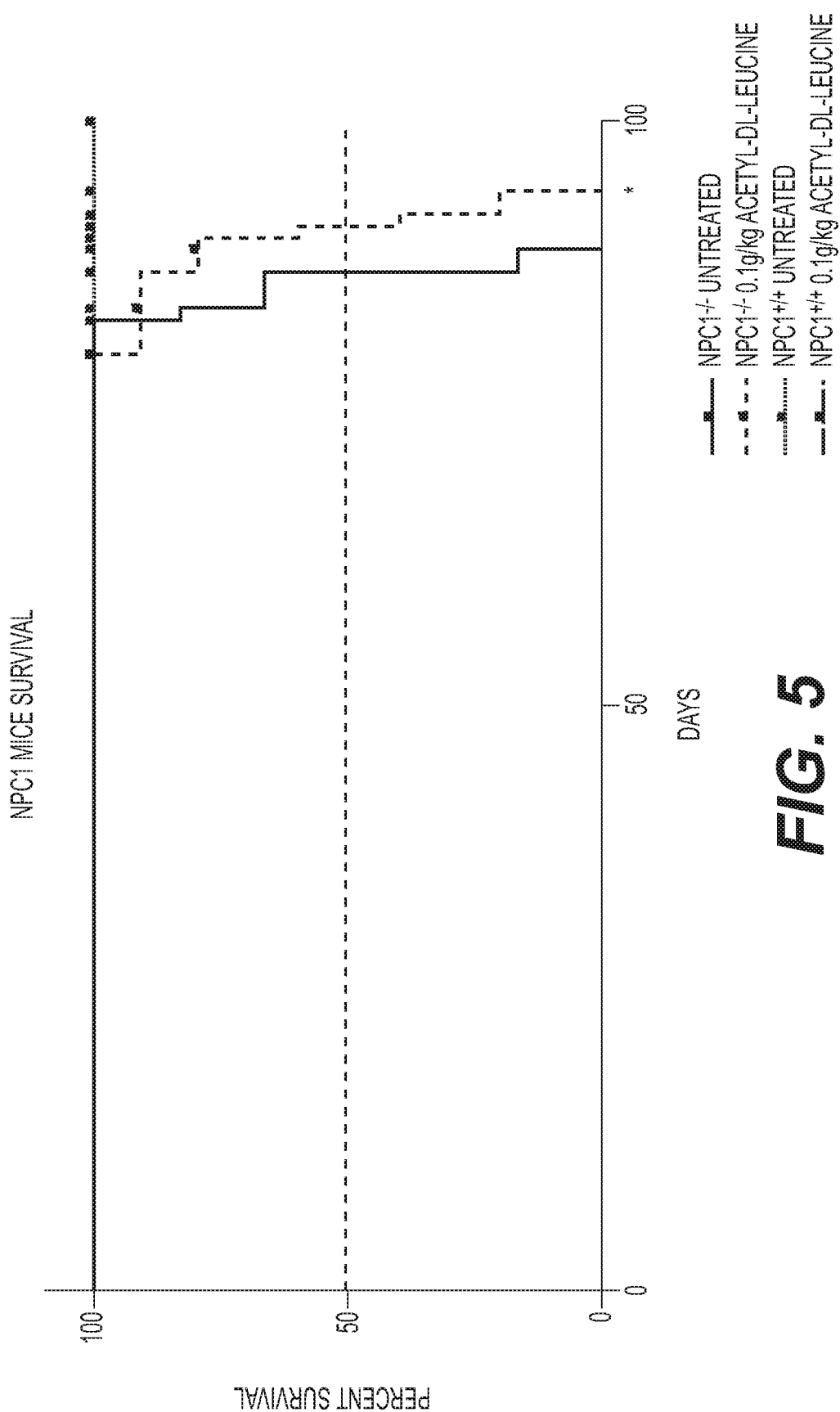
FIG. 5 shows that treatment with acetyl-DL-leucine (0.1 g/kg from 3 weeks of age) is associated with a small but statistically significant increase in lifespan in the Npc1$^{-/-}$ mouse.

It was also observed that treatment of the Npc1$^{-/-}$ mouse with acetyl-DL-leucine (0.1 g/kg from 3 weeks of age) is associated with a statistically significant increase in lifespan (FIG. 5). This data further indicates the effect of acetyl-leucine in delaying the onset of the disease.

Conclusion

Where Npc1$^{-/-}$ mice had discernible indication of disease that distinguished them from wild-type littermates from 5-6 weeks of age, Npc1$^{-/-}$ littermates treated with acetyl-DL-leucine from weaning did not display such symptoms until two or more weeks later. Treatment of Npc1$^{-/-}$ mice with acetyl-DL-leucine delayed onset and progression of NPC symptoms and showed evidence of neuroprotection.

Example 2

Methods

A fibroblast cell line from an NPC patient was treated for 3 days with N-acetyl-DL-leucine (1 mM) and relative lysosomal volume was quantified via LysoTracker, a fluorescent dye that accumulates in acidic organelles. Increased LysoTracker fluorescence is indicative of an increase in lysosomal size and/or number, and is a hallmark of NPC cells.

In addition, fibroblasts derived from Niemann-Pick A (NPA), Mucolipidosis Type II (MLII), Mucopolysaccharidosis Type IIIB (MPS IIIB), Aspartylglucosaminuria, Mucolipidosis Type IIIA (MLIIIA), and Mucopolysaccharidosis Type VII (MPS VII) patients were treated with acetyl-DL-leucine (i mM) for 6 days and lysosomal volume was quantified via LysoTracker.

Results

Figure 6A:
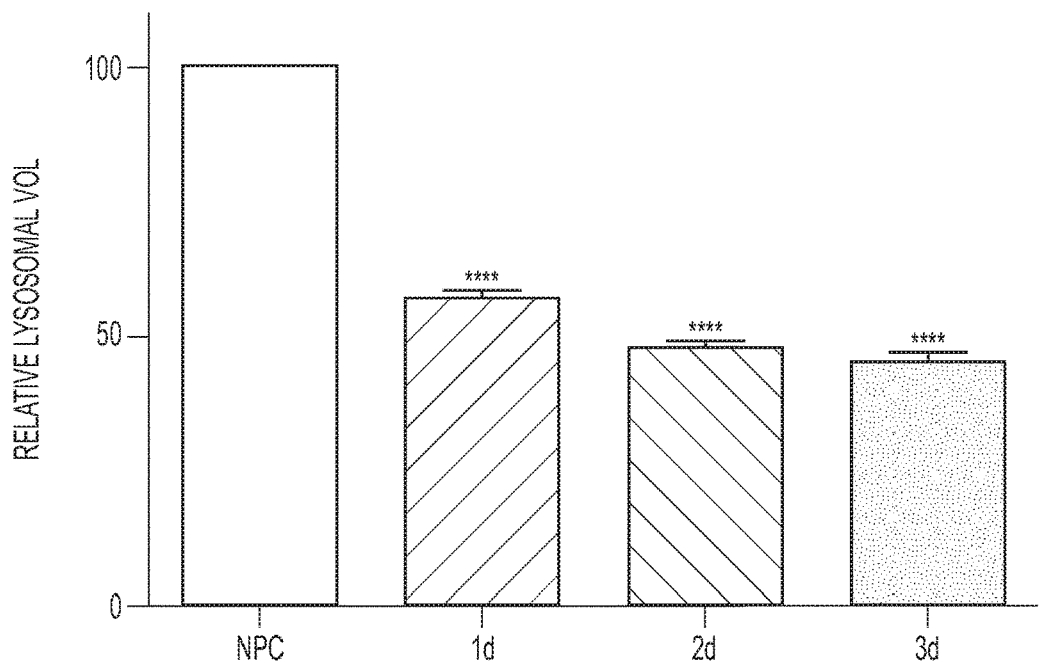
FIGS. 6A and 6B shows the reduction of lysosomal volume in non-neuronal NPC cells following treatment with acetyl-DL-leucine.
Figure 6B:
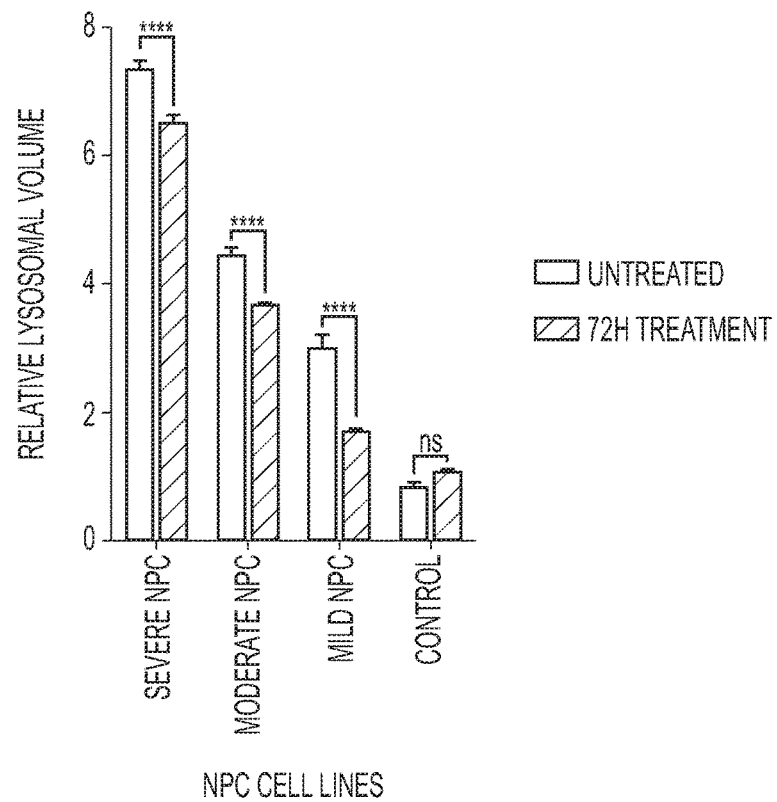
Figure 6C:
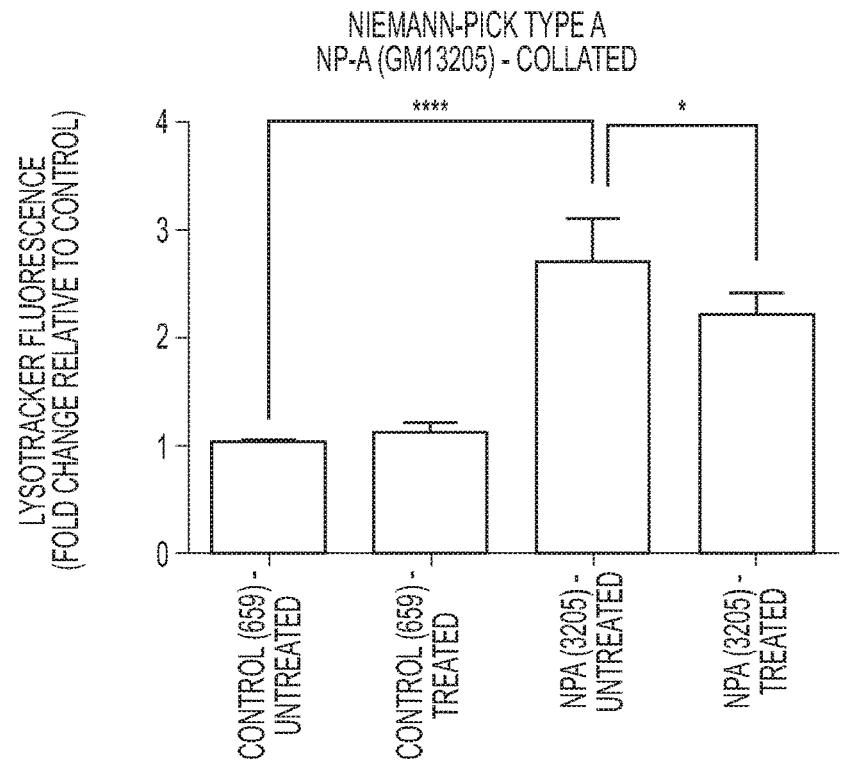
FIGS. 6C-6H show the effect of treatment with acetyl-DL-Leucine on lysosomal volume in NPA, MLII, MPS IIIB, Aspartylglucosaminuria, MLIIIA, and MPS VII patient fibroblasts, respectively.
Figure 6D:
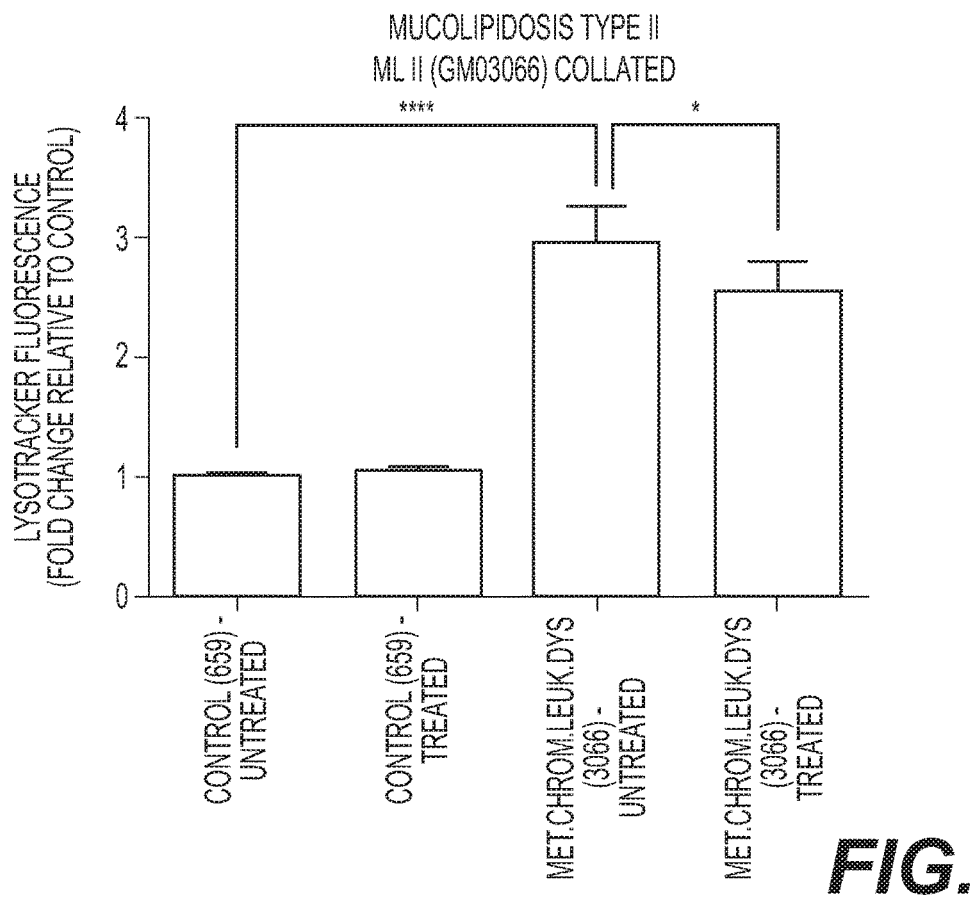
Figure 6E:
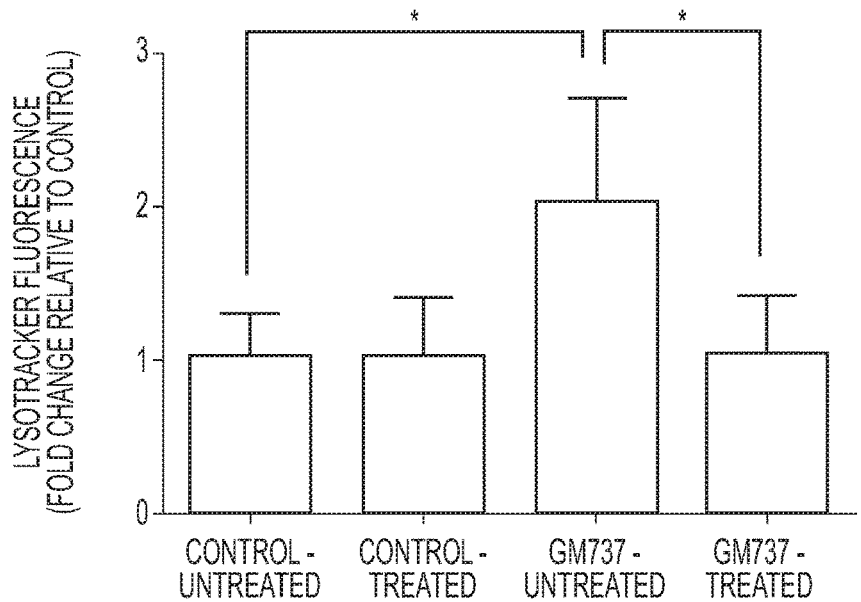

Treatment of fibroblasts derived from an NPC patient of mild clinical severity with 1 mM N-acetyl-DL-leucine was associated with a significant decrease in LysoTracker fluorescence, indicative of reduced lysosomal volume over time (FIG. 6A). These findings were replicated in fibroblasts obtained from additional NPC patients of variable clinical severity that were treated with 1 mM N-acetyl-DL-leucine for 72 hours (FIG. 6B).

Figure 6F:
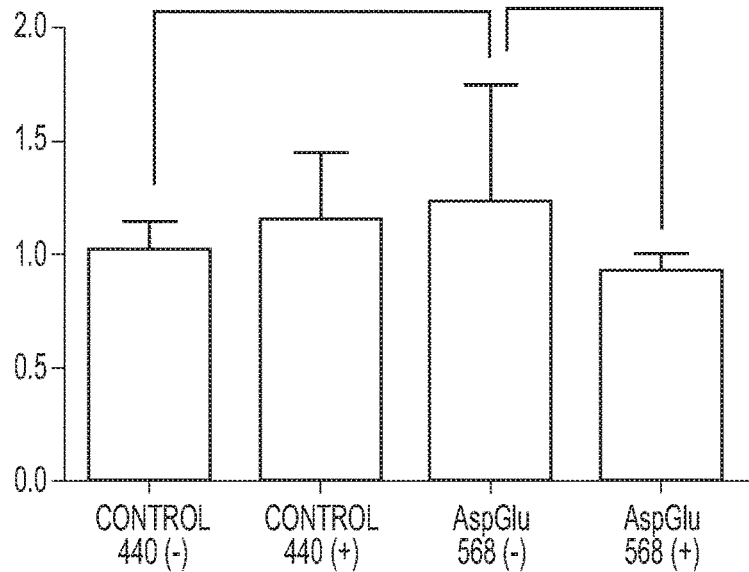
Figure 6G:
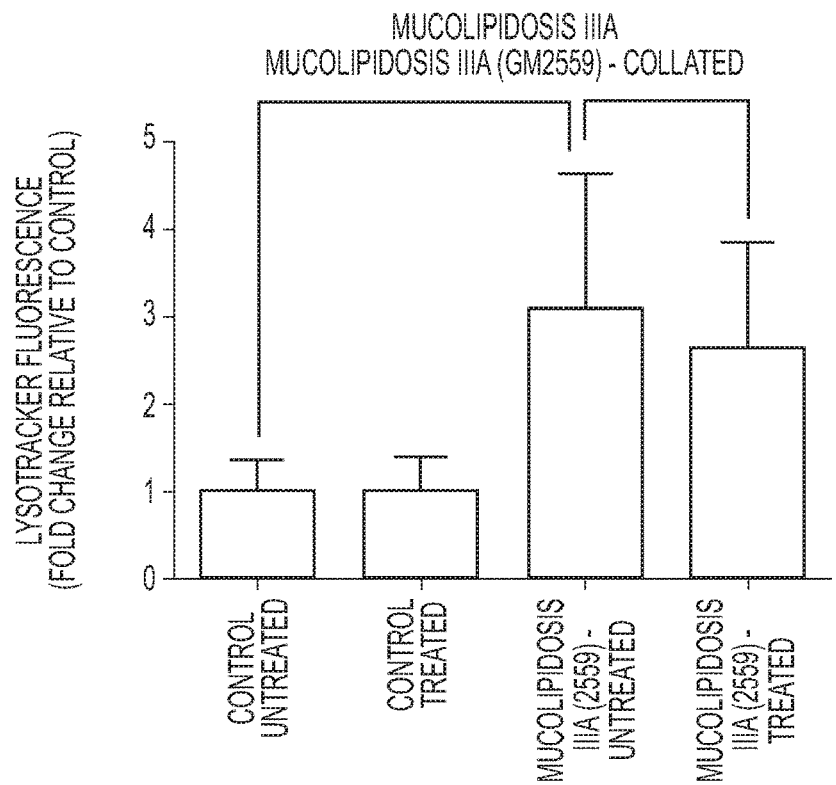
Figure 6H:
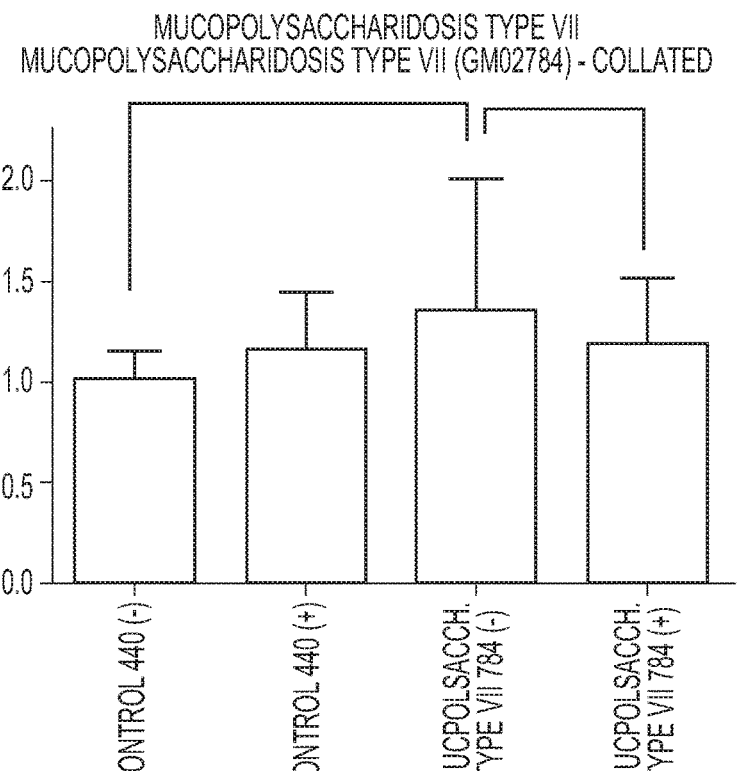

Fibroblasts derived from NPA, MLII, MPS IIIB, Aspartylglucosaminuria, MLIIIA, and MPS VII patients were observed to have elevated LysoTracker fluorescence levels relative to age-matched wild-type controls (FIGS. 6C-6H). This is indicative of an expanded lysosome occurring as a result of lipid storage compared to fibroblasts from healthy individuals. Treatment with acetyl-leucine was associated with a statistically significant reduction in LysoTracker fluorescence toward control level in the NPA, MLII, and MPS IIIB fibroblasts relative to untreated NPA, MLII, and MPS IIIB fibroblasts, respectively (FIGS. 6C-6E), and was associated with a trend in reducing LysoTracker fluorescence toward control level in the aspartylglucosaminuria, MLIIIA, and MPS VII fibroblasts relative to untreated aspartylglucosaminuria, MLIIIA, and MPS VII fibroblasts, respectively (FIGS. 6F-6H). The reduction in LysoTracker fluorescence was indicative of a decrease in lysosomal volume (FIGS. 6C-6H). Data presented in FIGS. 6A-6D show the results of the treatment for each cell line, respectively, with lysosomal volume expressed as fold change relative to untreated wild-type fibroblasts. The asterisks (*/****) indicate p-values of (<0.05/0.001) versus untreated disease fibroblasts.

Conclusion

N-acetyl-DL-leucine treatment was associated with the rectification of disturbed lysosomal storage by reducing lysosomal volume and thus directly corrected a phenotype of these lysosomal storage disorders. These diseases represent different classes of LSDs, and thus these results further support utility of acetyl-leucine's effect against a broad range of lysosomal storage disorders.

Example 3

Sandhoff disease is a disorder which may result from the autosomal recessive inheritance of mutations in the HEXB gene, which encodes the beta-subunit of beta-hexosaminidase. As a result of this, GM2 ganglioside fails to be degraded and accumulates within lysosomes in cells of the periphery and the central nervous system (CNS).

This study made use of a mouse model of Sandhoff disease, the Hexb$^{-/-}$ mouse, as described in Jeyakumar et al. (Jeyakumar, M. et al. (1999) Proc. Natl. Acad. Sci. USA 96: 6388-6393).

Wild-type (Hexb$^{+/+}$) mice were used as controls.

Lifespan

Figure 7A:
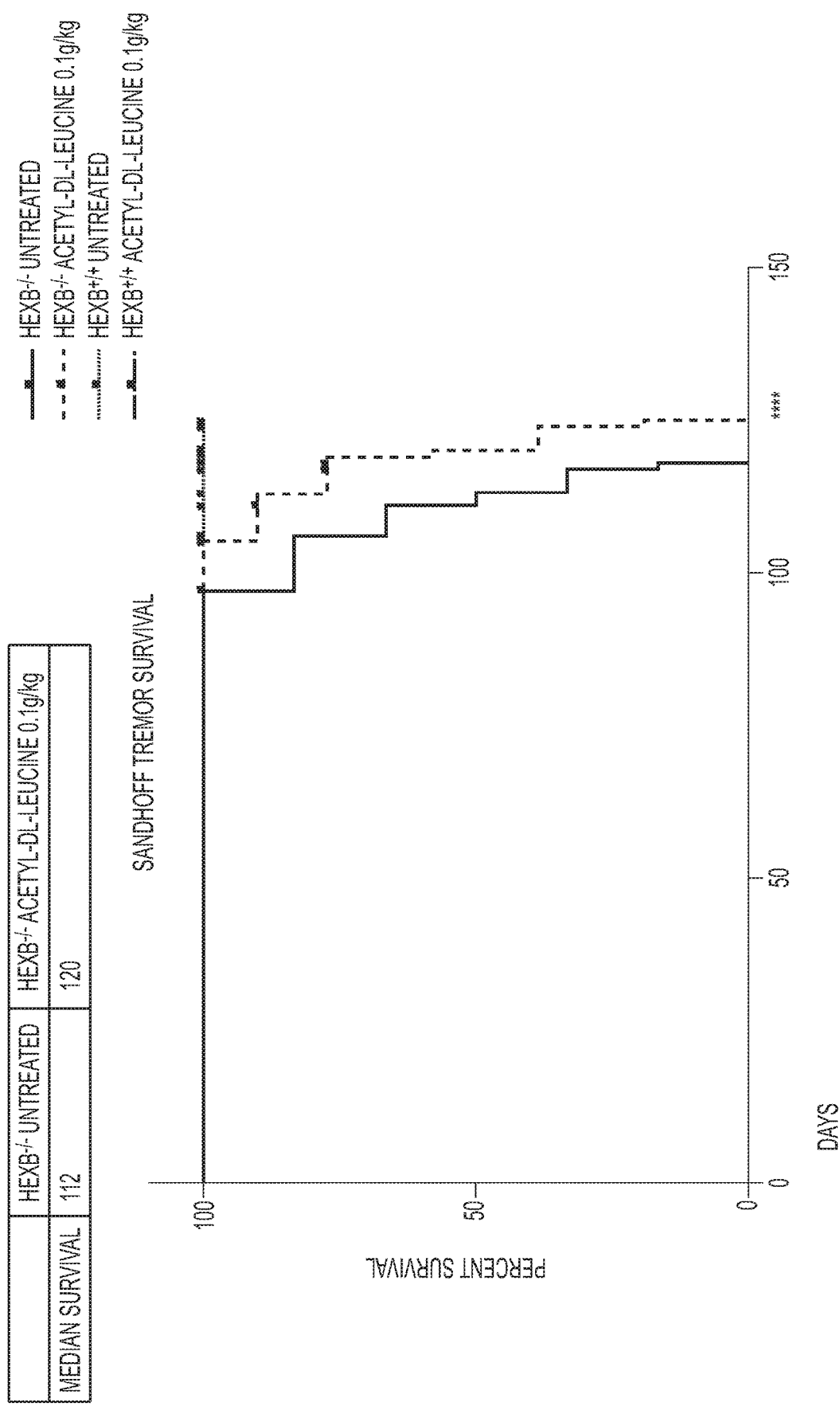
FIG. 7A shows a survival curve representing mortality in untreated or acetyl-leucine-treated wild-type and Sandhoff mice.

Treatment with acetyl-DL-Leucine was associated with a statistically significant increase in the lifespan of the Sandhoff mouse (FIG. 7A). In FIG. 7A, acetyl-leucine-treated mice were treated with 0.1 g/kg acetyl-leucine from 3 weeks of age. The asterisks (*) indicates a p-value of <0.05 vs untreated Sandhoff mice. Data is average of n=6 mice per group. Without treatment, the median survival time of Sandhoff mice was 112 days. Treatment with acetyl-leucine (0.1 g/kg body weight since 3 weeks of age) increased the median lifespan to 120 days.

Motor Function

Treatment of Sandhoff mice with acetyl-leucine gave rise to improvements in motor function as indicated by bar crossing and step cycle studies.

Bar Crossing Test

The bar crossing test is a method for assessing motor function in mice in which the mouse is placed hanging from the centre of a horizontal bar by its front limbs. A wild-type mouse with normal motor function will be able to engage its hind limbs and thereby move to one of the platforms at either end of the bar, and in doing so complete the test.

An untreated Sandhoff mouse is able to complete the test up until around 11 weeks of age. After this point motor function and hind-limb mobility/engagement have deteriorated to the point to which the mouse cannot complete the test, and will drop from the bar onto the padded surface below.

Figure 7B:
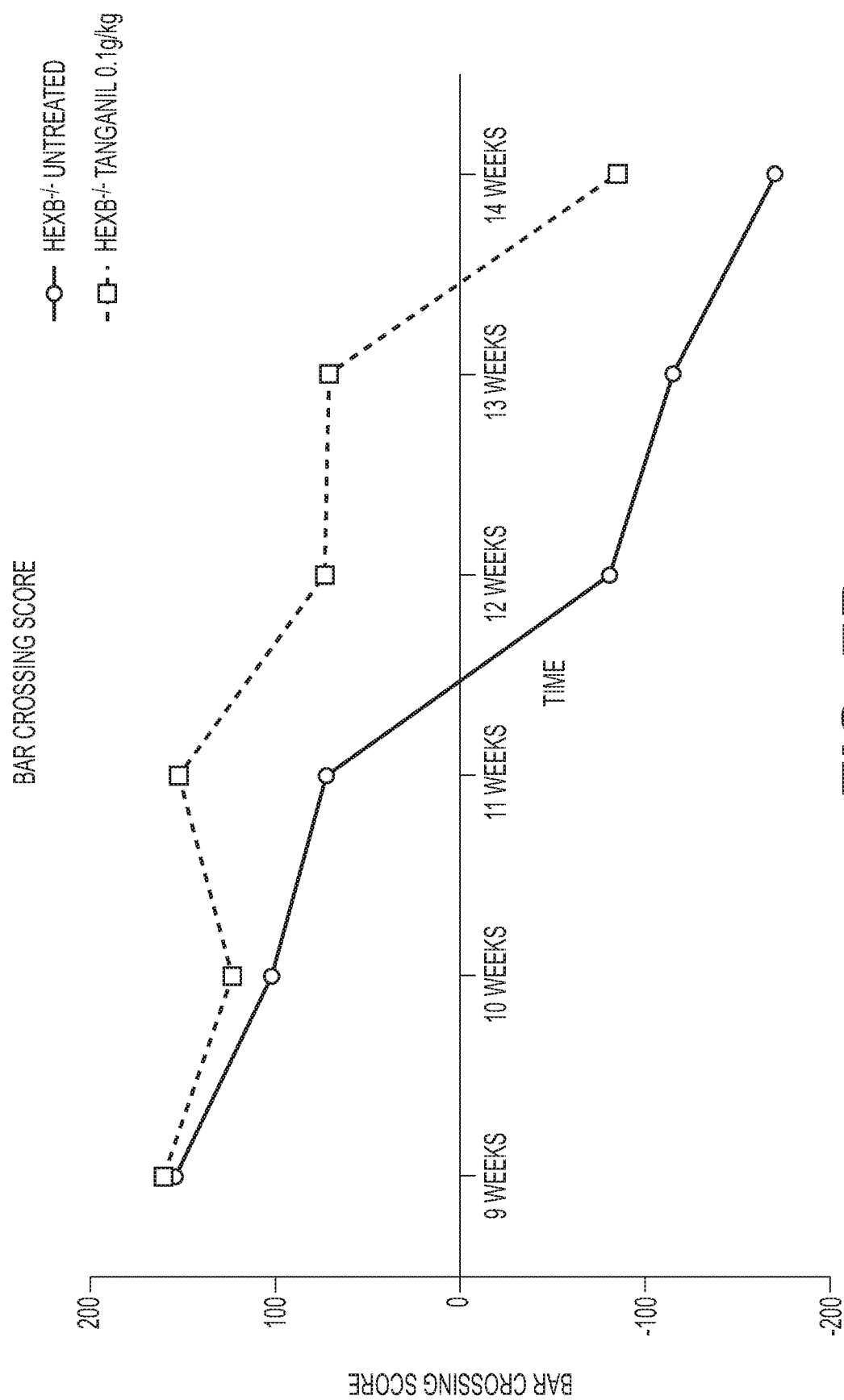
FIG. 7B shows bar crossing scores for untreated and acetyl-leucine-treated Sandhoff model mice.

Treatment of the Sandhoff mouse model with acetyl-DL-leucine (0.1 g/kg body weight from 3 weeks of age) was associated with improved motor function and hind-limb mobility/engagement as assessed via the bar-crossing test (FIG. 7B). In FIG. 7 B, acetyl-leucine treatment of 0.1 g/kg body weight was provided from 3 weeks of age. The acetyl-leucine treated Sandhoff mice retained the ability to complete the test up to 13 weeks of age (inclusive). Data shown is the mean of 6 mice per group. The treated Sandhoff mice retained the ability to complete the test up to 13 weeks of age (inclusive).

Step Cycle

Step cycle is the length of time taken during locomotion by a limb from the time it leaves the ground until it leaves the ground on the next occasion.

Step cycle time was assessed at 12 weeks of age in untreated and acetyl-leucine treated Sandhoff model mice. Acetyl-leucine treatment constituted 0.1 g/kg body weight acetyl-leucine from 3 weeks of age.

Figure 7C:
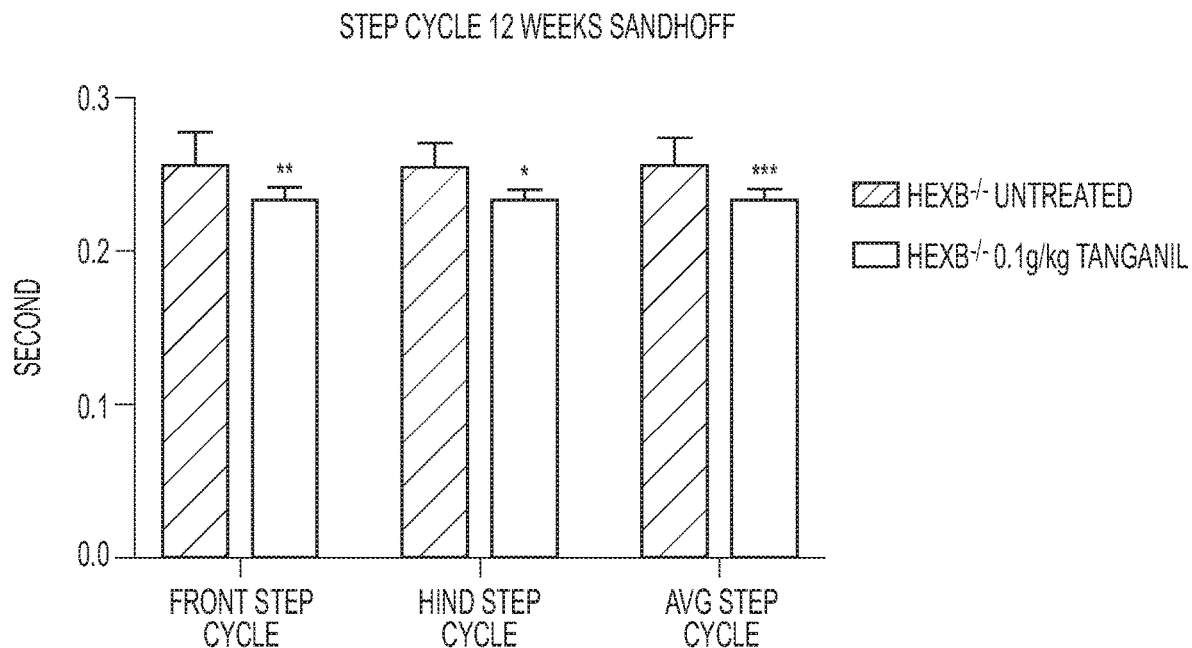
FIG. 7C shows the step cycle time for untreated and acetyl-leucine-treated Sandhoff mice assessed at 12 weeks of age.

Treatment of the Sandhoff mouse model with acetyl-leucine was associated with significantly faster front step cycle times ($p<0.05$ vs untreated SH mouse), significantly faster hind step cycle times ($p<0.01$ vs untreated SH mouse) and significantly faster average step cycle times ($p<0.001$ vs untreated SH mouse) (FIG. 7C). In FIG. 7 C, Acetyl-leucine treatment of 0.1 g/kg body weight was provided from 3 weeks of age. Front step cycle refers to the mouse's front limbs, hind step cycle to the mouse's rear limbs, and average step cycle takes into account all of the mouse's limbs. The asterisks (*//*) indicate p-values of \<0.05/0.01/0.001 versus untreated Sandhoff mouse. Data shown is mean±Stdev.

Thus, acetyl-leucine treatment was associated with a faster step cycle in the Sandhoff mouse model, which may indicate improvement in motor function.

Conclusions

These studies demonstrate that acetyl-leucine treatment of a mouse model of Sandhoff disease may give rise to improvements in motor function as assessed by two independent experiments, as well as significantly increased lifespan.

Example 4

GM2 gangliosidoses are a group of lysosomal storage disorders arising from defects in β-hexosaminidase activity. The group encompasses Tay-Sachs disease, Sandhoff disease, and the AB variant of Tay-Sachs disease.

Fibroblasts derived from GM2 patients (Tay-Sachs disease, Sandhoff disease, and the AB variant of Tay-Sachs disease) and healthy controls were treated with acetyl-DL-leucine (1 mM for 6 days) prior to extraction and quantification of glycosphingolipid (GSL) levels via high performance liquid chromatography (HPLC).

Figure 8A:
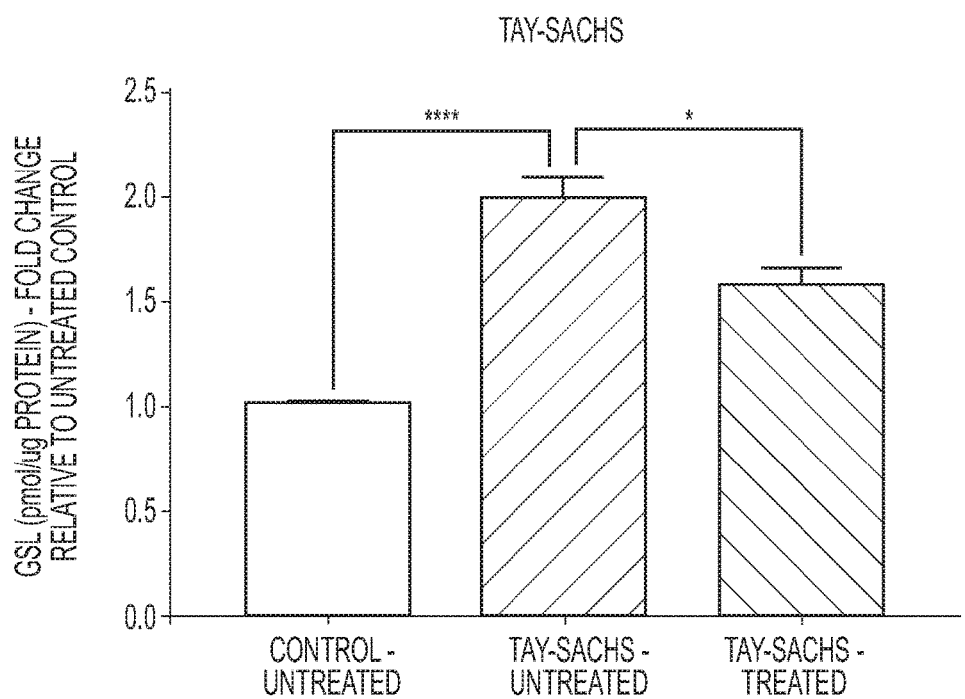
FIGS. 8A-8C show the effect of treatment with acetyl-DL-leucine on glycosphingolipid (GSL) levels in GM2 gangliosidoses patient fibroblasts (Tay-Sachs disease, Sandhoff disease, and AB variant of Tay-Sachs disease, respectively).
Figure 8B:
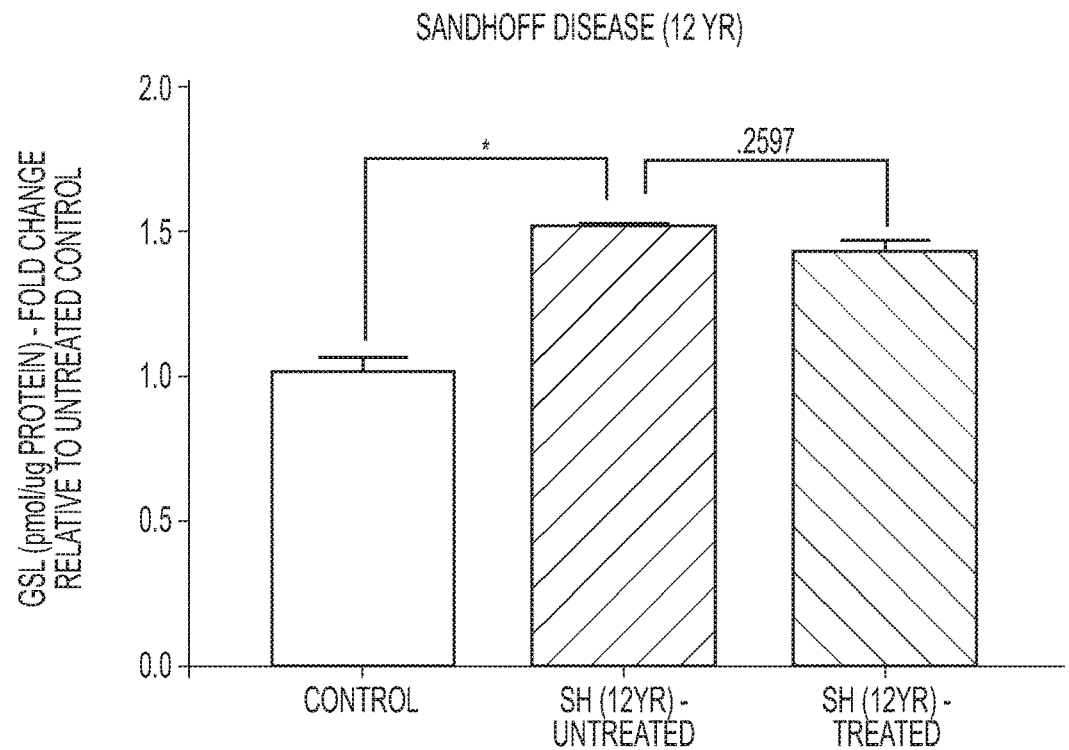
Figure 8C:
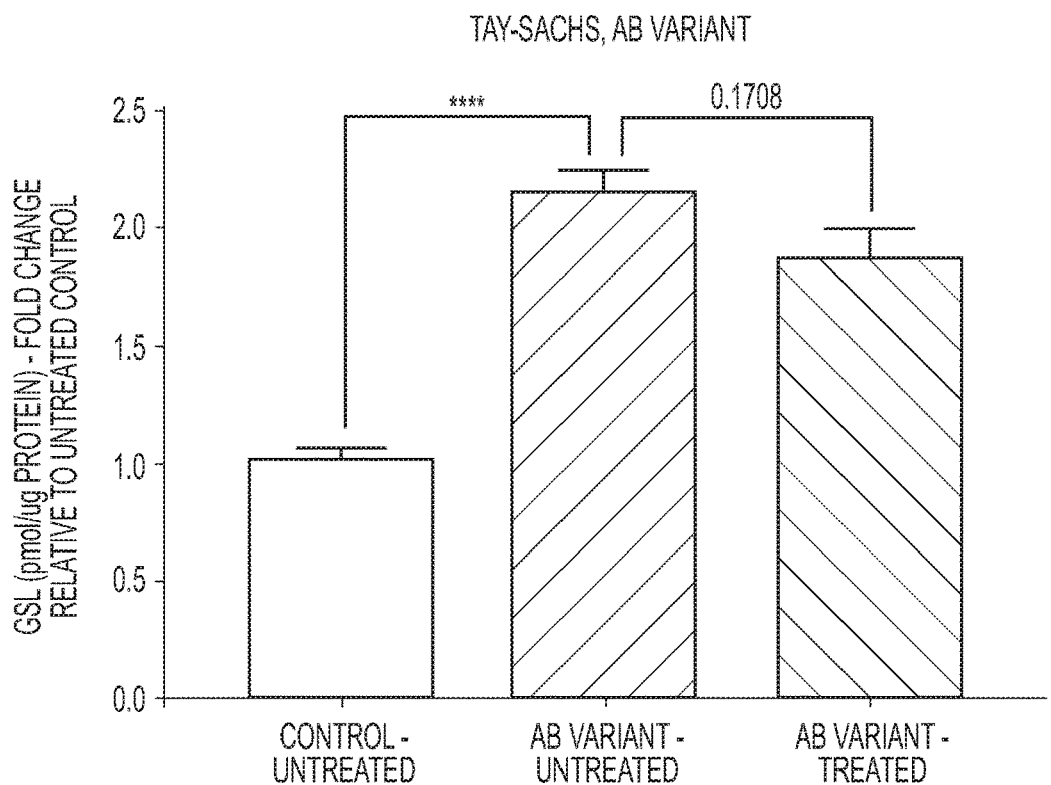

In the absence of treatment, fibroblasts derived from all 3 varieties of GM2 gangliosidosis demonstrated elevated GSL levels when compared to untreated wild-type controls. In all 3 cases, treatment with acetyl-DL-leucine (1 mM for 6 days) was associated with a reduction in GSL storage. In the case of Tay-Sachs disease, this decrease was statistically significant ($p<0.05$). In the case of Sandhoff disease and the AB variant of Tay-Sachs, there was a trend towards decreased GSL levels associated with treatment. Data presented in FIGS. 8A-8C show the results of the treatment for each cell line, respectively, with GSL levels adjusted for protein content and expressed as fold change relative to levels in untreated wild-type fibroblasts.

Example 5

Patient 1

The patient in this case study was a 28 year-old male who was genetically diagnosed with Tay-Sachs disease and who exhibited dysarthrophonia, tremor, ataxia of stance and gait, paraparesis and muscle atrophies. In particular, the patient was not able to stand or walk, could do single steps with strong support, had distinct postural instability, ocular movement disorder, dysphagia and dysarthria, and mild cognitive function disorder. First symptoms were observed at the age of 16 years.

Before treatment was commenced, examination of the patient indicated a Scale for Assessment and Rating of Ataxia (SARA) score of 15.5/40. In addition, results from the patient's Spinocerebellar Ataxia Functional Index (SCAFI) analysis were:

Mean 8-meters Walking Test (8MW): 21.6 s
MW 9-Hole Pegboard Test Dominant (9HPTD) (right): 48.3 s
MW 9-Hole Pegboard Test Non-Dominant (9HPTND): 44.9 s
MW PATA Word Test: 20
Montreal Cognitive Assessment (MoCA): 18/30

Video of the patient was also recorded for later comparison.

The day following this examination, the patient was started on therapy with acetyl-leucine, at a dose of 3 g per day for the first week, followed by a dose of 5 g per day for the second week onwards.

After one month and four months, respectively, the patient was re-examined while continuing treatment. After one month, the patient had improved fine motor skills and reduced hand tremor, for example while eating or drinking. Walking was not markedly changed. After four months, the patient was in stable condition with slightly improved cognitive function but had deterioration of stance, gait and fine motor function. The patient's SARA scores and results from the patient's SCAFI analyses are shown below compared to baseline.

TABLE 1

Patient Evaluation Parameters.

| | Baseline | After one month with acetyl-DL-leucine | After 4 months with acetyl-DL-leucine |
| --- | --- | --- | --- |
| SARA | 15.5/40 | 15.5/40 | 17/40 |
| 8MWT | 21.6 sec | 7 sec | 25.49 sec |

TABLE 1-continued

Patient Evaluation Parameters.

| | Baseline | After one month with acetyl-DL-leucine | After 4 months with acetyl-DL-leucine |
|---|---|---|---|
| 9HPTD | 48.3 sec | 45.9 sec | 48.67 sec |
| 9HPTND | 44.9 sec | 40.1 sec | 47.09 sec |
| PATA | 20 | 22 | 21 |
| MoCA | 18/30 | 21/30 | 22/30 |

Overall, the patient exhibited an improvement in symptoms following acetyl-leucine treatment.

Patient 2

The patient in this case study was a 32 year-old female who was genetically diagnosed with Tay-Sachs disease and who exhibited ataxia of stance and gait, fine motor impairment, paraparesis of lower extremities, and muscle atrophies. In particular, walking was not possible without support, and the patient suffered from dysphagia and speech disorder, ocular movement disorder, and mild cognitive function disorder. First symptoms were observed at the age of 7 years.

Before treatment was commenced, examination of the patient indicated a Scale for Assessment and Rating of Ataxia (SARA) score of 10.5/40. In addition, results from the patient's Spinocerebellar Ataxia Functional Index (SCAFI) analysis were:

Mean 8-meters Walking Test (8MW): 12.5 s

MW 9-Hole Pegboard Test Dominant (9HPTD) (right): 21.5 s

MW 9-Hole Pegboard Test Non-Dominant (9HPTND): 35.5 s

MW PATA Word Test: 18

Montreal Cognitive Assessment (MoCA): 21/30

Video of the patient was also recorded for later comparison.

The day of the examination, the patient was started on therapy with acetyl-leucine at a dose of 3 g per day for the first week, followed by a dose of 5 g per day for the second week onwards.

After one month, the patient was re-examined while continuing treatment and showed increased enunciation, improved postural stability, and enhanced cognitive function. Stance and gait were possible without support. The patient's SARA score and results from the patient's SCAFI analysis are shown below compared to baseline.

TABLE 2

Patient Evaluation Parameters.

| | Baseline | After one month with acetyl-DL-leucine |
|---|---|---|
| SARA | 10.5/40 | 5/40 |
| 8MWT | 12.5 sec | 9.55 sec |
| 9HPTD | 21.5 sec | 34.97 sec |
| 9HPTND | 35.5 sec | 39.34 sec |
| PATA | 18 | 17 |
| MoCA | 21/30 | 25/30 |

Patient 3

The patient in this case study was an 8 year-old male who was genetically diagnosed with Tay-Sachs disease and who had epileptic cramps (tonic-clonic, about 10 seconds, self-limiting) almost every day before falling asleep, ocular movement disorder, anarthria, distinct problems in cognitive function and concentration (neurological examination was not possible), was not able to stand or walk by himself, and was very limited in daily activities (eating, washing or dressing himself was not possible). First symptoms were observed at the age of 9 months.

Before treatment was commenced, examination of the patient indicated a Scale for Assessment and Rating of Ataxia (SARA) score of 36/40, a mRDS score of 18/24, a EQ-5D-5L visual scale of 50, and a 8MWT of 18.1 (only with strong support).

The patient was started on therapy with acetyl-leucine at a dose of 1.5 g per day for the first week, followed by a dose of 3 g per day for the second week onwards.

After one month, the patient was re-examined while continuing treatment and showed increased fine motor skills (was able to grab small things), increased motivation (tried more often to walk by himself), improved postural stability, gait and stance, and could speak single words. The patient's SARA, mRDS, EQ-5D-5L visual scale, and 8MWT scores are shown below compared to baseline.

TABLE 3

Patient Evaluation Parameters.

| | Baseline | After one month on acetyl-DL-leucine |
|---|---|---|
| SARA | 36/40 | 33/40 |
| mRDS | 18/24 | 16/24 |
| EQ-5D-5L visual scale | 50 | 60 |
| 8MWT | 18.1 (only with strong support) | 11.75 (with support of one arm) |

Example 6

The patient in this case study was a 13 year-old male who was genetically diagnosed with GM1 Gangliosidosis and who was not able to stand or walk by himself, was very limited in daily activities (eating, washing, dressing himself was not possible), and had ocular movement disorder, anarthria, and distinct problems in cognitive function and concentration (neurological examination was not possible). First symptoms were observed at the age of 2 years.

Before treatment was commenced, examination of the patient indicated a Scale for Assessment and Rating of Ataxia (SARA) score of 35/40, a mRDS score of 15, and a EQ-5D-5L visual scale of 50.

The patient was started on therapy with acetyl-leucine at a dose of 1.5 g per day for the first week, followed by a dose of 3 g per day for the second week onwards.

After one month, the patient was re-examined while continuing treatment and showed a stable general condition, increased gait (more fluent), and stable stance in natural position. The patient's SARA, mRDS, and EQ-5D-5L visual scale scores are shown below compared to baseline.

TABLE 4

Patient Evaluation Parameters.

| | Baseline | After one month on acetyl-DL-leucine |
|---|---|---|
| SARA | 35/40 | 35/40 |
| mRDS | 15 | 16 |
| EQ-5D-5L visual scale | 50 | 60 |

Example 7

An NPC patient's severity may be quantified by assigning a clinical severity score (CSS), which assesses various parameters of the disease and gives each parameter a score out of 5 (higher score=greater severity). See Yanjanin et al., "Linear Clinical Progression, Independent of Age of Onset, in Niemann-Pick Disease, Type C," *Am J Med Genet Part B* 153B:132-140. In an untreated patient, one can typically predict how the CSS will change over time in an individual, as disease progression appears to be linear. For example, if Patient A moves from a CSS of 8 to a CSS of 12 between month 0 and month 12, it can be predicted that by month 36, the patient will have a CSS of 20. The annual severity increment score (ASIS) quantifies the annual rate of change in the CSS, calculated by dividing the CSS of a patient by the patient's age. For example, if untreated Patient B had a CSS of 8 at two years of age, the patient's ASIS would be 4. Each year, the patient would be expected to progress by 4 CSS points, such that at 4 years of age, the patient's CSS would be 16. If therapeutic intervention slowed or arrested disease progression, one would expect the patient to have a smaller ASIS score after such therapy than at baseline.

Ten NPC patients were administered acetyl-leucine at 4.5 g/day over long durations. A CSS was determined at baseline, and at various time points, for eye movement, ambulation, speech, swallow, fine motor skills, cognition, memory, and seizures. An overall CSS was calculated at baseline and at each such time point by adding the individual CSS values for each parameter (eye movement, ambulation, etc.). The number of days post-initiation of therapy at which CSS was assessed was different for each patient, as shown in Table 5.

TABLE 5

Days post-initiation of acetyl-leucine administration at which CSS was assessed.

| Patient I.D | Baseline (days) | Time Point 2 (days) | Time Point 3 (days) | Time Point 4 (days) |
|---|---|---|---|---|
| 1 | 0 | 126 | 231 | |
| 2 | 0 | 119 | 200 | 297 |
| 3 | 0 | 91 | 240 | |
| 4 | 0 | 107 | 196 | |
| 5 | 0 | 78 | 238 | 414 |
| 6 | 0 | 184 | 238 | 414 |
| 7 | 0 | 81 | 165 | |
| 8 | 0 | 90 | 217 | |
| 9 | 0 | 400 | 644 | |
| 10 | 0 | 83 | | |

Tables 6-14 below show each CSS for overall, eye movement, ambulation, speech, swallow, fine motor skills, cognition, memory, and seizures, respectively.

TABLE 6

CSS overall.

| Clinical Severity Score (CSS) Patient I.D | Baseline | Time Point 2 | Time Point 3 | Time Point 4 |
|---|---|---|---|---|
| 1 | 11 | 11 | 10 | |
| 2 | 33 | 33 | 33 | 33 |
| 3 | 13 | 12 | 11 | |
| 4 | 13 | 13 | 10 | |
| 5 | 12 | 12 | 12 | 12 |
| 6 | 21 | 23 | 21 | 21 |
| 7 | 19 | 19 | 19 | |
| 8 | 13 | 12 | 11 | |
| 9 | 22 | 22 | 21 | |
| 10 | 14 | 11 | | |

TABLE 7

CSS eye movement.

| Clinical Severity Score (CSS) Patient I.D | Baseline | Time Point 2 | Time Point 3 | Time Point 4 |
|---|---|---|---|---|
| 1 | 3 | 3 | 3 | |
| 2 | 3 | 3 | 3 | 3 |
| 3 | 3 | 3 | 3 | |
| 4 | 2 | 2 | 2 | |
| 5 | 3 | 3 | 3 | 3 |
| 6 | 3 | 3 | 3 | 3 |
| 7 | 3 | 3 | 3 | |
| 8 | 3 | 3 | 2 | |
| 9 | 3 | 3 | 3 | |
| 10 | 3 | 3 | | |

TABLE 8

CSS ambulation.

| Clinical Severity Score (CSS) Patient I.D | Baseline | Time Point 2 | Time Point 3 | Time Point 4 |
|---|---|---|---|---|
| 1 | 2 | 2 | 1 | |
| 2 | 5 | 5 | 5 | 5 |
| 3 | 1 | 1 | 1 | |
| 4 | 2 | 2 | 1 | |
| 5 | 1 | 1 | 1 | 1 |
| 6 | 2 | 4 | 2 | 2 |
| 7 | 2 | 2 | 2 | |
| 8 | 1 | 1 | 1 | |
| 9 | 2 | 2 | 2 | |
| 10 | 2 | 2 | | |

TABLE 9

CSS speech.

| Clinical Severity Score (CSS) Patient I.D | Baseline | Time Point 2 | Time Point 3 | Time Point 4 |
|---|---|---|---|---|
| 1 | 1 | 1 | 1 | |
| 2 | 2 | 2 | 2 | 2 |
| 3 | 1 | 1 | 1 | |
| 4 | 2 | 2 | 1 | |
| 5 | 1 | 1 | 1 | 1 |
| 6 | 2 | 2 | 2 | 2 |
| 7 | 1 | 1 | 1 | |
| 8 | 1 | 1 | 1 | |
| 9 | 2 | 2 | 2 | |
| 10 | 1 | 1 | | |

TABLE 10

CSS swallow.

| Clinical Severity Score (CSS) Patient I.D | Baseline | Time Point 2 | Time Point 3 | Time Point 4 |
|---|---|---|---|---|
| 1 | 0 | 0 | 0 | |
| 2 | 4 | 4 | 4 | 4 |

TABLE 10-continued

CSS swallow.

| Clinical Severity Score (CSS) Patient I.D | Baseline | Time Point 2 | Time Point 3 | Time Point 4 |
|---|---|---|---|---|
| 3 | 2 | 2 | 2 | |
| 4 | 2 | 2 | 2 | |
| 5 | 2 | 2 | 2 | 2 |
| 6 | 3 | 3 | 3 | 3 |
| 7 | 3 | 3 | 3 | |
| 8 | 2 | 2 | 2 | |
| 9 | 3 | 3 | 3 | |
| 10 | 2 | 2 | | |

TABLE 11

CSS fine motor skills.

| Clinical Severity Score (CSS) Patient I.D | Baseline | Time Point 2 | Time Point 3 | Time Point 4 |
|---|---|---|---|---|
| 1 | 1 | 1 | 1 | |
| 2 | 5 | 5 | 5 | 5 |
| 3 | 2 | 1 | 1 | |
| 4 | 1 | 1 | 1 | |
| 5 | 1 | 1 | 1 | 1 |
| 6 | 4 | 4 | 4 | 4 |
| 7 | 2 | 2 | 2 | |
| 8 | 2 | 1 | 1 | |
| 9 | 4 | 4 | 4 | |
| 10 | 1 | 1 | | |

TABLE 12

CSS cognition.

| Clinical Severity Score (CSS) Patient I.D | Baseline | Time Point 2 | Time Point 3 | Time Point 4 |
|---|---|---|---|---|
| 1 | 3 | 3 | 3 | |
| 2 | 5 | 5 | 5 | 5 |
| 3 | 3 | 3 | 3 | |
| 4 | 3 | 3 | 3 | |
| 5 | 3 | 3 | 3 | 3 |
| 6 | 4 | 4 | 4 | 4 |
| 7 | 4 | 4 | 4 | |
| 8 | 3 | 3 | 3 | |
| 9 | 4 | 4 | 4 | |
| 10 | 3 | 2 | | |

TABLE 13

CSS memory.

| Clinical Severity Score (CSS) Patient I.D | Baseline | Time Point 2 | Time Point 3 | Time Point 4 |
|---|---|---|---|---|
| 1 | 1 | 1 | 1 | |
| 2 | 4 | 4 | 4 | 4 |
| 3 | 1 | 1 | 0 | |
| 4 | 1 | 1 | 0 | |
| 5 | 1 | 1 | 1 | 1 |
| 6 | 3 | 3 | 3 | 3 |
| 7 | 4 | 4 | 4 | |
| 8 | 1 | 1 | 1 | |
| 9 | 4 | 4 | 3 | |
| 10 | 2 | 0 | | |

TABLE 14

CSS seizures.

| Clinical Severity Score (CSS) Patient I.D | Baseline | Time Point 2 | Time Point 3 | Time Point 4 |
|---|---|---|---|---|
| 1 | 0 | 0 | 0 | |
| 2 | 5 | 5 | 5 | 5 |
| 3 | 0 | 0 | 0 | |
| 4 | 0 | 0 | 0 | |
| 5 | 0 | 0 | 0 | 0 |
| 6 | 0 | 0 | 0 | 0 |
| 7 | 0 | 0 | 0 | |
| 8 | 0 | 0 | 0 | |
| 9 | 0 | 0 | 0 | |
| 10 | 0 | 0 | | |

The ASIS at baseline and each time point was calculated using each patient's CSS and age at the time of assessment. The overall ASIS for each patient at each time point is shown below in Table 15.

TABLE 15

ASIS overall.

| Annual Severity Increment Scores (ASIS) Baseline | Time Point 2 | Time Point 3 | Time Point 4 |
|---|---|---|---|
| 0.381371618 | 0.376864272 | 0.339262493 | |
| 1.94125463 | 1.904748736 | 1.880675612 | 1.852636028 |
| 0.65 | 0.592617631 | 0.53250497 | |
| 0.481909063 | 0.476731928 | 0.363469002 | |
| 0.433188377 | 0.429874461 | 0.423232908 | 0.416160273 |
| 0.561964246 | 0.607297766 | 0.552333117 | 0.545420607 |
| 0.536675431 | 0.533334614 | 0.529913714 | |
| 0.486750384 | 0.445200609 | 0.402903129 | |
| 0.738624874 | 0.71243018 | 0.665646967 | |
| 0.595597228 | 0.406038403 | | |

Figure 9A:
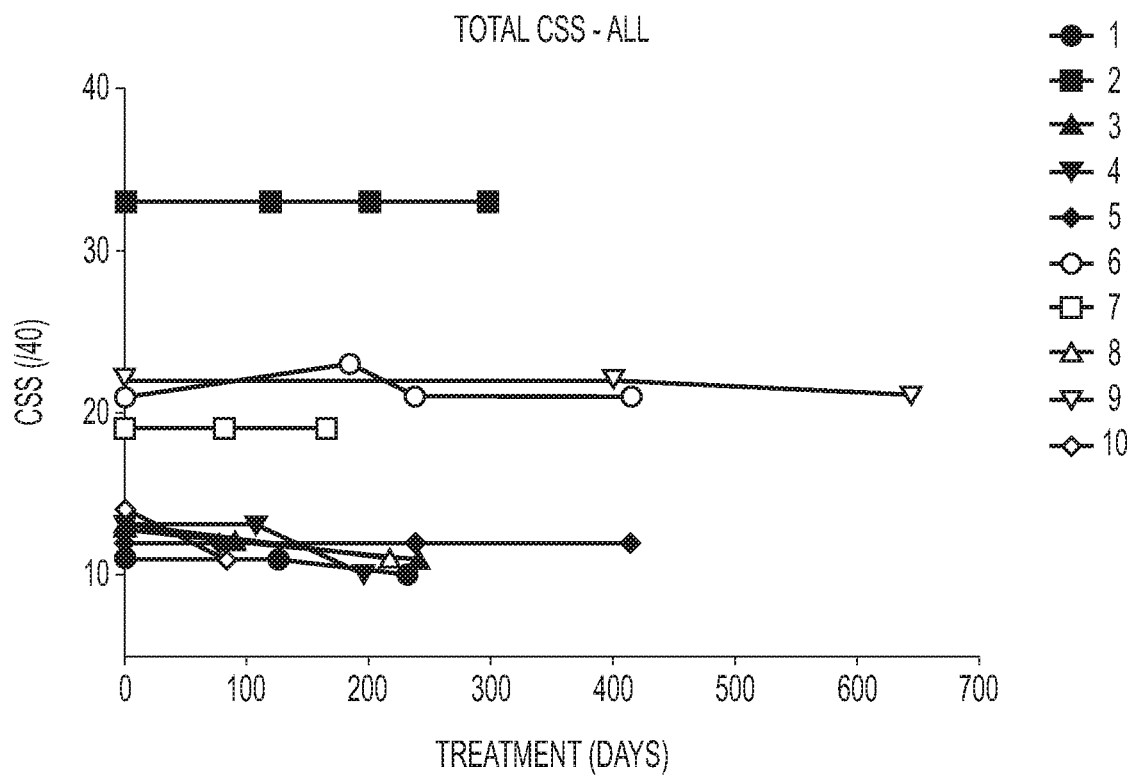
FIGS. 9A and 9B show the effect of treatment with acetyl-DL-leucine over time on the overall clinical severity score (CSS) and overall annual severity increment score (ASIS), respectively, of ten NPC patients.

As shown in Table 6 and FIG. 9A, none of the ten patients showed an overall increase in CSS over the course of the experiment. Patient 6 showed an increased CSS between baseline and time point 2, but returned to baseline by time point 3 and remained there at time point 4. Four of the ten patients (Patients 2, 5, 6, and 7) had a constant CSS over the course of the experiment, indicating that the disease did not progress in these individuals. Six of the ten patients (Patients 1, 3, 4, 8, 9, and 10) showed a reduction in CSS over the course of the experiment, indicating that the disease did not progress and actually became less severe. Improvements were seen in different subscores: Patient 1: ambulation; Patient 3: fine motor skills; Patient 4: ambulation and speech; Patient 8: eye movement and fine motor skills; Patient 9: memory; Patient 10: cognition. Data presented in FIGS. 10A-10J show the CSS subscores for each patient, respectively, in the form of a bar graph.

Figure 9B:
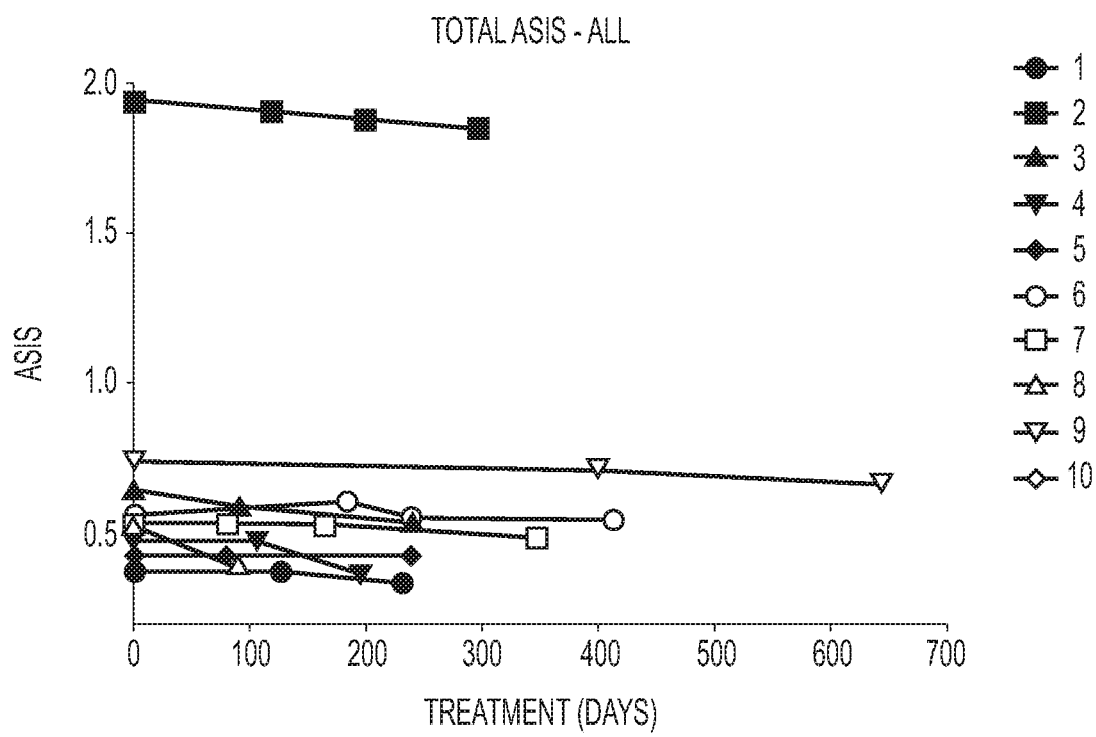
Figure 10A:
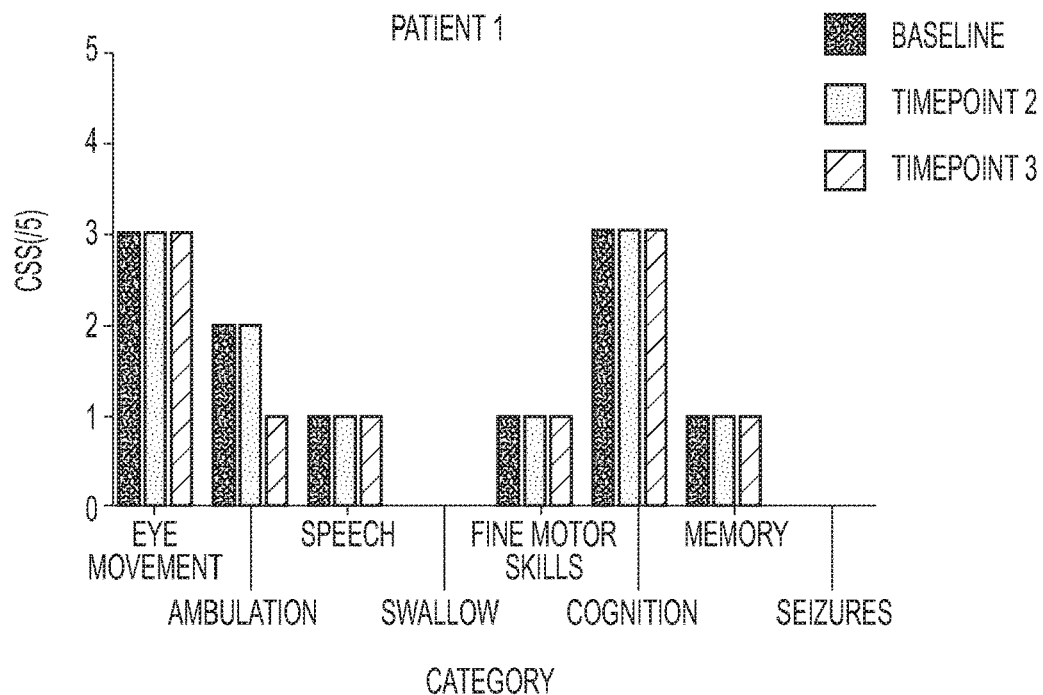
FIGS. 10A-10J show the effect of treatment with acetyl-DL-leucine over time on the CSS subscores for each of the ten NPC patients.
Figure 10B:
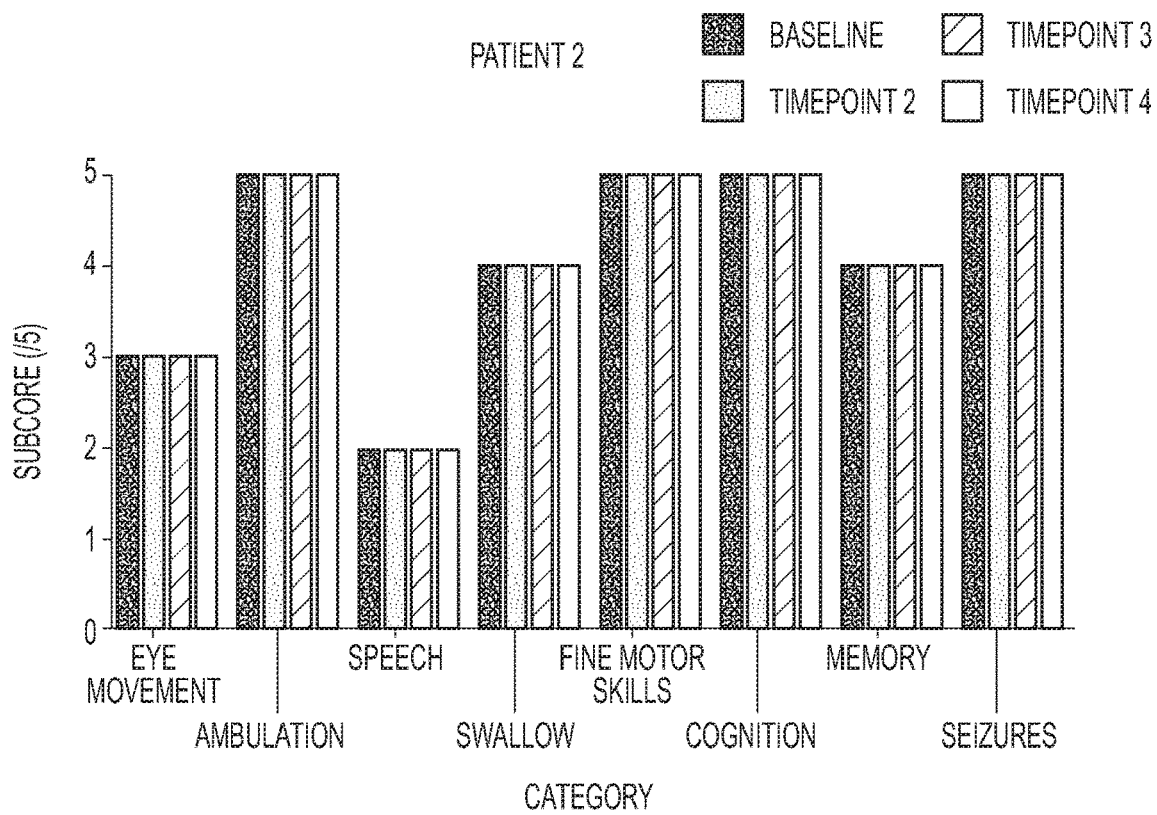
Figure 10C:
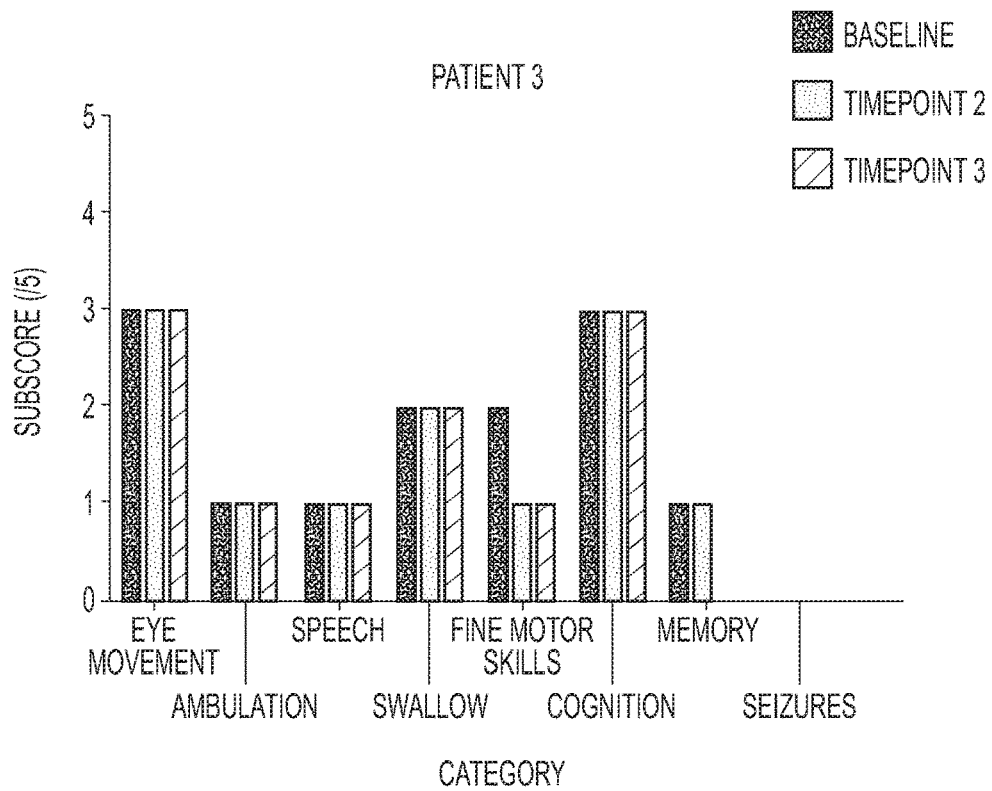
Figure 10D:
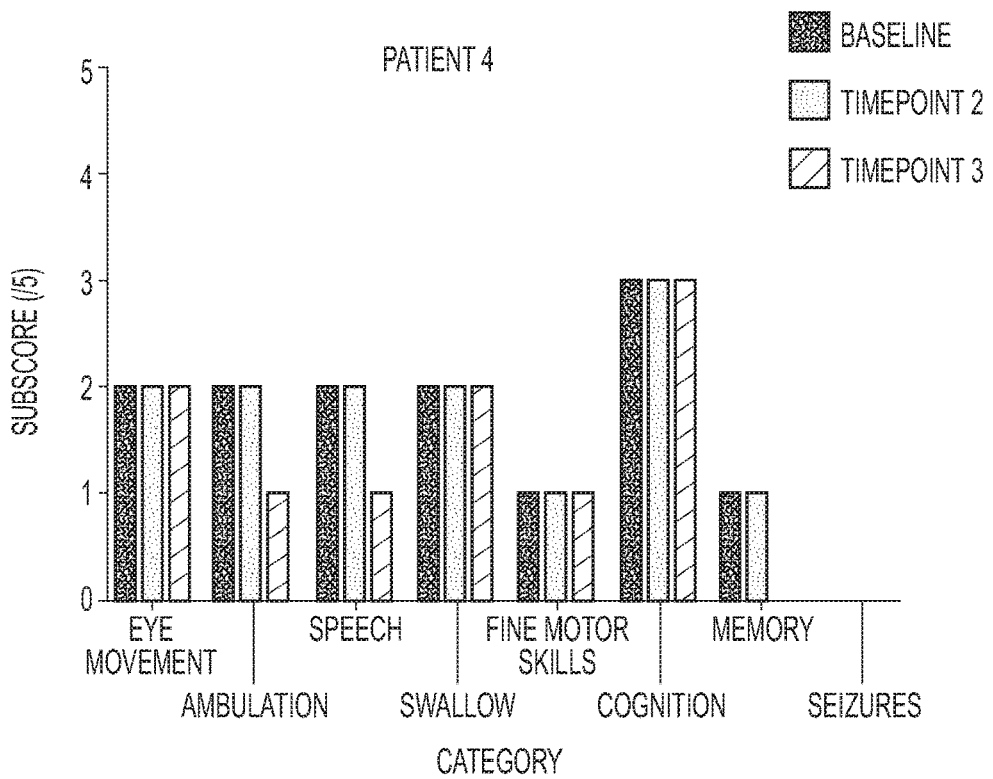
Figure 10E:
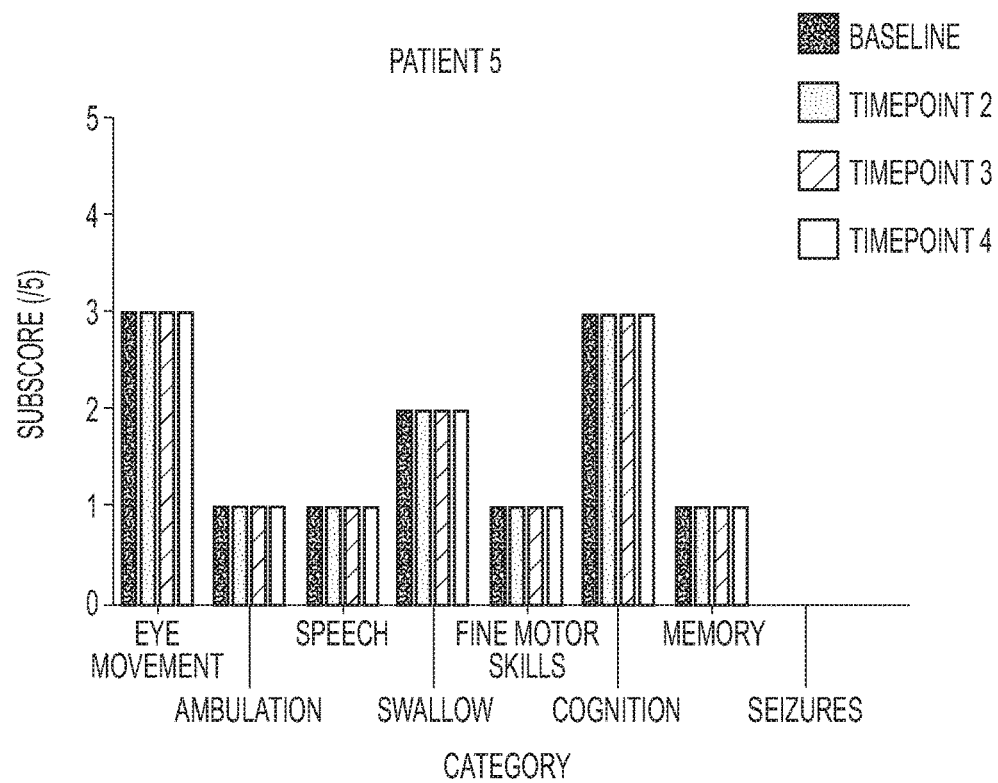
Figure 10F:
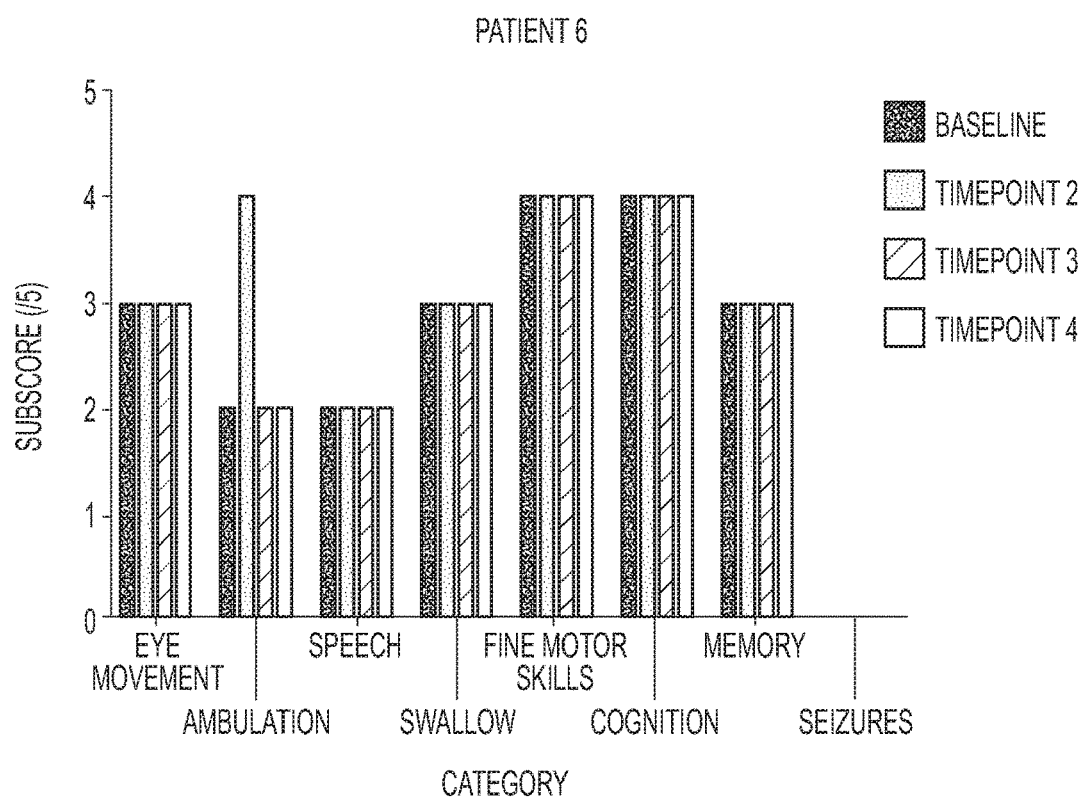
Figure 10G:
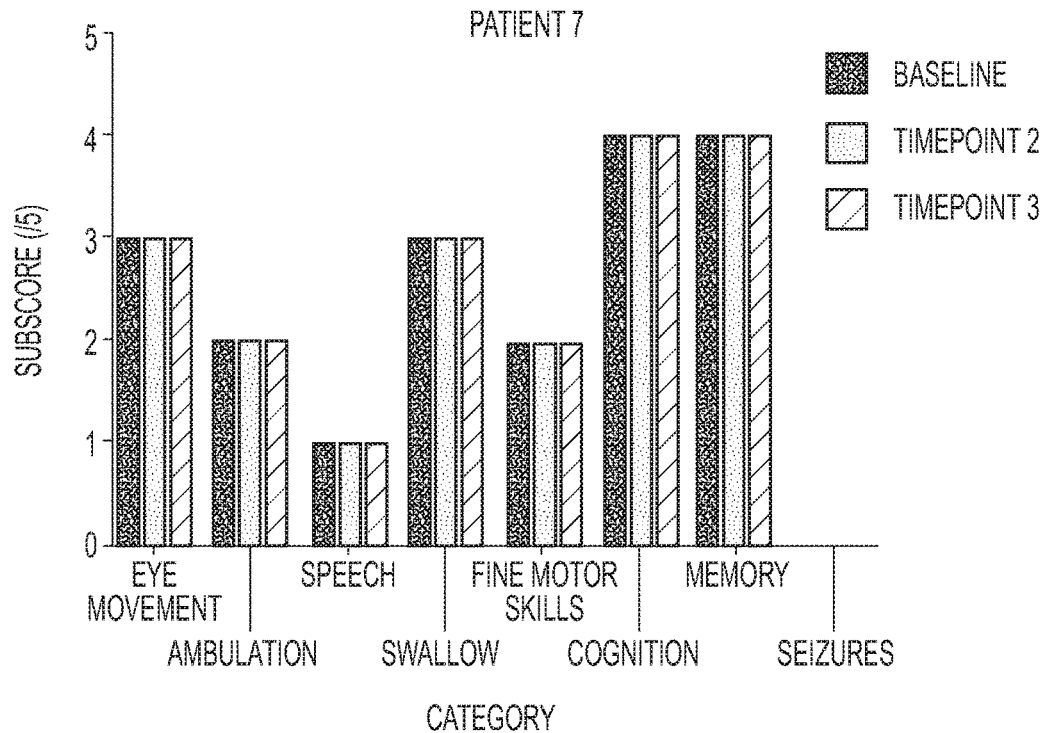
Figure 10H:
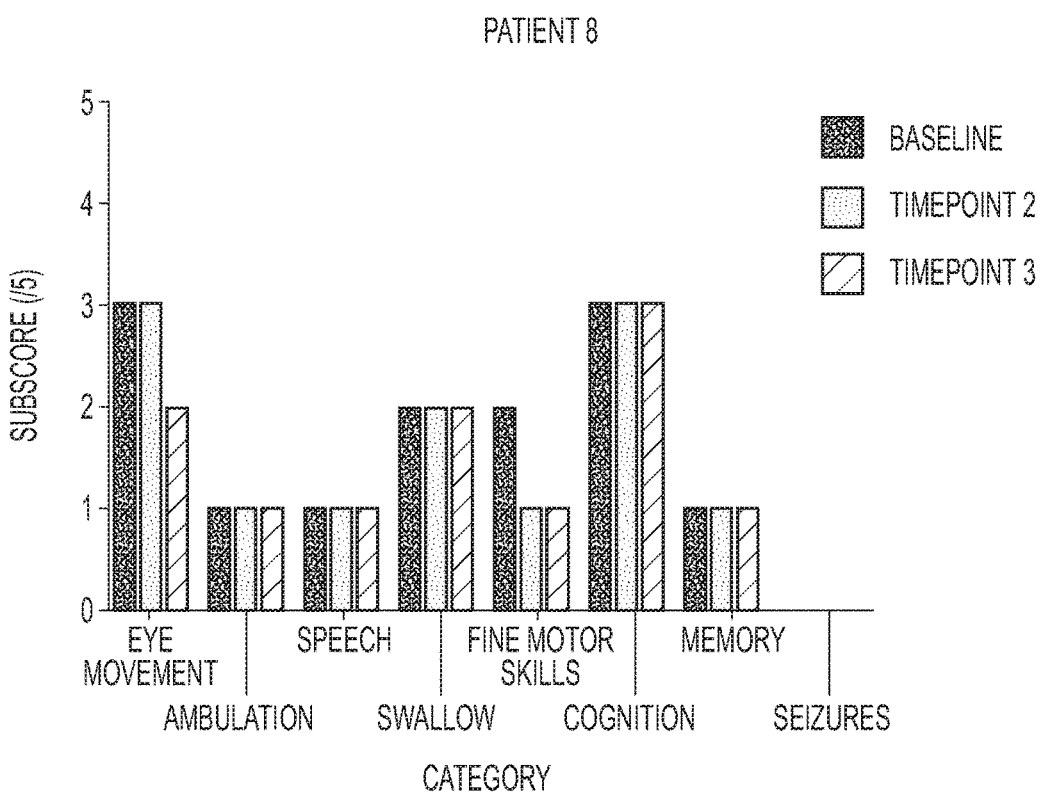
Figure 10I:
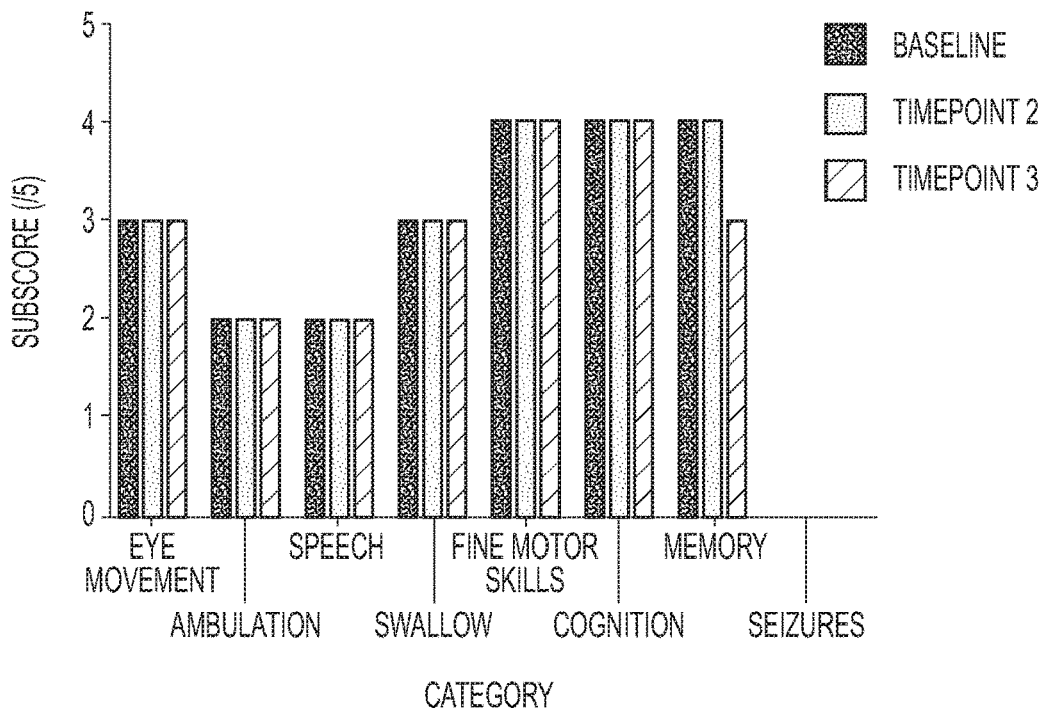
Figure 10J:
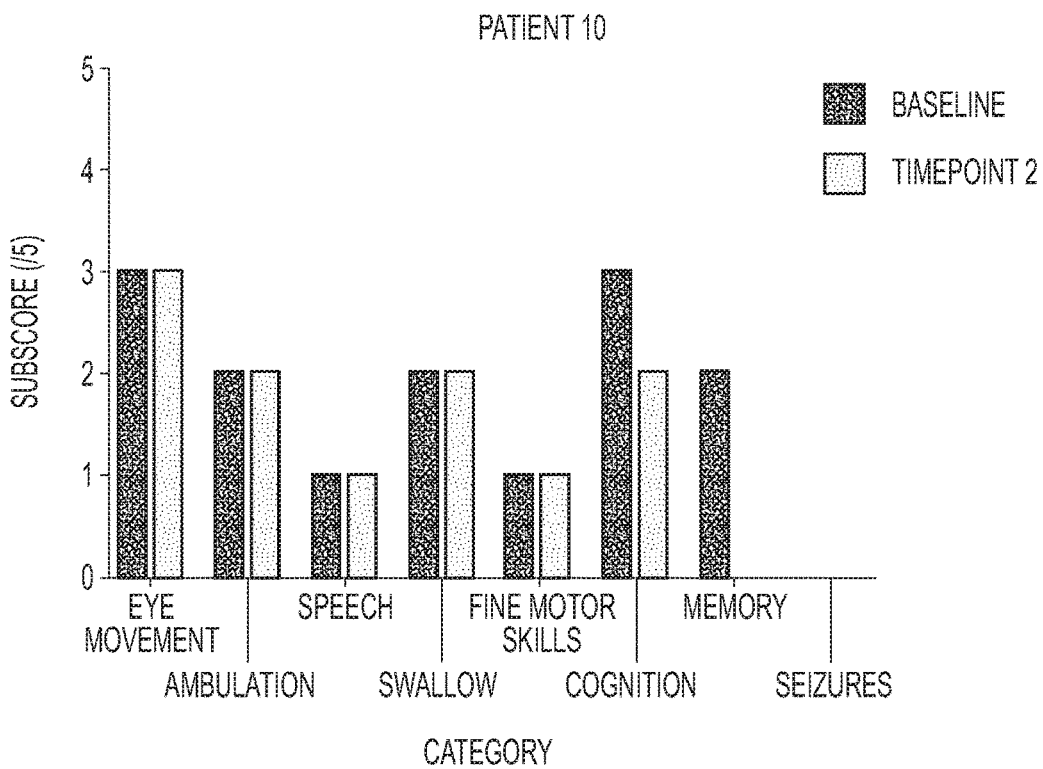

As shown in Table 15 and FIG. 9B, all ten patients showed a reduction in ASIS during treatment relative to ASIS at baseline. In Patients 2, 5, 6, and 7, CSS remained the same while age increased, resulting in a small reduction in ASIS. In Patients 1, 3, 4, 8, 9, and 10, the reduction in ASIS was larger due to CSS decreasing while age increased.

The invention claimed is:
1. A method of treating a lysosomal storage disorder (LSD) or one or more symptoms associated with the LSD in a subject in need thereof comprising:
   administering a therapeutically effective amount of acetyl-leucine or a pharmaceutically acceptable salt thereof to the subject for a duration chosen from at least about 3 months, at least about 6 months, at least about 1 year, at least about 2 years, and at least about 5 years, wherein the LSD is chosen from Niemann-Pick type C disease, Tay-Sachs disease, the AB variant of Tay-Sachs disease, Sandhoff disease, Niemann-Pick type A disease, Niemann-Pick type B disease, Fabry disease, neuronal ceroid lipofuscinoses, Krabbe disease, Farber disease, Gaucher disease, metachromatic leukodystrophy, multiple sulphatase deficiency, mucolipidosis II, mucolipidosis III, MPS III, MPS VII, GM1 gangliosidosis, and aspartylglucosaminuria.

2. A method of delaying progression of a lysosomal storage disorder (LSD) or more symptoms associated with the LSD over time as compared to typical disease progression in a subject in need thereof comprising:
administering a therapeutically effective amount of acetyl-leucine or a pharmaceutically acceptable salt thereof to the subject for a duration chosen from at least about 3 months, at least about 6 months, at least about 1 year, at least about 2 years, and at least about 5 years.

3. A method of reversing progression of a lysosomal storage disorder (LSD) or one or more symptoms associated with the LSD over time in a subject in need thereof comprising:
administering a therapeutically effective amount of acetyl-leucine or a pharmaceutically acceptable salt thereof to the subject for a duration chosen from at least about 3 months, at least about 6 months, at least about 1 year, at least about 2 years, and at least about 5 years.

4. A method of improving in a subject in need thereof a biochemical marker of a lysosomal storage disorder (LSD) over time comprising:
administering a therapeutically effective amount of acetyl-leucine or a pharmaceutically acceptable salt thereof to the subject for a duration chosen from at least about 3 months, at least about 6 months, at least about 1 year, at least about 2 years, and at least about 5 years.

5. A method of reducing the severity of a lysosomal storage disorder (LSD) or reducing the severity of or eliminating one or more existing symptoms associated with the LSD in a subject in need thereof comprising:
administering a therapeutically effective amount of acetyl-leucine or a pharmaceutically acceptable salt thereof to the subject, wherein the LSD is not Niemann-Pick Type C.

6. A method of providing neuroprotection in a subject having, suspected of having, or at risk of having a lysosomal storage disorder (LSD) or one or more symptoms associated with the LSD comprising:
administering a therapeutically effective amount of acetyl-leucine or a pharmaceutically acceptable salt thereof to the subject for a duration chosen from at least about 3 months, at least about 6 months, at least about 1 year, at least about 2 years, and at least about 5 years.

7. A method of delaying or reversing progression of a lysosomal storage disorder (LSD) or reducing the severity of the LSD in a subject in need thereof comprising:
administering a therapeutically effective amount of acetyl-leucine or a pharmaceutically acceptable salt thereof to the subject, wherein the LSD is not Niemann-Pick Type C and the subject is asymptomatic.

8. The method according to claim 4, wherein the biochemical marker is increased lysosomal volume.

9. The method according to claim 1, wherein the method comprises initiating administration of a therapeutically effective amount of acetyl-leucine to the subject in need thereof when the subject is asymptomatic.

10. The method according to claim 4, wherein the initial administration occurs after the subject has been found to have a genetic and/or biochemical marker of the LSD.

11. The method according to claim 1, wherein the acetyl-leucine is acetyl-DL-leucine.

12. The method according to claim 1, wherein the acetyl-leucine has an enantiomeric excess of the L-enantiomer or the D-enantiomer.

13. The method according to claim 1, wherein the acetyl-leucine is in a single enantiomeric form of either the L-enantiomer or the D-enantiomer.

14. The method according to claim 13, wherein the single enantiomeric form is the L-enantiomer.

15. The method according to claim 1, wherein the method comprises administering the acetyl-leucine to the subject in need thereof at a therapeutically effective amount of from about 1 g to about 15 g per day.

16. The method according to claim 1, wherein the LSD is chosen from Niemann-Pick type A disease, Niemann-Pick type B disease, and Niemann-Pick type C disease.

17. The method according to claim 15, wherein the method comprises administering the acetyl-leucine to the subject in need thereof at a therapeutically effective amount chosen from about 1 g to about 10 g per day, about 1.5 g to about 7 g per day, about 4 g to about 6 g per day, or about 4 g to about 5 g per day.

18. The method according to claim 1, wherein the LSD is chosen from Tay-Sachs disease, Sandhoff disease, Niemann-Pick type A disease, Niemann-Pick type C disease, mucolipidosis II, MPS III, and GM1 gangliosidosis.

19. The method according to claim 2, wherein the method comprises initiating administration of a therapeutically effective amount of acetyl-leucine to the subject in need thereof when the subject is asymptomatic.

20. The method according to claim 2, wherein the therapeutically effective amount of acetyl-leucine or a pharmaceutically acceptable salt thereof ranges from about 1 g to about 15 g per day.

21. The method according to claim 2, wherein the LSD is chosen from Tay-Sachs disease, Sandhoff disease, Niemann-Pick type A disease, Niemann-Pick type C disease, mucolipidosis II, MPS III, and GM1 gangliosidosis.

22. The method according to claim 3, wherein the therapeutically effective amount of acetyl-leucine or a pharmaceutically acceptable salt thereof ranges from about 1 g to about 15 g per day.

23. The method according to claim 3, wherein the LSD is chosen from Tay-Sachs disease, Sandhoff disease, Niemann-Pick type A disease, Niemann-Pick type C disease, mucolipidosis II, MPS III, and GM1 gangliosidosis.

24. The method according to claim 4, wherein the method comprises initiating administration of a therapeutically effective amount of acetyl-leucine to the subject in need thereof when the subject is asymptomatic.

25. The method according to claim 4, wherein the therapeutically effective amount of acetyl-leucine or a pharmaceutically acceptable salt thereof ranges from about 1 g to about 15 g per day.

26. The method according to claim 4, wherein the LSD is chosen from Tay-Sachs disease, Sandhoff disease, Niemann-Pick type A disease, Niemann-Pick type C disease, mucolipidosis II, MPS III, and GM1 gangliosidosis.

27. The method according to claim 5, wherein the therapeutically effective amount of acetyl-leucine or a pharmaceutically acceptable salt thereof ranges from about 1 g to about 15 g per day.

28. The method according to claim 5, wherein the LSD is chosen from Tay-Sachs disease, Sandhoff disease, Niemann-Pick type A disease, Niemann-Pick type C disease, mucolipidosis II, MPS III, and GM1 gangliosidosis.

29. The method according to claim 6, wherein the method comprises initiating administration of a therapeutically effective amount of acetyl-leucine to the subject in need thereof when the subject is asymptomatic.

30. The method according to claim 6, wherein the therapeutically effective amount of acetyl-leucine or a pharmaceutically acceptable salt thereof ranges from about 1 g to about 15 g per day.

31. The method according to claim 6, wherein the LSD is chosen from Tay-Sachs disease, Sandhoff disease, Niemann-Pick type A disease, Niemann-Pick type C disease, mucolipidosis II, MPS III, and GM1 gangliosidosis.

32. The method according to claim 7, wherein the therapeutically effective amount of acetyl-leucine or a pharmaceutically acceptable salt thereof ranges from about 1 g to about 15 g per day.

33. The method according to claim 7, wherein the LSD is chosen from Tay-Sachs disease, Sandhoff disease, Niemann-Pick type A disease, mucolipidosis II, MPS III, and GM1 gangliosidosis.

34. The method according to claim 7, wherein the therapeutically effective amount of acetyl-leucine or a pharmaceutically acceptable salt thereof is administered to the subject for a duration chosen from at least about 3 months, at least about 6 months, at least about 1 year, at least about 2 years, and at least about 5 years.

* * * * *

(12) EX PARTE REEXAMINATION CERTIFICATE (253rd)
Ex Parte Reexamination Ordered under 35 U.S.C. 257

United States Patent
Strupp

(10) Number: US 11,400,067 C1
(45) Certificate Issued: *May 28, 2025

(54) PHARMACEUTICAL COMPOSITIONS AND USES DIRECTED TO LYSOSOMAL STORAGE DISORDERS

(71) Applicant: INTRABIO LIMITED, Oxfordshire (GB)

(72) Inventor: Michael Strupp, Munich (DE)

(73) Assignee: INTRABIO LIMITED

Supplemental Examination Request:
No. 96/050,055, Oct. 9, 2024

Reexamination Certificate for:
Patent No.: 11,400,067
Issued: Aug. 2, 2022
Appl. No.: 16/324,301
PCT Filed: Aug. 11, 2017
PCT No.: PCT/IB2017/054928
§ 371 (c)(1),
(2) Date: Feb. 8, 2019
PCT Pub. No.: WO2018/029657
PCT Pub. Date: Feb. 15, 2018

(*) Notice: This patent is subject to a terminal disclaimer.

(51) Int. Cl.
*A61K 31/198* (2006.01)
*A61K 31/13* (2006.01)
*A61P 25/00* (2006.01)

(52) U.S. Cl.
CPC ............ *A61K 31/198* (2013.01); *A61K 31/13* (2013.01); *A61P 25/00* (2018.01)

(58) Field of Classification Search
None
See application file for complete search history.

(56) References Cited

To view the complete listing of prior art documents cited during the supplemental examination proceeding and the resulting reexamination proceeding for Control Number 96/050,055, please refer to the USPTO's Patent Electronic System.

*Primary Examiner* — Alan D Diamond

(57) ABSTRACT

The present disclosure provides for treating lysosomal storage disorders (LSDs) comprising administering acetyl-leucine or a pharmaceutically acceptable salt thereof.

US 11,400,067 C1

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 7 and 32-34 is confirmed.

Claims 1-6 and 28 are determined to be patentable as amended.

Claims 8-27 and 29-31, dependent on an amended claim, are determined to be patentable.

New claims 35-43 are added and determined to be patentable.

1. A method of treating a lysosomal storage disorder (LSD) or one or more symptoms associated with the LSD in a subject in need thereof comprising:
administering a therapeutically effective amount of acetyl-leucine or a pharmaceutically acceptable salt thereof to the subject for a duration chosen from at least [about] 3 months, at least [about] 6 months, at least [about] 1 year, at least [about] 2 years, and at least [about] 5 years, *wherein the LSD is chosen from Niemann-Pick type C disease, Tay-Sachs disease, the AB variant of Tay-Sachs disease, Sandhoff disease, Niemann-Pick type A disease, Niemann-Pick type B disease, Fabry disease, neuronal ceroid lipofuscinoses, Krabbe disease, Farber disease, Gaucher disease, metachromatic leukodystrophy, multiple sulphatase deficiency, mucolipidosis II, mucolipidosis III, MPS III, MPS VII, GM1 gangliosidosis, and aspartylglucosaminuria.*

2. A method of delaying progression of a lysosomal storage disorder (LSD) or *one or* more symptoms associated with the LSD over time as compared to typical disease progression in a subject in need thereof comprising: administering a therapeutically effective amount of acetyl-leucine or a pharmaceutically acceptable salt thereof to the subject for a duration chosen from at least [about] 3 months, at least [about] 6 months, at least [about] 1 year, at least [about] 2 years, and at least [about] 5 years, *wherein the LSD is chosen from Niemann-Pick type C disease, Tay-Sachs disease, the AB variant of Tay-Sachs disease, Sandhoff disease, Niemann-Pick type A disease, Niemann-Pick type B disease, Fabry disease, neuronal ceroid lipofuscinoses, Krabbe disease, Farber disease, Gaucher disease, metachromatic leukodystrophy, multiple sulphatase deficiency, mucolipidosis II, mucolipidosis III, MPS III, MPS VII, GM1 gangliosidosis, and aspartylglucosaminuria.*

3. A method of reversing progression of a lysosomal storage disorder (LSD) or one or more symptoms associated with the LSD over time in a subject in need thereof comprising: administering a therapeutically effective amount of acetyl-leucine or a pharmaceutically acceptable salt thereof to the subject for a duration chosen from at least [about] 3 months, at least [about] 6 months, at least [about] 1 year, at least [about] 2 years, and at least [about] 5 years, *wherein the LSD is chosen from Niemann-Pick type C disease, Tay-Sachs disease, the AB variant of Tay-Sachs disease, Sandhoff disease, Niemann-Pick type A disease, Niemann-Pick type B disease, Fabry disease, neuronal ceroid lipofuscinoses, Krabbe disease, Farber disease, Gaucher disease, metachromatic leukodystrophy, multiple sulphatase deficiency, mucolipidosis II, mucolipidosis III, MPS III, MPS VII, GM1 gangliosidosis, and aspartylglucosaminuria.*

4. A method of improving in a subject in need thereof a biochemical marker of a lysosomal storage disorder (LSD) over time comprising:
administering a therapeutically effective amount of acetyl-leucine or a pharmaceutically acceptable salt thereof to the subject for a duration chosen from at least [about] 3 months, at least [about] 6 months, at least [about] 1 year, at least [about] 2 years, and at least [about] 5 years, *wherein the LSD is chosen from Niemann-Pick type C disease, Tay-Sachs disease, the AB variant of Tay-Sachs disease, Sandhoff disease, Niemann-Pick type A disease, Niemann-Pick type B disease, Fabry disease, neuronal ceroid lipofuscinoses, Krabbe disease, Farber disease, Gaucher disease, metachromatic leukodystrophy, multiple sulphatase deficiency, mucolipidosis II, mucolipidosis III, MPS III, MPS VII, GM1 gangliosidosis, and aspartylglucosaminuria.*

5. A method of reducing the severity of a lysosomal storage disorder (LSD) or reducing the severity of or eliminating one or more existing symptoms associated with the LSD in a subject in need thereof comprising:
administering a therapeutically effective amount of acetyl-leucine or a pharmaceutically acceptable salt thereof to the subject, wherein the LSD is not Niemann-Pick Type C, *and wherein the LSD is chosen from Tay-Sachs disease, the AB variant of Tay-Sachs disease, Sandhoff disease, Niemann-Pick type A disease, Niemann-Pick type B disease, Fabry disease, neuronal ceroid lipofuscinoses, Krabbe disease, Farber disease, Gaucher disease, metachromatic leukodystrophy, multiple sulphatase deficiency, mucolipidosis II, mucolipidosis III, MPS III, MPS VII, GM1 gangliosidosis, and aspartylglucosaminuria.*

6. A method of providing neuroprotection in a subject having, suspected of having, or at risk of having a lysosomal storage disorder (LSD) or one or more symptoms associated with the LSD comprising:
administering a therapeutically effective amount of acetyl-leucine or a pharmaceutically acceptable salt thereof to the subject for a duration chosen from at least [about] 3 months, at least [about] 6 months, at least [about] 1 year, at least [about] 2 years, and at least [about] 5 years, *wherein the LSD is chosen from Niemann-Pick type C disease, Tay-Sachs disease, the AB variant of Tay-Sachs disease, Sandhoff disease, Niemann-Pick type A disease, Niemann-Pick type B disease, Fabry disease, neuronal ceroid lipofuscinoses, Krabbe disease, Farber disease, Gaucher disease, metachromatic leukodystrophy, multiple sulphatase deficiency, mucolipidosis II, mucolipidosis III, MPS_III, MPS VII, GM1 gangliosidosis, and aspartylglucosaminuria.*

28. The method according to claim 5, wherein the LSD is chosen from Tay-Sachs disease, Sandhoff disease, Niemann-Pick type A disease, [Niemann-Pick type C disease,] mucolipidosis II, MPS III, and GM1 gangliosidosis.

*35. A method of treating Niemann-Pick Type C (NPC) disease or one or more symptoms associated with NPC in a subject in need thereof comprising:* administering a therapeutically effective amount of acetyl-leucine or a pharmaceutically acceptable salt thereof to the subject for a duration chosen from at least 3 months, at least 6 months, at least 1 year, at least 2 years, and at least 5 years.

36. A method of treating a lysosomal storage disorder (LSD) or one or more symptoms associated with the LSD in a subject in need thereof comprising:

administering a therapeutically effective amount of acetyl-leucine or a pharmaceutically acceptable salt thereof to the subject for a duration chosen from at least 6 months, at least 1 year, at least 2 years, and at least 5 years, wherein the LSD is chosen from Niemann-Pick type C disease, Tay-Sachs disease, the AB variant of Tay-Sachs disease, Sandhoff disease, Niemann-Pick type A disease, Niemann-Pick type B disease, Fabry disease, neuronal ceroid lipofuscinoses, Krabbe disease, Farber disease, Gaucher disease, metachromatic leukodystrophy, multiple sulphatase deficiency, mucolipidosis II, mucolipidosis III, MPS III, MPS VII, GM1 gangliosidosis, and aspartylglucosaminuria.

37. The method according to claim 36, wherein the acetyl-leucine is acetyl-DL-leucine.

38. The method according to claim 36, wherein the acetyl-leucine has an enantiomeric excess of the L-enantiomer or the D-enantiomer.

39. The method according to claim 36, wherein the acetyl-leucine is in a single enantiomeric form of either the L-enantiomer or the D-enantiomer.

40. The method according to claim 39, wherein the single enantiomeric form is the L-enantiomer.

41. The method according to claim 36, wherein the method comprises administering the acetyl-leucine to the subject in need thereof at a therapeutically effective amount of from about 1 g to about 15 g per day.

42. The method according to claim 36, wherein the LSD is chosen from Niemann-Pick type A disease, Niemann-Pick type B disease, and Niemann-Pick type C disease.

43. The method according to claim 36, wherein the LSD is chosen from Tay-Sachs disease, Sandhoff disease, Niemann-Pick type A disease, Niemann-Pick type C disease, mucolipidosis II, MPS III, and GM1 gangliosidosis.

\* \* \* \* \*